(12) United States Patent
Mjalli et al.

(10) Patent No.: US 7,423,177 B2
(45) Date of Patent: Sep. 9, 2008

(54) CARBOXAMIDE DERIVATIVES AS THERAPEUTIC AGENTS

(75) Inventors: Adnan M. M. Mjalli, Jamestown, NC (US); Robert C. Andrews, Jamestown, NC (US); Ramesh Gopalaswamy, Jamestown, NC (US); Chris Wysong, Winston-Salem, NC (US)

(73) Assignee: TransTech Pharma, Inc., High Point, NC (US)

(*) Notice: Subject to any disclaimer, the term of this patent is extended or adjusted under 35 U.S.C. 154(b) by 0 days.

(21) Appl. No.: 10/091,759

(22) Filed: Mar. 5, 2002

(65) Prior Publication Data

US 2002/0193432 A1    Dec. 19, 2002

Related U.S. Application Data

(60) Provisional application No. 60/273,454, filed on Mar. 5, 2001, provisional application No. 60/273,445, filed on Mar. 5, 2001, provisional application No. 60/273,429, filed on Mar. 5, 2001, provisional application No. 60/273,455, filed on Mar. 5, 2001, provisional application No. 60/273,446, filed on Mar. 5, 2001, provisional application No. 60/273,404, filed on Mar. 5, 2001, provisional application No. 60/273,403, filed on Mar. 5, 2001.

(51) Int. Cl.
C07C 237/00 (2006.01)
C07C 233/00 (2006.01)
C07C 235/00 (2006.01)
A01N 37/18 (2006.01)

(52) U.S. Cl. .................. 564/192; 564/194; 564/200; 564/202; 564/211; 514/613

(58) Field of Classification Search .............. 560/27, 560/13, 18, 28; 514/480, 485, 486, 307, 514/330, 399, 423, 459, 619, 621; 564/157, 564/158; 546/146; 548/333.5, 561; 549/426
See application file for complete search history.

(56) References Cited

U.S. PATENT DOCUMENTS

| | | | |
|---|---|---|---|
| 4,166,452 A | 9/1979 | Generales, Jr. | |
| 4,265,874 A | 5/1981 | Bonsen et al. | |
| 4,356,108 A | 10/1982 | Schwab et al. | |
| 4,873,313 A | 10/1989 | Crawford et al. | |
| 5,202,424 A | 4/1993 | Vlassara et al. | |
| 5,585,344 A | 12/1996 | Vlassara et al. | |
| 5,688,653 A | 11/1997 | Ulrich et al. | |
| 5,864,018 A | 1/1999 | Morser et al. | |
| 5,922,770 A * | 7/1999 | Peschke et al. | 514/619 |
| 5,939,526 A | 8/1999 | Gaugler et al. | |
| 6,100,098 A | 8/2000 | Newkirk | |
| 6,613,801 B2 * | 9/2003 | Mjalli et al. | 514/514 |
| 7,067,554 B2 * | 6/2006 | Mjalli et al. | 514/514 |

| | | |
|---|---|---|
| 2004/0097407 A1 | 5/2004 | Mjalli et al. |

FOREIGN PATENT DOCUMENTS

| | | |
|---|---|---|
| GB | 2 005 674 | 4/1979 |
| JP | 7-51550 | * 6/1995 |
| WO | WO 95/09838 | 4/1995 |
| WO | WO 95/35279 | 12/1995 |
| WO | WO 96/32385 | 10/1996 |
| WO | WO 97/22618 | 6/1997 |
| WO | WO 97/26913 | 7/1997 |
| WO | WO 97/39121 | 10/1997 |
| WO | WO 9739125 | 10/1997 |
| WO | WO 98/22138 | 5/1998 |
| WO | WO 98/33492 | 8/1998 |
| WO | WO 99/07402 | 2/1999 |
| WO | WO 99/18987 | 4/1999 |
| WO | WO 99/25690 | 5/1999 |
| WO | WO 99/50230 | 10/1999 |
| WO | WO 99/54485 | 10/1999 |
| WO | WO 00/20458 | 4/2000 |
| WO | WO 00/20621 | 4/2000 |
| WO | WO 01/12598 | 2/2001 |

OTHER PUBLICATIONS

Chem. Abst. 116:58986 (1992).*
Dobrev et al., Khimicheski Fakultet (1978), vol. Date 1975-1976, 70, Pt. 1, 201-7, CAS online abstract retrieved Apr. 16, 2007 from STN, Columbus, OH, USA.*
Albercio, F. & Carpino, L.A., "Coupling Reagents and Activation" *Methods in Enzymology* 289:104-126, Academic Press, San Diego (1997).

(Continued)

*Primary Examiner*—Karl Puttlitz
(74) *Attorney, Agent, or Firm*—Samuel B. Rollins

(57) ABSTRACT

This invention provides certain compounds, methods of their preparation, pharmaceutical compositions comprising the compounds, and their use in treating human or animal disorders. The compounds of the invention are useful as modulators of the interaction between the receptor for advanced glycated end products (RAGE) and its ligands, such as advanced glycated end products (AGEs), S100/calgranulin/EN-RAGE, β-amyloid and amphoterin, and for the management, treatment, control, or as an adjunct treatment for diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

43 Claims, No Drawings

OTHER PUBLICATIONS

Barton, J.W., "In Protection of N-H Bonds and NR$_3$" *Protective Groups in Organic Chemistry*, J.F.W. McOmie, ED., Plenum Press, New York, NY (1973).

Berge, S.M., et al., "Pharmaceutical Salts" *Journal of Pharmaceutical Sciences* 66:1-19 (1977).

Chitaley, K., et al., "Antagonism of Rho-Kinase Stimulates Rate Penile Erection via a Nitric Oxide-Independent Pathway" *Nature Medicine* 7:119-122 (2002).

Degenhardt, T.P., et al., "Chemical Modification of Proteins by Methylglyoxal" *Cell Mol. Biol.*, 44:1139-1145 (1998).

Dyer, D.G., et al., "Accumulation of Maillard Reaction Products in Skin Collagen in Diabetes and Aging" *J. Clin. Invest.*, 91:2463-2469 (1993).

Dyer, D.G., et al., "Formation of Pentosidine during Nonenzymatic Browning of Proteins by Glucose" *J. Biol. Chem.*, 266:11654-11660 (1991).

Greene, T.W., "Protection for the Amino Group" *Protective Groups in Organic Synthesis*, John Wiley and Sons, New York, NY, Chapter 7 (1981).

Hammes, H.P., et al., "Diabetic Retinopathy Risk Correlates with Intracellular Concentrations of the Glycoxidation Product N$^\epsilon$-(Carboxymethyl) Lysine Independently of Glycohaemoglobin Concentrations" *Diabetologia*, 42:603-607 (1999).

Hoffman, M.A., et al., "RAGE Mediates a Novel Proinflammatory Axis: A Central Cell Surface Receptor for S100/Calgranulin Polypeptides" *Cell*, 97:889-901 (1999).

Hori, O., et al., "The Receptor for Avanced Glycation End Products (RAGE) is a Cellular Binding site for Amphoterin" *J. Biol. Chem.*, 270:25752-761 (1995).

Huttunen, H.J., et al., "Receptor for Advanced Glycation End Products (RAGE)- Mediated Neurite Outgrowth and Activation of NF-Kappa B Require the Cytoplasmic Domain of the Receptor But Different Downstream Signaling Pathways" *J. Biol. Chem.* 274(28):19919-24 (1999).

Kumar, S.R., et al., "RAGE at the Blood-Brain Barrier Mediates Neurovascular Dysfunction Caused by Amyloid$\beta_{1-40}$ Peptide" *Neurosci. Program*, 141-#255.19 (2000).

Leder, A. et al., "v-HA-*ras* Transgene Abrogates the Initiation Step in Mouse Skin Tumorigenesis: Effects of Phorbol Esters and Retinoic Acid" *Proc. Natl. Acad. Sci., USA*, 87:9178-9182 (1990).

Li, J. et al., "Sp1-Binding elements in the Promoter of RAG Are Essential for Amphoterin-Mediated Gene Expression in Cultured Neuroblastoma Cells." *J. Biol. Chem.*, 273:30870-30878 (1998).

Li, J. et al., "Characterization and Functional Analysis of the Promoter of RAGE, the Receptor for Advanced Glycation End Products," *J. Biol. Chem.*, 272:16498-16506 (1997).

Lugering, N. et al., "The Myeloic Related Protein MRP8/14 (27E10 Antigen)—Usefulness as a Potential Marker for Disease Activity in Ulcerative Colitis and Putative Biological Function" Eur. J. Clin. Invest., 25:659-664 (1995).

Miyata, T. et al., "$\beta_2$-Microglobulin Modified with Advanced Glycation End Products Is a Major Component of Hemodialysis-Associated Amyloidosis" *J. Clin. Invest.*, 92:1243-1252 (1993).

Miyata, T. et al., "The Receptor for Advanced Glycation End Products (RAGE) Is a Central Mediator of the Interaction of AGE-$\beta_2$Microglobulin with Human Mononuclear Phagocytes Via an Oxidant-Sensitive Pathway" *J. Clin. Invest.*, 98:1088-1094 (1996).

Neeper, M., et al., "Cloning and Expression of a Cell Surface Receptor for Advanced Glycosylation End Products of Proteins" *J. Biol. Chem.*, 267:14998-15004 (1992).

Parkkinen, J. et al., "Amphoterin, the 30-kDa Protein in a Family of HMG1-Type Polypeptides" *J. Biol Chem.*, 268:19726-19738 (1993).

Rammes, A. et al., "Myeloid-Related Protein (MRP) 8 and MRP 14, Calcium-Binding Proteins of the S100 Family, Are Secreted by Activated Monocytes via a Novel, Tubulin-Dependent Pathway *J. Biol. Chem.*, 272:9496-9502 (1997).

Rauvala, H. et al., "Isolation and Some Characteristics of an Adhesive Factor of Brain That Enhances Neurite Outgrowth in Central Neurons" *J. Biol. Chem.*, 262:16625-16635 (1987).

Reddy, S. et al., "N$^\epsilon$-(Carboxymethyl) Lysine Is a Dominant Advanced Glycation End Product (AGE) Antigen in Tissue Proteins" *Biochem.*, 34:10872-10878 (1995).

Schafer, B.W., et al., "The S100 Family of EF-Hand Calcium-Binding Proteins: Functions and Pathology" *TIBS*, 21:134-140 (1996).

Schleicher, E.D., et al., "Increased Accumulation of the Glycoxidation Product N$^\epsilon$-(Carboxymethyl) Lysine in Human Tissues in Diabetes and Aging" *J. Clin. Invest.*, 99(3):457-468 (1997).

Schmidt, A.M. et al., "The Dark Side of Glucose" *Nature Med.*, 1:1002-1004 (1995).

Schmidt, A.M., et al., "The V-Domain of Receptor for Advanced Glycation Endproducts (RAGE) Mediates Binding of AGEs: A Novel Target for Therpy of Diabetic Complications:" *Supplement to Circulation* vol. 96, #194 (1997).

Taguchi, A. et al., "Blockade of RAGE—Amphoterin Signalling Suppresses Tumour Growth and Metastases" *Nature*, 405:354-360 (2000).

Tanaka, N., et al., "The Receptor for Advanced Glycation End Products Is Induced by the Glycation Products Themselves and Tumor Necrosis Factor-α through Nuclear FactorκB, and by 17β-Estradoil through Sp-1 in Human Vascular Endothelial Cells"*J. Biol. Chem.*, 275:25781-25790 (2000).

Teillet et al., "Food Restriction Prevents Advanced Glycation End Product Accumulation and Retards Kidney Aging in Lean Rats" *J. Am. Soc. Nephrol.*, 11:1488-1497 (2000).

Vlassara, H., "Advanced Glycation End-Products and Atherosclerosis" *The Finnish Medical Society DUODECIM, Ann. Med.*, 28:419-426 (1996).

Wautier et al., "Receptor-Mediated Endothelial Cell Dysfunction in Diabetic Vasculopathy: Soluble Receptor for Advanced Glycation End Products Blocks Hyperpermeability in Diabetic Rats" *J.Clin. Invest.*, 97:238-243 (1996).

Yan, S.-D., et al., "RAGE and Amyloid-β Peptide Neurotoxicity in Alzheimer's Disease" *Nature* 382:685-691 (1996).

Yan, S.-D., et al., "An Intracellular Protein That Binds Amyloid-β Peptide and Mediates Neurotoxicity in Alzheimer's Disease" *Nature*, 389:689-695, (1997).

Yan, S.-D. et al., "Amyloid-β Peptide—Receptor for Advanced Glycation Endproduct Interaction Elicits Neuronal Expression of Macrophage-Colony Stimulating Factor: A Proinflammatory Pathway in Alzheimer Disease" *Proc. Natl. Acad. Sci., USA*, 94:5296-5301 (1997).

Yan, S.-D. et al., "Receptor-Dependent Cell Stress and Amyloid Accumulation in Systemic Amyloidosis" *Nat. Med.* 6:643-651 (2000).

Yan, S.-D. et al., "Enhanced Cellular Oxidant Stress by the Interaction of Advanced Glycation Endproducts With Their Receptors Binding Proteins" J. Biol. Chem. 269:9889-9897 (1994).

Zimmer, D. et al., The S100 Protein Family: History, Function, and Expression *Brain Res. Bull*, 37:417-429 (1995).

International Search Report for PCT/US 01/17251 dated Aug. 14, 2001.

* cited by examiner

CARBOXAMIDE DERIVATIVES AS THERAPEUTIC AGENTS

STATEMENT OF RELATED APPLICATIONS

The present application claims priority under 35 USC 119 from the following U.S. Provisional Applications: Ser. No. 60/273,454, filed Mar. 5, 2001, entitled Alpha-Substituted Amide Derivatives of Alpha-Amino Acids as Therapeutic Agents; Ser. No. 60/273,445, filed Mar. 5, 2001, entitled Substituted Heterocyclyl Carboxamide Derivatives as Therapeutic Agents; Ser. No. 60/273,429, filed Mar. 5, 2001, entitled Amino Alkanoic Acid Amides as Therapeutic Agents; Ser. No. 60/273,455, filed Mar. 5, 2001, entitled Substituted Azacycloalkyl Carboxamide Derivatives as Therapeutic Agents; Ser. No. 60/273,446, filed Mar. 5, 2001, entitled Fused Aryl Heterocyclyl Carboxamide Derivatives as Therapeutic Agents; Ser. No. 60/273,404, filed Mar. 5, 2001, entitled Arylalkanoic Acid Derivatives as Therapeutic Agents; and Ser. No. 60/273,403, filed Mar. 5, 2001, entitled Alkyl Imidazole Carboxamide Derivatives as Therapeutic Agents, the disclosures of which are hereby incorporated herein.

FIELD OF THE INVENTION

This invention relates to compounds which are modulators of the receptor for advanced glycated end products (RAGE) and interaction with its ligands such as advanced glycated end products (AGEs), S100/calgranulin/EN-RAGE, β-amyloid and amphoterin, for the management, treatment, control, or as an adjunct treatment of diseases caused by RAGE.

BACKGROUND OF THE INVENTION

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycosylation End Products (AGEs). Factors which promote formation of AGEs included delayed protein turnover (e.g. as in amyloidoses), accumulation of macromolecules having high lysine content, and high blood glucose levels (e.g. as in diabetes) (Hori et al., *J. Biol. Chem.* 270: 25752-761, (1995)). AGEs have implicated in a variety of disorders including complications associated with diabetes and normal aging.

AGEs display specific and saturable binding to cell surface receptors on endothelial cells of the microvasculature, monocytes and macrophages, smooth muscle cells, mesengial cells, and neurons. The Receptor for Advanced Glycated End-products (RAGE) is a member of the immunoglobulin super family of cell surface molecules. The extracellular (N-terminal) domain of RAGE includes three immunoglobulintype regions, one V (variable) type domain followed by two C-type (constant) domains (Neeper et al., *J. Biol. Chem.* 267:14998-15004 (1992). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al., *J. Biol. Chem.* 270:25752-761 (1995)). Increased levels of RAGE are also found in aging tissues (Schleicheret al., *J. Clin. Invest.* 99 (3): 457-468 (1997)), and the diabetic retina, vasculature and kidney (Schmidt et al., *Nature Med.* 1:1002-1004 (1995)). Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest* 97:238-243 (1995)), nephropathy (Teillet et al., *J. Am. Soc. Nephrol.* 11:1488-1497 (2000)), atherosclerosis (Vlassara et al., *The Finnish Medical Society DUODECIM, Ann. Med.* 28:419-426 (1996)), and retinopathy (Hammes et al., *Diabetologia* 42:603-607 (1999)). RAGE has also been implicated in Alzheimer's disease (Yan et al., *Nature* 382: 685-691, (1996)), erectile dysfunction, and in tumor invasion and metastasis (Taguchi et al., *Nature* 405: 354-357, (2000)).

In addition to AGEs, other compounds can bind to, and modulate RAGE. In normal development, RAGE interacts with amphoterin, a polypeptide which mediates neurite outgrowth in cultured embryonic neurons (Hori et al., 1995). RAGE has also been shown to interact with EN-RAGE, a protein having substantial similarity to calgranulin Hofmann et al., Cell 97:889-901 (1999)). RAGE has also been shown to interact with β-amyloid (Yan et al., *Nature* 389:589-595, (1997); Yan et al., *Nature* 382:685-691 (1996); Yan et al., *Proc. Natl. Acad. Sci.,* 94:5296-5301 (1997)).

Binding of ligands such as AGEs, S100/calgranulin/EN-RAGE, β-amyloid, CML ($N^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target for down-regulation of the pathophysiological changes brought about by excessive concentrations of AGEs and other ligands for RAGE.

Thus, there is a need for the development of compounds that antagonize binding of physiological ligands to the RAGE receptor.

SUMMARY OF THE INVENTION

This invention provides certain substituted carboxamide compounds, wherein the amide moiety is comprised of at least one lipophilic group. Embodiments of the present invention provide compounds of Formula (I) as depicted below; methods of their preparation; pharmaceutical compositions comprising the compounds; and methods for their use in treating human or animal disorders. Compounds of the invention are useful as modulators of the interaction of the receptor for advanced glycated end products (RAGE) with its ligands such as advanced glycated end products (AGEs), S100/calgranulin/EN-RAGE, β-amyloid and amphoterin. The compounds are useful in a variety of applications including the management, treatment, control, and/or as an adjunct of diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

DETAILED DESCRIPTION OF THE INVENTION

In a first aspect, the present invention provides certain substituted carboxamide derivatives. Such compounds are useful in the modulation, preferably in the inhibition, of the interaction of RAGE with its physiological ligands, as will be discussed in more detail below.

In a second aspect, the present invention provides compounds of Formula (I):

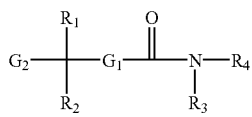

(I)

wherein
$G_1$ comprises $C_1$-$C_6$ alkylene or $(CH_2)_k$, where k is 0 to 3;
$G_2$ comprises a) hydrogen
  b) —$C_{1-6}$ alkyl;
  c) -aryl;
  d) —$C_{1-6}$ alkylaryl e)

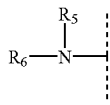

where $R_5$ and $R_6$ independently comprise
  i) —H;
  ii) —$C_{1-6}$ alkyl;
  iii) -aryl;
  iv) —$C_{1-6}$, alkylaryl;
  v) —C(O)—O—$C_{1-6}$ alkyl;
  vi) —C(O)—O—$C_{1-6}$ alkylaryl;
  vii) —C(O)—O—$C_{1-6}$ alkylcycloalkylaryl;
  viii) —C(O)—NH—$C_{1-6}$ alkyl;
  ix) —C(O)—NH—$C_{1-6}$ alkylaryl;
  x) —$SO_2$—$C_{1-6}$ alkyl;
  xi) —$SO_2$—$C_{1-6}$ alkylaryl;
  xii) —$SO_2$-aryl;
  xiii) —$SO_2$—NH—$C_{1-6}$ alkyl;
  xiv) —$SO_2$—NH—$C_{1-6}$ alkylaryl;

xv)

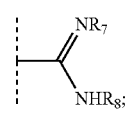

xvi) —C(O)—$C_{1-6}$ alkyl; or
  xvii) —C(O)—$C_{1-6}$ alkylaryl; or f) a group of the formula

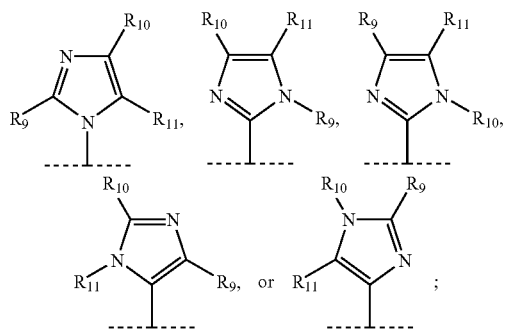

wherein
$R_9$, $R_{10}$, and $R_{11}$ may comprise hydrogen; or
$R_9$, $R_{10}$, and $R_{11}$ independently comprise
  i) —$C_{1-6}$ alkyl;
  ii) -aryl;
  iii) —$C_{1-6}$ alkylaryl;
  iv) —C(O)—O—$C_{1-6}$ alkyl;
  v) —C(O)—O—$C_{1-6}$ alkylaryl;
  vi) —C(O)—NH—$C_{1-6}$ alkyl;
  vii) —C(O)—NH—$C_{1-6}$ alkylaryl;
  viii) —$SO_2$—$C_{1-6}$ alkyl;
  ix) —$SO_2$—$C_{1-6}$ alkylaryl;
  x) —$SO_2$-aryl;
  xi) —$SO_2$—NH—$C_{1-6}$ alkyl;
  xii) —$SO_2$—NH—$C_{1-6}$ alkylaryl;
  xiii) —C(O)—$C_{1-6}$ alkyl; or
  xiv) —C(O)—$C_{1-6}$ alkylaryl;
or $R_{10}$ and $R_{11}$ may be taken together to constitute a fused cycloalkyl, fused heterocyclyl, or fused aryl ring containing the atoms to which $R_{10}$ and $R_{11}$ are bonded;
$R_1$ comprises
  a) hydrogen;
  b) —$C_{1-6}$ alkyl;
  c) -aryl; or
  d) —$C_{1-6}$ alkylaryl;
$R_2$ comprises
  a) —$C_{1-6}$ alkyl;
  b) -aryl;
  c) —$C_{1-6}$ alkylaryl; or
  d) a group of the formula

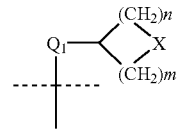

wherein m and n are independently selected from 1, 2, 3, or 4;
X comprises a direct bond, $CH_2$—, —O—, —S—, —S($O_2$)—, —C(O)—, —CON(H)—, —NHC(O)—, —NH-CON(H)—, —$NHSO_2$—, —$SO_2N(H)$—, —C(O)—O—, —O—C(O)—, —$NHSO_2NH$—,

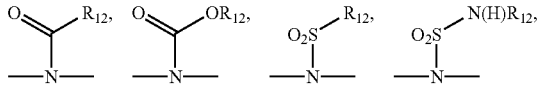

-continued

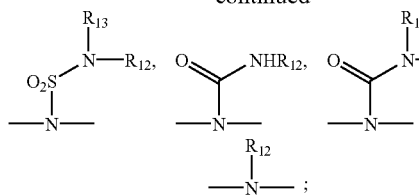

—$Q_1$— comprises $C_{1-6}$ alkylene, $C_{2-6}$ alkenylene, or $C_{2-6}$ alkynylene;

$R_3$ comprises
  a) hydrogen;
  b) —$C_{1-6}$ alkyl;
  c) —$C_{1-6}$ alkylaryl; or
  d) —$C_{1-6}$ alkoxyaryl;

$R_4$ comprises
  a) —$C_{1-6}$ alkylaryl;
  b) —$C_{1-6}$ alkoxyaryl; or
  c) -aryl;

$R_7, R_8, R_{12}$ and $R_{13}$ independently comprise hydrogen, $C_1$-$C_6$ alkyl, $C_1$-$C_6$ alkylaryl, or aryl; and wherein the aryl and/or alkyl group(s) in $R_1, R_2, R_3, R_4, R_5, R_6, R_7, R_8, R_9, R_{10}, R_{11}, R_{12}$, and $R_{13}$ may be optionally substituted 1-4 times with a substituent group, wherein said substituent group(s) or the term substituted refers to groups comprising:
  a) —H;
  b) —Y—$C_{1-6}$ alkyl;
     —Y-aryl;
     —Y—$C_{1-6}$ alkylaryl;
     —Y—$C_{1-6}$-alkyl-$NR_{14}R_{15}$;
     —Y—$C_{1-6}$-alkyl-W-$R_{16}$;
        wherein Y and W independently comprise —$CH_2$—, —O—, —N(H), —S—, $SO_2$—, —CON(H)—, —NHC(O)—, —NHCON(H), —$NHSO_2$—, —$SO_2N(H)$—, —C(O)—O—, —$NHSO_2NH$—, —O—CO—,

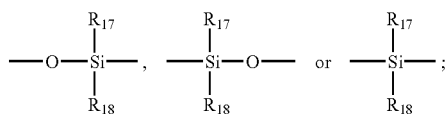

$R_{16}, R_{17}$, and $R_{18}$ comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or
  c) halogen, hydroxyl, cyano, carbamoyl, or carboxyl; and $R_{14}$ and $R_{15}$ independently comprise hydrogen, aryl, $C_1$-$C_6$ alkyl, or $C_1$-$C_6$ alkylaryl; and wherein $R_{14}$ and $R_{15}$ may be taken together to form a ring having the formula —$(CH_2)_o$-Z-$(CH_2)_p$— bonded to the nitrogen atom to which $R_{14}$ and $R_{15}$ are attached, and/or $R_7$ and $R_8$ may, independently, be taken together to form a ring having the formula —$(CH_2)_o$-Z-$(CH_2)_p$— bonded to the atoms to which $R_7$ and $R_8$ are attached, wherein o and p are, independently, 1, 2, 3, or 4; Z comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

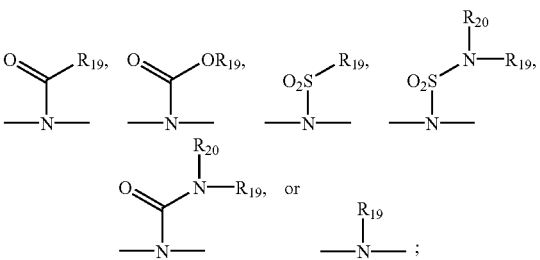

$R_{19}$ and $R_{20}$ independently comprise hydrogen, aryl, $C_1$-$C_6$ alkyl, or $C_1$-$C_6$ alkylaryl.

In a third aspect, the present invention provides compounds of formula (Ia):

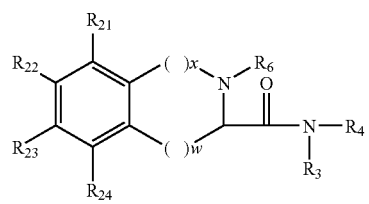

(Ia)

wherein, x and w are independently equal to 0, 1, or 2; provided that both x and w are not 0; wherein the values of 0, 1, and 2 comprise a direct bond, —$CH_2$—, and —$CH_2$—$CH_2$—, optionally substituted 1-4 times with a substituent group, wherein said substituent group(s) or the term substituted refers to groups comprising:
  a) —H;
  b) —Y—$C_{1-6}$ alkyl;
     —Y-aryl;
     —Y—$C_{1-6}$ alkylaryl;
     —Y—$C_{1-6}$-alkyl-W-$R_{16}$;
        wherein Y and W independently comprise —$CH_2$—, —O—, —N(H), —S—, $SO_2$—, —CON(H)—, —NHC(O)—, —NHCON(H)—, $NHSO_2$—, —$SO_2N(H)$—, —C(O)—O—, —$NHSO_2NH$—, —O—CO—,

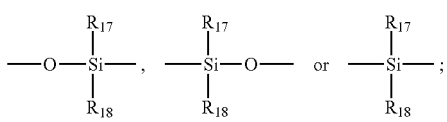

$R_{16}, R_{17}$, and $R_{18}$ comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or
  c) halogen, hydroxyl, cyano, carbamoyl, or carboxyl;

$G_1$ comprises a direct bond;
$G_2$ comprises

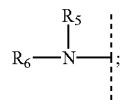

$R_1$ comprises H;
$R_3$ comprises
  a) hydrogen;
  b) —$C_{1-6}$ alkyl;
  c) —$C_{1-6}$ alkylaryl; or
  d) —$C_{1-6}$ alkoxyaryl;
$R_4$ comprises
  a) —$C_{1-6}$ alkylaryl;
  b) —$C_{1-6}$ alkoxyaryl; or
  c) -aryl;
$R_5$ and $R_2$ are taken together to form a ring of structure

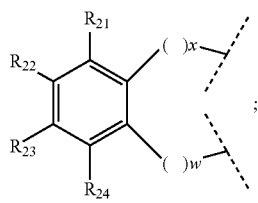

$R_6$ comprises
  a) —H;
  b) —$C_{1-6}$ alkyl;
  c) -aryl;
  d) —$C_{1-6}$ alkylaryl; or
  e) a group selected from —$C(O)R_{25}$, —$C(O)OR_{25}$, —$C(O)NR_{26}R_{25}$, —$S(O)_2R_{25}$, and —$S(O)_2NR_{26}R_{25}$; wherein $R_{25}$ and $R_{26}$ independently comprise —$C_{1-6}$ alkyl, aryl, or —$C_{1-6}$ alkylaryl;
wherein $R_{21}$, $R_{22}$, $R_{23}$ and $R_{24}$ independently comprise
  i) —H;
  ii) —$C_{1-6}$ alkyl;
  iii) -aryl;
  iv) —$C_{1-6}$ alkylaryl; or
  v) a group of the formula —U—$R_{27}$, wherein U is selected from —C(O)—, —C(O)O—, —O—, —S—, —S(O)—, —S(O)$_2$—, —$NR_{28}$—,
  wherein $R_{27}$ and $R_{28}$ independently comprise —H, -aryl, —$C_{1-6}$ alkyl, or —$C_{1-6}$ alkylaryl;
the aryl and/or alkyl group(s) in $R_3$, $R_4$, and $R_6$ may be optionally substituted 1-4 times with a substituent group, wherein said substituent group(s) or the term substituted refers to groups comprising:
  a) —H;
  b) —Y—$C_{1-6}$ alkyl;
    —Y-aryl;
    —Y—$C_{1-6}$ alkylaryl;
    —Y—$C_{1-6}$-alkyl-$NR_{14}R_{15}$;
    —Y—$C_{1-6}$-alkyl-W-$R_{16}$;
    wherein Y and W independently comprise —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

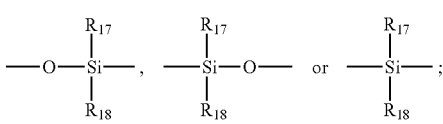

$R_{16}$, $R_{17}$, and $R_{18}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or
  c) halogen, hydroxyl, cyano, carbamoyl, or carboxyl; and
$R_{14}$ and $R_{15}$ independently comprise hydrogen, aryl, $C_1$-$C_6$ alkyl, or $C_1$-$C_6$ alkylaryl; and wherein
$R_{14}$ and $R_{15}$ may be taken together to form a ring having the formula —$(CH_2)_o$-Z-$(CH_2)_p$— bonded to the nitrogen atom to which $R_{14}$ and $R_{15}$ are attached, wherein o and p are, independently, 1, 2, 3, or 4; Z comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

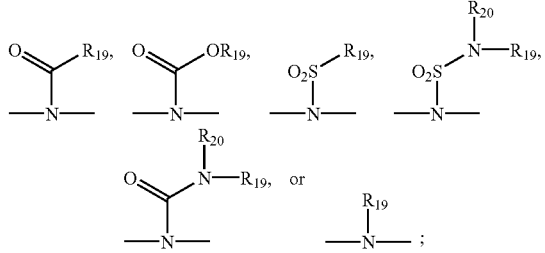

$R_{19}$ and $R_{20}$ independently comprise hydrogen, aryl, $C_1$-$C_6$ alkyl, or $C_1$-$C_6$ alkylaryl, or a pharmaceutically acceptable salt, solvate or prodrug thereof.

In a fourth aspect, the present invention provides compounds of the formula (Ib):

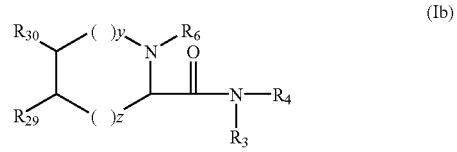

(Ib)

wherein,
y and z are, independently, an integer of from 0 to 3; wherein the values of 0, 1, and 2 comprise a direct bond, —$CH_2$—, —$CH_2$—$CH_2$—, and —$CH_2$—$CH_2$—$CH_2$—, respectively, optionally substituted 1-4 times with a substituent group, wherein said substituent group(s) or the term substituted refers to groups comprising:
  a) —H;
  b) —Y—$C_{1-6}$ alkyl;
    —Y-aryl;
    —Y—$C_{1-6}$ alkylaryl;
    —Y—$C_{1-6}$-alkyl-W-$R_{16}$;
    wherein Y and W independently comprise —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

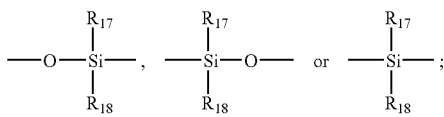

$R_{16}$, $R_{17}$ and $R_{18}$ comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or c) halogen, hydroxyl, cyano, carbamoyl, or carboxyl;

$G_1$ comprises a direct bond;

$G_2$ comprises

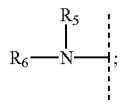

$R_1$ comprises H;

$R_3$ comprises
  a) hydrogen;
  b) —$C_{1-6}$ alkyl;
  c) —$C_{1-6}$ alkylaryl; or
  d) —$C_{1-6}$ alkoxyaryl;

$R_4$ comprises
  a) —$C_{1-6}$ alkylaryl;
  b) —$C_{1-6}$ alkoxyaryl; or
  c) -aryl;

$R_6$ comprises
  a) —H;
  b) —$C_{1-6}$ alkyl;
  c) -aryl;
  d) —$C_{1-6}$ alkylaryl; or
  e) a group selected from —C(O)$R_{25}$, —C(O)O$R_{25}$, —C(O)N$R_{26}R_{25}$, —S(O)$_2R_{25}$, and —S(O)$_2$N$R_{26}R_{25}$; wherein $R_{25}$ and $R_{26}$ independently comprise —$C_{1-6}$ alkyl, aryl, or —$C_{1-6}$ alkylaryl;

the aryl and/or alkyl group(s) in $R_3$, $R_4$, and $R_6$ may be optionally substituted 1-4 times with a substituent group, wherein said substituent group(s) or the term substituted refers to groups comprising:
  a) —H;
  b) —Y—$C_{1-6}$ alkyl;
     —Y-aryl;
     —Y—$C_{1-6}$ alkylaryl;
     —Y—$C_{1-6}$-alkyl-N$R_{14}R_{15}$;
     —Y—$C_{1-6}$-alkyl-W-$R_{16}$;
     wherein Y and W independently comprise —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

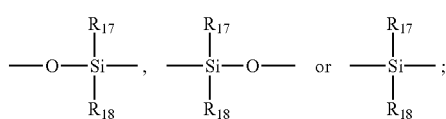

$R_{16}$, $R_{17}$, and $R_{18}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or c) halogen, hydroxyl, cyano, carbamoyl, or carboxyl; and $R_{14}$ and $R_{15}$ independently comprise hydrogen, aryl, $C_1$-$C_6$ alkyl, or $C_1$-$C_6$ alkylaryl; and wherein $R_{14}$ and $R_{15}$ may be taken together to form a ring having the formula —(CH$_2$)$_o$-Z-(CH$_2$)$_p$— bonded to the nitrogen atom to which $R_{14}$ and $R_{15}$ are attached, wherein o and p are, independently, 1, 2, 3, or 4; Z comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

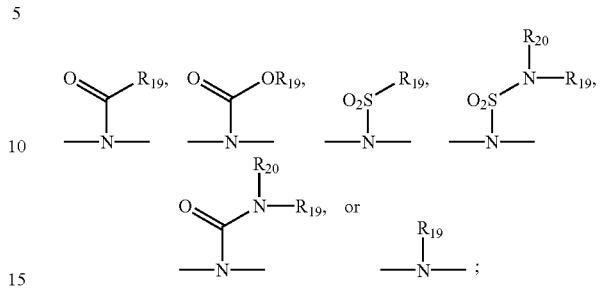

$R_{19}$ and $R_{20}$ independently comprise hydrogen, aryl, $C_1$-$C_6$ alkyl, or $C_1$-$C_6$ alkylaryl;

$R_5$ and $R_2$ are taken together to form a ring of structure

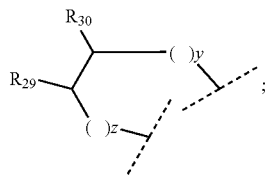

wherein $R_{29}$ and $R_{30}$ independently comprise
  a) —H
  b) —$C_{1-6}$ alkyl;
  c) -aryl;
  d) —$C_{1-6}$ alkylaryl;
  e) —C(O)—O—$C_{1-6}$ alkyl;
  f) —C(O)—O—$C_{1-6}$ alkylaryl;
  g) —C(O)—NH—$C_{1-6}$ alkyl;
  h) —C(O)—NH—$C_{1-6}$ alkylaryl;
  i) —SO$_2$—$C_{1-6}$ alkyl;
  j) —SO$_2$—$C_{1-6}$ alkylaryl;
  k) —SO$_2$-aryl;
  l) —SO$_2$—NH—$C_{1-6}$ alkyl;
  m) —SO$_2$—NH—$C_{1-6}$ alkylaryl;
  n) —C(O)—$C_{1-6}$ alkyl;
  o) —C(O)—$C_{1-6}$ alkylaryl; or
  p) a group of the formula —V—$R_{31}$,
     wherein V comprises group of the formula —C(O), —OC(O)—, —O—, —S—, —S(O)—, —S(O$_2$)—, —NH—, and —N($R_{32}$)—;
     wherein $R_{31}$ and $R_{32}$ independently comprise
       a) —H
       b) —$C_{1-6}$ alkyl;
       c) -aryl;
       d) —$C_{1-6}$ alkylaryl;
       e) —C(O)—O—$C_{1-6}$ alkyl;
       f) —C(O)—O—$C_{1-6}$ alkylaryl;
       g) —C(O)—NH—$C_{1-6}$ alkyl; —C(O)—NH—$C_{1-6}$ alkylaryl;
       h) —SO$_2$—$C_{1-6}$ alkyl;
       i) —SO$_2$—$C_{1-6}$ alkylaryl;
       j) —SO$_2$-aryl;
       k) —SO$_2$—NH—$C_{1-6}$ alkyl;
       l) —SO$_2$—NH—$C_{1-6}$ alkylaryl;
       m) —C(O)—$C_{1-6}$ alkyl; or
       n) —C(O)—$C_{1-6}$ alkylaryl;

wherein $R_{29}$, $R_{30}$, $R_{31}$, and $R_{32}$ may be optionally substituted 1-4 times with a substituent group, wherein said substituent group(s) or the term substituted refers to groups selected from the groups comprising:
a) —H;
b) -L-$C_{1-6}$ alkyl;
-L-aryl;
-L-$C_{1-6}$ alkylaryl;
-L-$C_{1-6}$-alkyl-$NR_{33}R_{34}$;
-L-$C_{1-6}$ alkyl-$Q_2$-$R_{35}$;
wherein L and $Q_2$ independently comprise —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

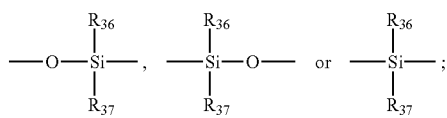

$R_{35}$, $R_{36}$ and $R_{37}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; and c) halogen, hydroxyl, cyano, carbamoyl, or carboxyl; and $R_{33}$ and $R_{34}$ independently comprise hydrogen, aryl, $C_1$-$C_6$ alkyl, or $C_1$-$C_6$ alkylaryl; and wherein $R_{33}$ and $R_{34}$ may be taken together to form a ring having the formula —$(CH_2)_e$-J-$(CH_2)_k$— bonded to the nitrogen atom to which $R_{33}$ and $R_{34}$ are attached, wherein e and k are, independently, 1, 2, 3, or 4; J comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

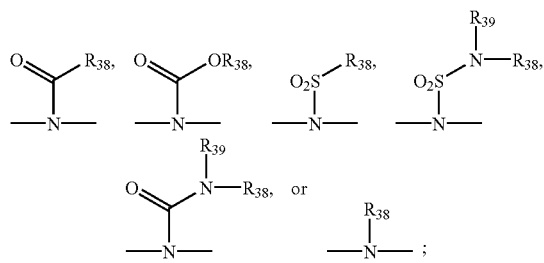

$R_{38}$ and $R_{39}$ independently comprise hydrogen, aryl, $C_1$-$C_6$ alkyl, or $C_1$-$C_6$ alkylaryl; or a pharmaceutically acceptable salt, solvate or prodrug thereof.

In a fifth aspect, the present invention provides compounds of formula (Ic):

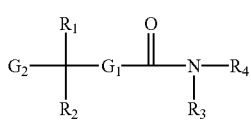

(Ic)

wherein,
$R_1$ comprises hydrogen or $C_{1-3}$ alkylaryl wherein the aryl is substituted with —Y—$C_{1-6}$ alkylaryl;

$R_2$ comprises $C_{1-3}$ alkylaryl wherein the aryl is substituted with —Y—$C_{1-6}$ alkylaryl;
wherein Y comprises —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

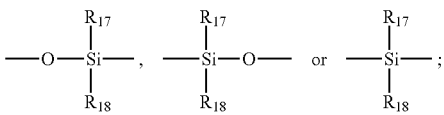

$R_{17}$, and $R_{18}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl;

$R_3$ is defined as in Formula (I);
$R_4$ is defined as in Formula (I);
$G_1$ is defined as in Formula (I); and
$G_2$ is defined as in Formula (I).

In a sixth aspect, the present invention provides compounds of formula (Id):

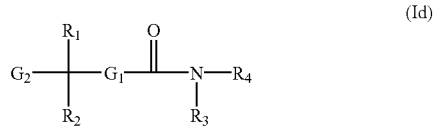

(Id)

wherein,
$R_1$ comprises hydrogen, or $C_{1-3}$ alkylaryl wherein the aryl is substituted with —Y—$C_{1-6}$ alkylaryl;

$R_2$ comprises $C_{1-3}$ alkylaryl wherein the aryl is substituted with —Y—$C_{1-6}$ alkylaryl;
wherein Y comprises —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

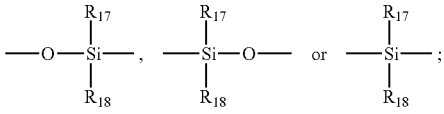

$R_{17}$, and $R_{18}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; and $R_3$ comprises hydrogen or -L-$C_{1-6}$-alkyl-N(alkyl)$_2$;

$R_4$ comprises -L-$C_{1-6}$-alkyl-N(alkyl)$_2$;
wherein L comprises —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

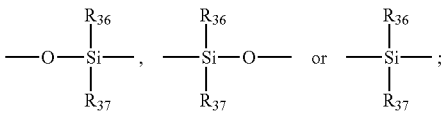

$R_{35}$, $R_{36}$, and $R_{37}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; and $G_1$ is defined as in the Formula (I); and
$G_2$ is defined as in the Formula (I).

In a seventh aspect, the present invention provides compounds of the formula (Ie):

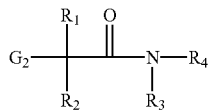

wherein,
$G_1$ comprises a direct bond;
$G_2$ comprises a group of the formula

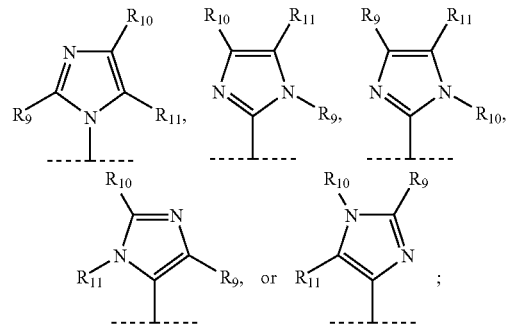

wherein
$R_9$, $R_{10}$, and $R_{11}$ may be hydrogen; or
$R_9$, $R_{10}$, and $R_{11}$ independently comprise
i) —$C_{1-6}$ alkyl;
ii) -aryl;
iii) —$C_{1-6}$ alkylaryl;
iv) —C(O)—O—$C_{1-6}$ alkyl;
v) —C(O)—O—$C_{1-6}$ alkylaryl;
vi) —C(O)—NH—$C_{1-6}$ alkyl;
vii) —C(O)—NH—$C_{1-6}$ alkylaryl;
viii) —$SO_2$—$C_{1-6}$ alkyl;
ix) —$SO_2$—$C_{1-6}$ alkylaryl;
X) —$SO_2$-aryl;
xi) —$SO_2$—NH—$C_{1-6}$ alkyl;
xii) —$SO_2$—NH—$C_{1-6}$ alkylaryl;
xiii) —C(O)—$C_{1-6}$ alkyl; or
xiv) —C(O)—$C_{1-6}$ alkylaryl; or $R_{10}$ and $R_{11}$ may be taken together to constitute a fused cycloalkyl, fused heterocyclyl, or fused aryl ring containing the atoms to which $R_{10}$ and $R_{11}$ are bonded;
$R_1$ comprises H;
$R_2$ comprises
a) —$C_{1-6}$ alkyl;
b) -aryl; or
c) —$C_{1-6}$ alkylaryl;
$R_3$ comprises
a) hydrogen;
b) —$C_{1-6}$ alkyl;
c) —$C_{1-6}$ alkylaryl; or
d) —$C_{1-6}$ alkoxyaryl;

$R_4$ comprises
a) —$C_{1-6}$ alkylaryl;
b) —$C_{1-6}$ alkoxyaryl; or
c) -aryl;

the aryl and/or alkyl group(s) in $R_2$, $R_3$, $R_4$, $R_9$, $R_{10}$, $R_{11}$ may be optionally substituted 1-4 times with a substituent group, wherein said substituent group(s) or the term substituted refers to groups comprising:
a) —H;
b) —Y—$C_{1-6}$ alkyl;
—Y-aryl;
—Y—$C_{1-6}$ alkylaryl;
—Y—$C_{1-6}$-alkyl-$NR_{14}R_{15}$;
—Y—$C_{1-6}$-alkyl-W-$R_{16}$;
wherein Y and W independently comprise —$CH_2$—, —O—, —N(H)—, —S—, $SO_2$—, —CON(H)—, —NHC(O)—, —NHCON(H), —$NHSO_2$—, —$SO_2N(H)$—, —C(O)—O—, —$NHSO_2NH$—, —O—CO—,

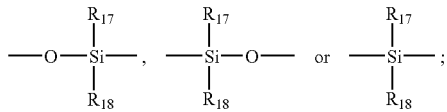

$R_{16}$, $R_{17}$, and $R_{18}$ independently comprise hydrogen, aryl, $C_1$-$C_6$ alkyl, $C_1$-$C_6$ alkylaryl, $C_1$-$C_6$ alkoxy, or $C_{1-6}$ alkoxyaryl; or
c) halogen, hydroxyl, cyano, carbamoyl, or carboxyl; and
$R_{14}$ and $R_{15}$ independently comprise hydrogen, aryl, $C_1$-$C_6$ alkyl, or $C_1$-$C_6$ alkylaryl; and wherein
$R_{14}$ and $R_{15}$ may be taken together to form a ring having the formula —$(CH_2)_o$-Z-$(CH_2)_p$— bonded to the nitrogen atom to which $R_{14}$ and $R_{15}$ are attached, wherein o and p are, independently, 1, 2, 3, or 4; Z comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

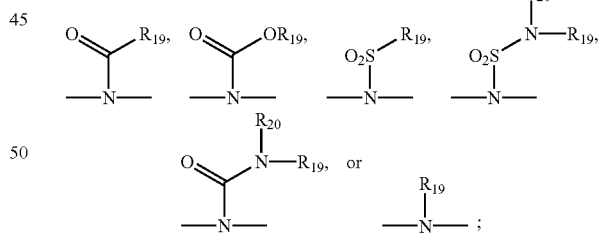

$R_{19}$ and $R_{20}$ independently comprise hydrogen, aryl, $C_1$-$C_6$ alkyl, or $C_1$-$C_6$ alkylaryl;

In an eighth aspect, the present invention provides compounds of the formula (If):

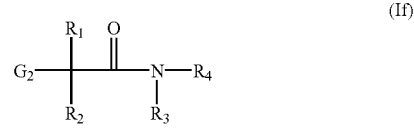

wherein,
$G_1$ comprises a direct bond;
$G_2$ comprises

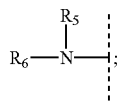

$R_1$ comprises H;
$R_2$ comprise a group of the formula

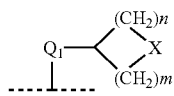

wherein m and n are independently selected from 1, 2, 3, or 4; X comprises a direct bond, $CH_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

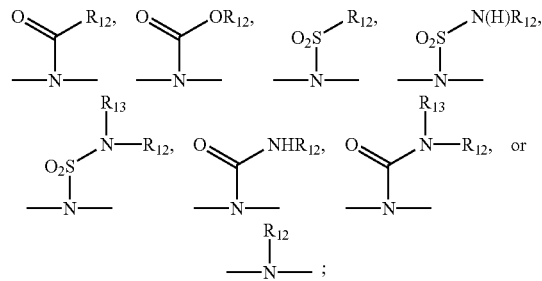

—$Q_1$— comprises $C_{1-6}$ alkylene, $C_{2-6}$ alkenylene, or $C_{2-6}$ alkynylene;

$R_{12}$ and $R_{13}$ independently comprise hydrogen, $C_1$-$C_6$ alkyl, $C_1$-$C_6$ alkylaryl, or aryl;

$R_3$ comprises
  a) hydrogen;
  b) —$C_{1-6}$ alkyl;
  c) —$C_{1-6}$ alkylaryl; or
  d) —$C_{1-6}$ alkoxyaryl;

$R_4$ comprises
  a) —$C_{1-6}$ alkylaryl;
  b) —$C_{1-6}$ alkoxyaryl; or
  c) -aryl;

$R_5$ and $R_6$ independently comprise
  a) —H;
  b) —$C_{1-6}$ alkyl;
  c) -aryl;
  d) —$C_{1-6}$ alkylaryl; or
  e) a group selected from —C(O)$R_{25}$, —C(O)O$R_{25}$, —C(O)N$R_{26}R_{25}$, —S(O)$_2R_{25}$, and —S(O)$_2$N$R_{26}R_{25}$; wherein $R_{25}$ and $R_{26}$ independently comprise —$C_{1-6}$ alkyl, aryl, or —$C_{1-6}$ alkylaryl;

the aryl and/or alkyl group(s) in $R_3$, $R_4$, $R_5$, $R_6$, $R_{12}$, and $R_{13}$ may be optionally substituted 1-4 times with a substituent group, wherein said substituent group(s) or the term substituted refers to groups comprising:
  a) —H;
  b) —Y—$C_{1-6}$ alkyl;

—Y-aryl;
—Y—C-$_{1-6}$ alkylaryl;
—Y—$C_{1-6}$-alkyl-N$R_{14}R_{15}$;
—Y—$C_{1-6}$-alkyl-W-$R_{16}$;
  wherein Y and W independently comprise —$CH_2$—, —O—, —N(H), —S—, $SO_2$—, —CON(H)—, —NHC(O)—, —NHCON(H)—, NHSO$_2$—, —SO$_2$N(H)—, —C(O)—O—, —NHSO$_2$NH—, —O—CO—,

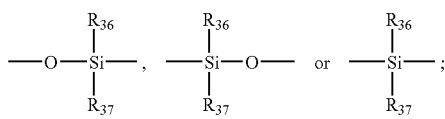

$R_{16}$, $R_{17}$, and $R_{18}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; or c) halogen, hydroxyl, cyano, carbamoyl, or carboxyl; and $R_{14}$ and $R_{15}$ independently comprise hydrogen, aryl, $C_1$-$C_6$ alkyl, or $C_1$-$C_6$ alkylaryl; and wherein
$R_{14}$ and $R_{15}$ may be taken together to form a ring having the formula —(CH$_2$)$_o$-Z-(CH$_2$)$_p$— bonded to the nitrogen atom to which $R_{14}$ and $R_{15}$ are attached, wherein o and p are, independently, 1, 2, 3, or 4; Z comprises a direct bond, —$CH_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

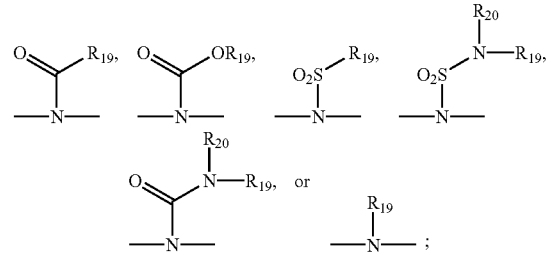

$R_{19}$ and $R_{20}$ independently comprise hydrogen, aryl, $C_1$-$C_6$ alkyl, or $C_1$-$C_6$ alkylaryl.

In the above described compounds, the various functional groups represented should be understood to have a point of attachment at the functional group having the hyphen. In other words, in the case of —$C_{1-6}$-alkylaryl, it should be understood that the point of attachment is the alkyl group; an example would be benzyl. In the case of a group such as —C(O)—NH—$C_{1-6}$-alkylaryl, the point of attachment is the carbonyl carbon.

In the above described compounds, the group "( )" with subscripts m, n, w, x, y, z indicate the presence of up to 2 or 3 methylene linkages. In other words, if m is 3, this represents a —$CH_2$—$CH_2$—$CH_2$—linkage. If m is zero, this represents a direct bond between the groups on either side, i.e. via a covalent bond.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

Compounds of the present invention which are currently preferred for their biological activity are listed by name below in Table 1.

TABLE 1

| Example | | Chemical Name |
|---|---|---|
| 1 | 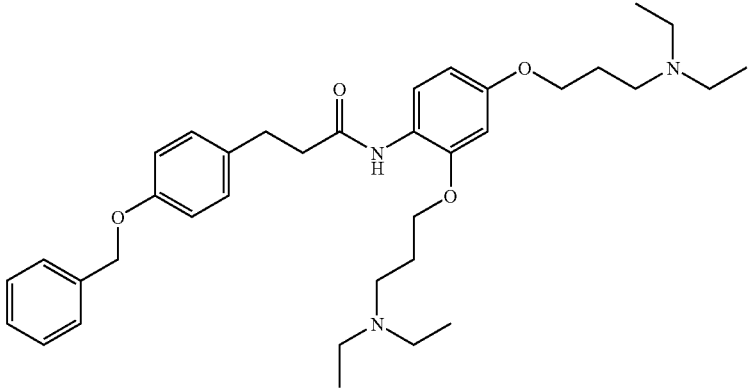 | 3-(4-Benzyloxyphenyl)propionic Acid 2,4-Di-(3-Diethylamino-1-propoxy)aniline Amide |
| 2 | 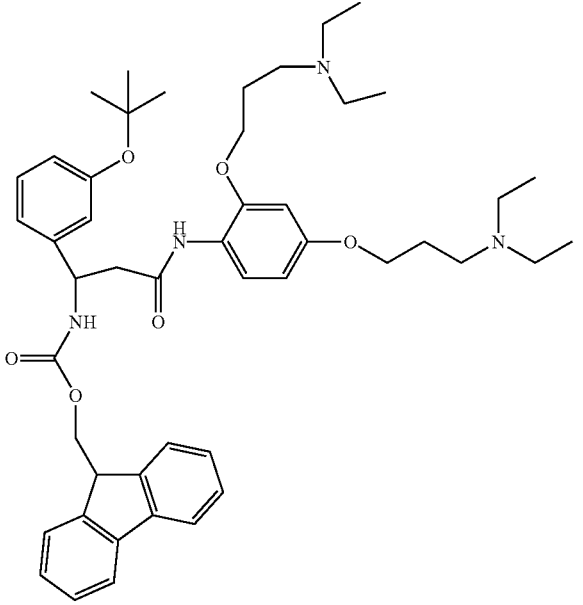 | 3-(3-Tert-butoxyphenyl)-3-(9-fluorenylmethoxycarbonylamino)propionic Acid 2,4-Di-(3-diethylaminopropoxy)aniline Amide |
| 3 | 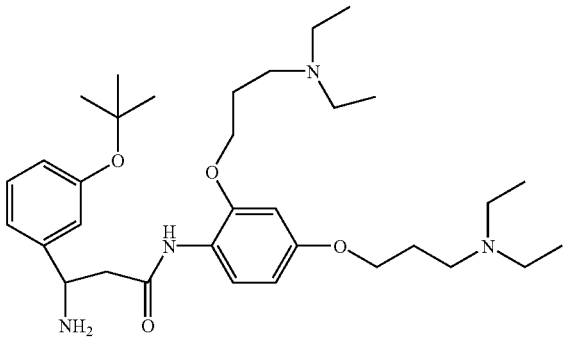 | 3-(3-Tert-butoxyphenyl)-3-aminopropionic Acid 2,4-Di-(3-diethylaminopropoxy)aniline Amide |

TABLE 1-continued

| Example | | Chemical Name |
|---|---|---|
| 4 | 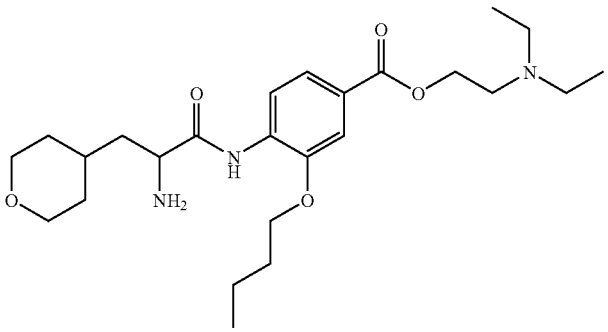 | 3-(4-Tetrahydropyranyl)-2-aminopropionic Acid 4-Diethylaminoethoxycarbonyl-2-butoxyaniline Amide Dihydrochloride |
| 5 | 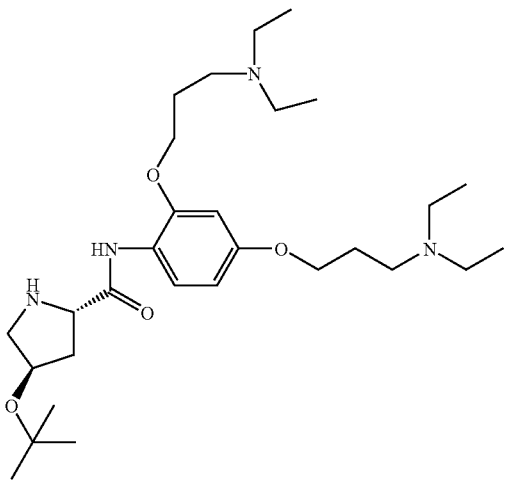 | (2S, 4R)-4-Tert-Butoxypyrrolidine-2-carboxylic acid 2,4-Di(3-diethylamino-1-propoxy)aniline Amide |
| 6 | 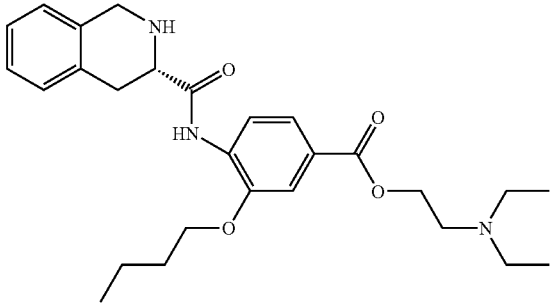 | (3S)-1,2,3,4-Tetrahydroisoquinoline-3-carboxylic Acid 4-Diethylaminoethoxycarbonyl-2-butoxyaniline Amide Dihydrochloride |
| 7 | 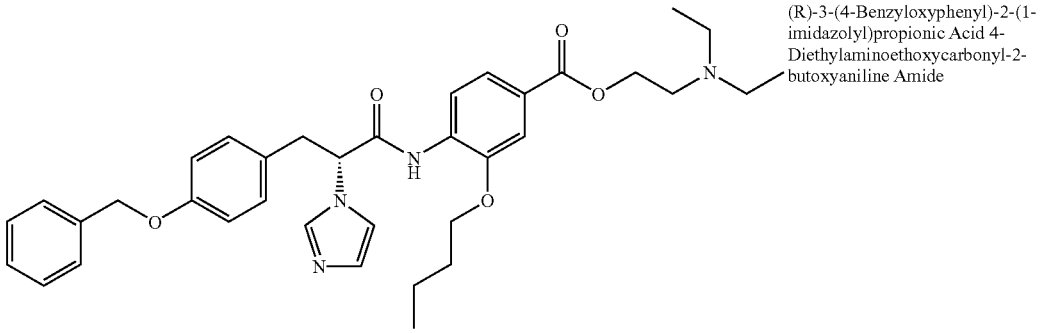 | (R)-3-(4-Benzyloxyphenyl)-2-(1-imidazolyl)propionic Acid 4-Diethylaminoethoxycarbonyl-2-butoxyaniline Amide |

TABLE 1-continued
| Example | | Chemical Name |
|---|---|---|
| 8 | 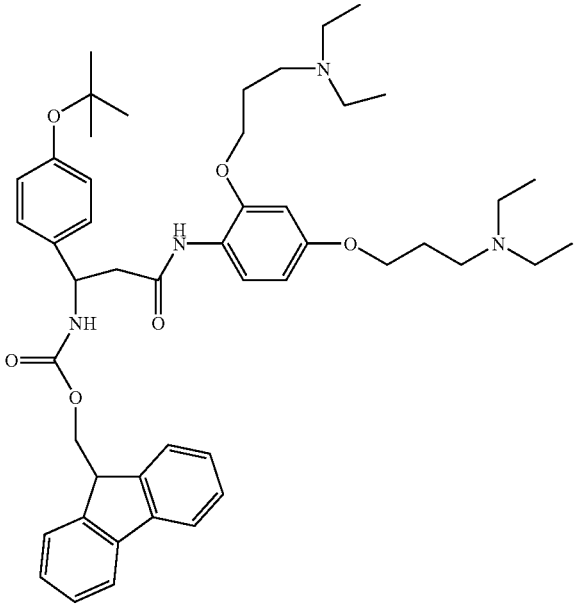 | 3-(4-Tert-butoxyphenyl)-3-(9-fluorenylmethoxycarbonylamino)propionic Acid 2,4-Di-(3-diethylaminopropoxy)aniline Amide |
| 9 | 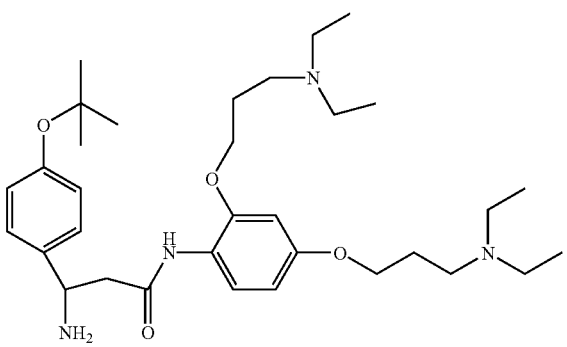 | 3-amino-3-(4-tert-butoxyphenyl)propionic Acid 2,4-Di-(3-diethylaminopropoxy)aniline Amide |
| 10 | 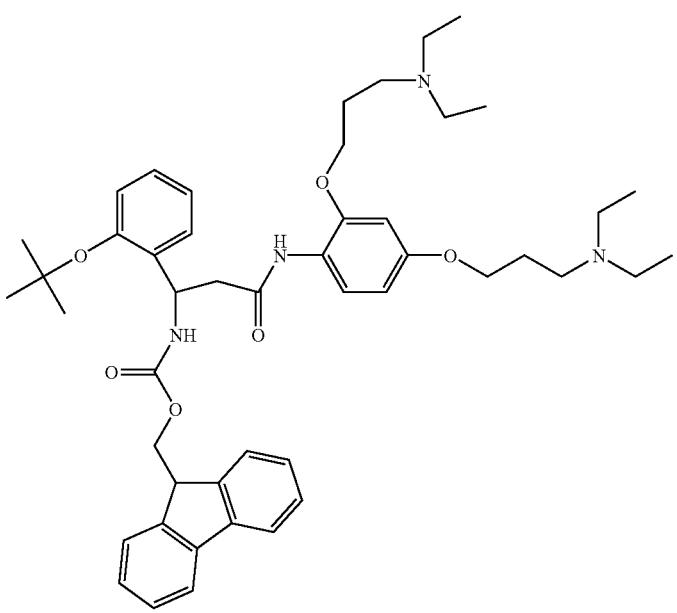 | 3-(9-fluorenylmethoxycarbonylamino)-3-(2-tert-butoxyphenyl)propionic Acid 2,4-Di-(3-diethylaminopropoxy)aniline Amide |

TABLE 1-continued

| Example | | Chemical Name |
|---|---|---|
| 11 | | 3-amino-3-(2-tert-butoxyphenyl)propionic Acid 2,4-Di-(3-diethylaminopropoxy)aniline Amide |
| 12 | | 3-Isopropylamino-3-(3-tert-butoxyphenyl)propionic Acid 2,4-Di-(3-diethylaminopropoxy)aniline Amide |
| 13 | | (2R)-2-tert-butoxycarbonylamino-3-[4-(benzyloxy)phenyl]propionic Acid 4-(3-diethylaminopropoxy)-N-benzylaniline Amide |

TABLE 1-continued

| Example | | Chemical Name |
|---|---|---|
| 14 | 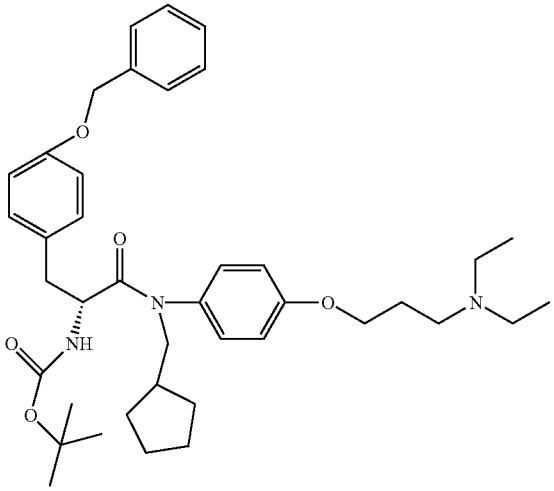 | (2R)-2-tert-butoxycarbonylamino-3-[4-(benzyloxy)phenyl]propionic Acid 4-(3-diethylaminopropoxy)-N-cyclopentylmethylaniline Amide |
| 15 | 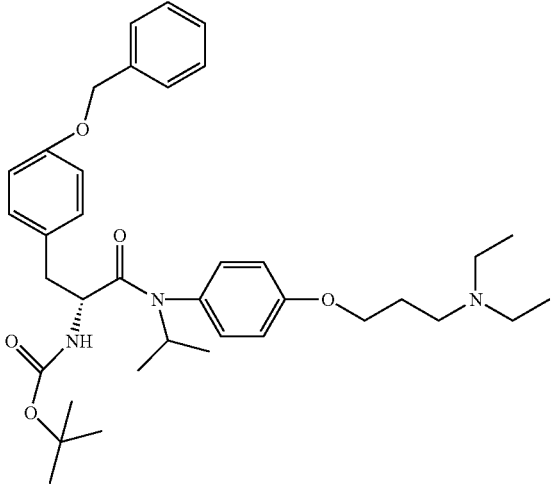 | (2R)-2-tert-butoxycarbonylamino-3-[4-(benzyloxy)phenyl]propionic Acid 4-(3-diethylaminopropoxy)-N-isopropylaniline Amide |
| 16 | 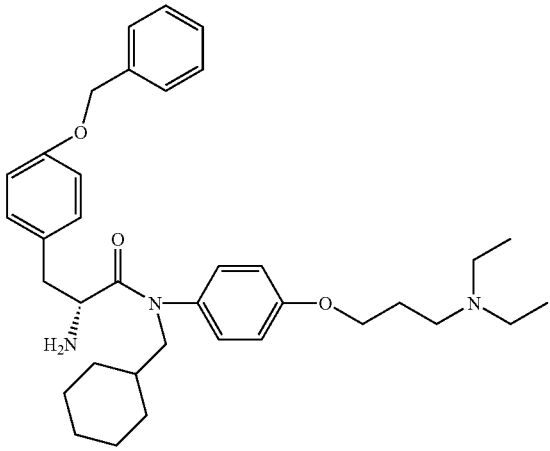 | (2R)-2-amino-3-[4-(benzyloxy)phenyl]propionic Acid 4-(3-diethylaminopropoxy)-N-cyclohexylmethylaniline Amide |

TABLE 1-continued

| Example | | Chemical Name |
|---|---|---|
| 17 | 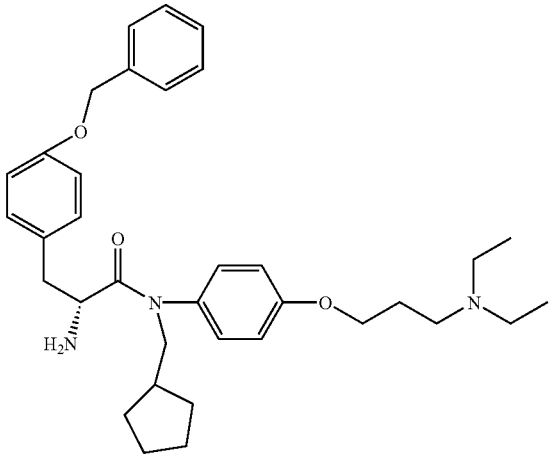 | (2R)-2-amino-3-[4-(benzyloxy)phenyl]propionic Acid 4-(3-diethylaminopropoxy)-N-cyclopentylmethylaniline Amide |
| 18 | 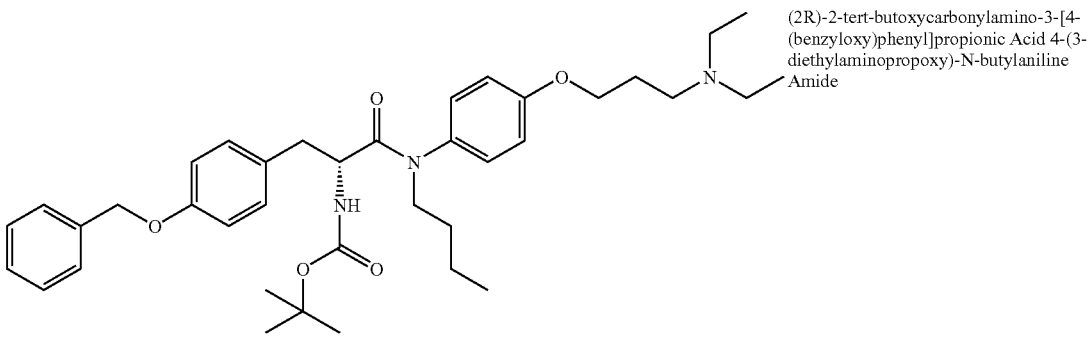 | (2R)-2-tert-butoxycarbonylamino-3-[4-(benzyloxy)phenyl]propionic Acid 4-(3-diethylaminopropoxy)-N-butylaniline Amide |
| 19 | 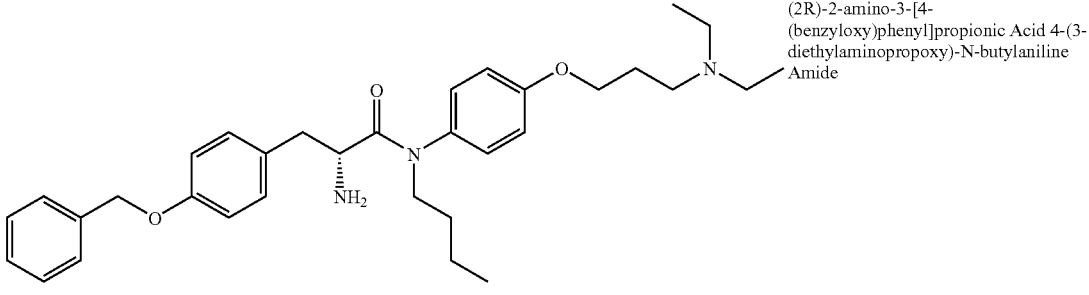 | (2R)-2-amino-3-[4-(benzyloxy)phenyl]propionic Acid 4-(3-diethylaminopropoxy)-N-butylaniline Amide |
| 20 | 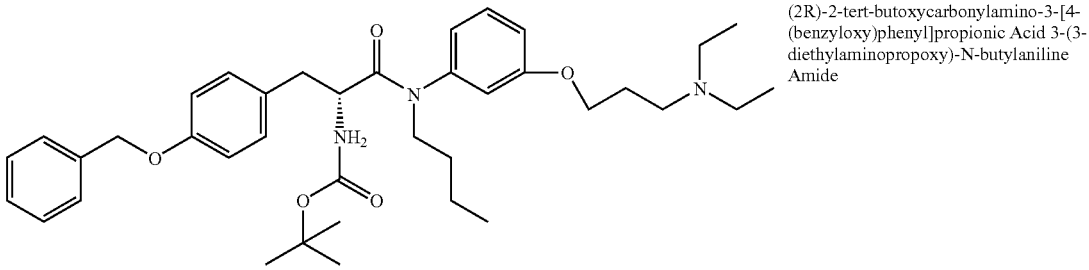 | (2R)-2-tert-butoxycarbonylamino-3-[4-(benzyloxy)phenyl]propionic Acid 3-(3-diethylaminopropoxy)-N-butylaniline Amide |

TABLE 1-continued

| Example | | Chemical Name |
|---|---|---|
| 21 | 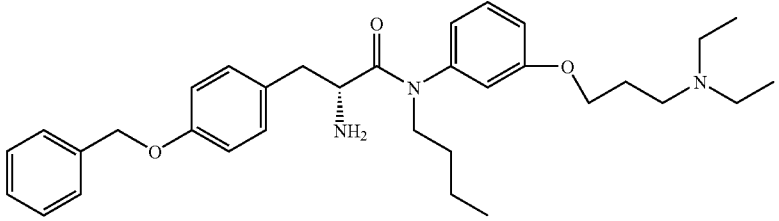 | (2R)-2-amino-3-[4-(benzyloxy)phenyl]propionic Acid 3-(3-diethylaminopropoxy)-N-butylaniline Amide |
| 22 | 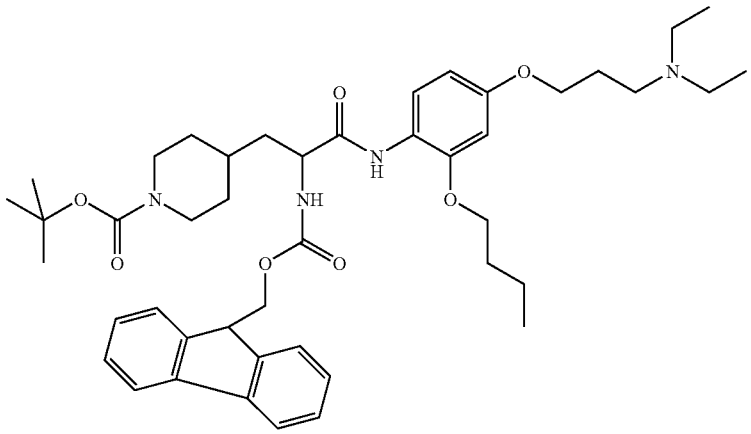 | 3-(1-Tert-butoxycarbonylpiperidin-4-yl)-2-(9-fluorenylmethoxycarbonylamino)propionic Acid 4-Diethylaminopropoxy-2-butoxyaniline Amide |
| 23 | 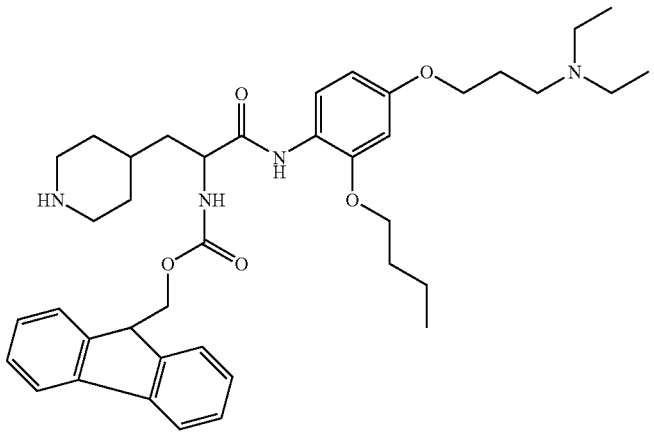 | 3-(Piperidin-4-yl)-2-(9-fluorenylmethoxycarbonylamino)propionic Acid 4-Diethylaminopropoxy-2-butoxyaniline Amide |
| 24 | 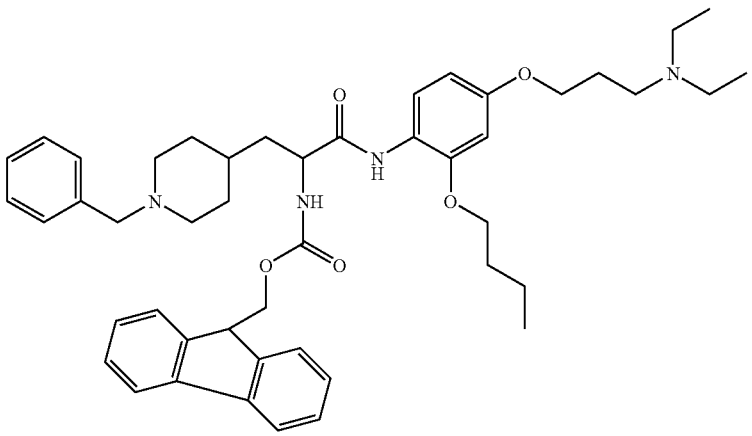 | 3-(1-Benzylpiperidin-4-yl)-2-(9-fluorenylmethoxycarbonylamino)propionic Acid 4-Diethylaminopropoxy-2-butoxyaniline Amide |

TABLE 1-continued

| Example | | Chemical Name |
|---|---|---|
| 25 | 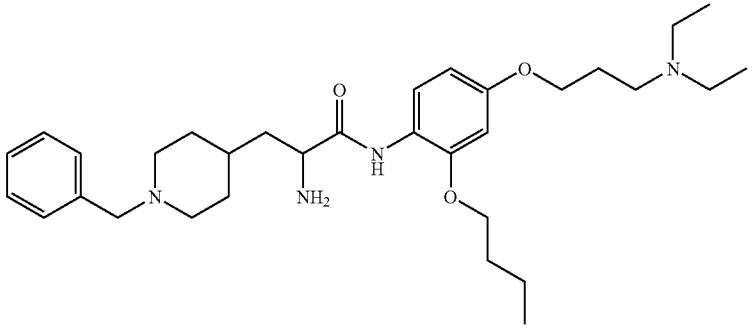 | 3-(1-Benzylpiperidin-4-yl)-2-aminopropionic Acid 4-Diethylaminopropoxy-2-butoxyaniline Amide |
| 26 | 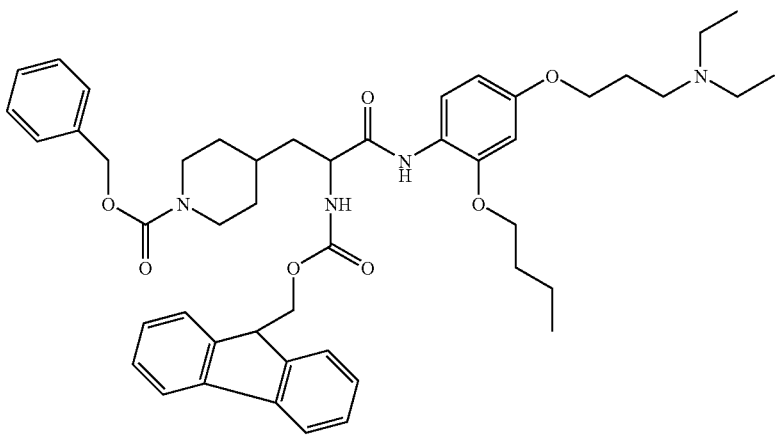 | 3-(1-Benzyloxycarbonylpiperidin-4-yl)-2-(9-fluorenylmethoxycarbonyamino)propionic Acid 4-Diethylaminopropoxy-2-butoxyaniline Amide |
| 27 | 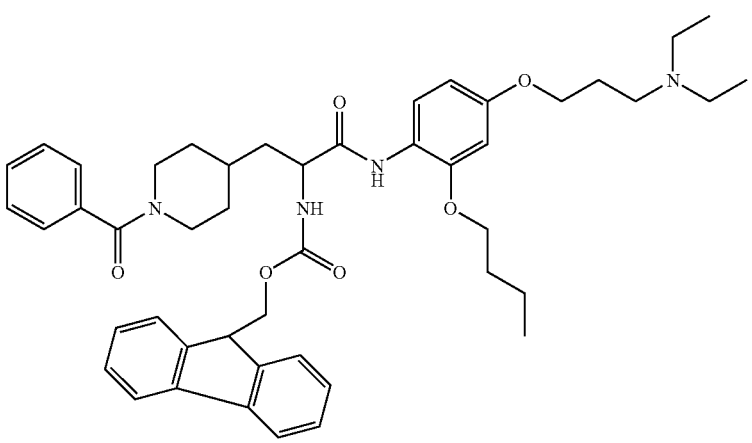 | 3-(1-Benzoylpiperidin-4-yl)-2-(9-fluorenylmethoxycarbonylamino)propionic Acid 4-Diethylaminopropoxy-2-butoxyaniline Amide |

TABLE 1-continued

| Example | | Chemical Name |
|---|---|---|
| 28 | 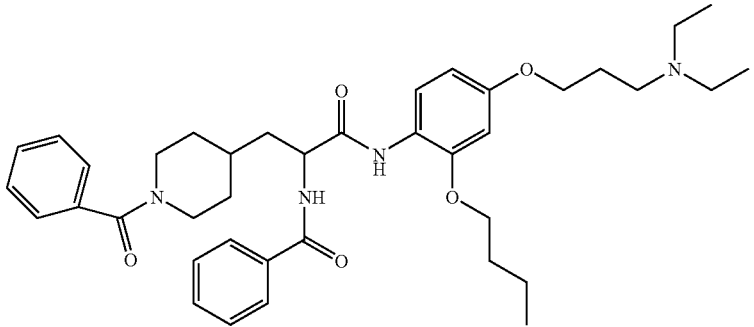 | 3-(1-Benzoylpiperidin-4-yl)-2-benzoylaminopropionic Acid 4-Diethylaminopropoxy-2-butoxyaniline Amide |
| 29 | 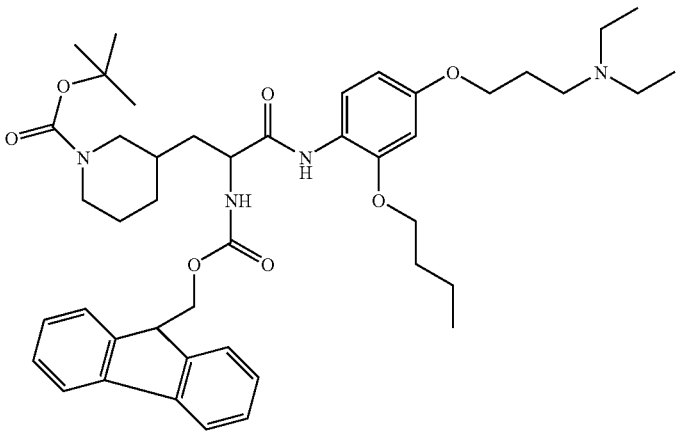 | 3-(Tert-butoxycarbonylpiperidin-3-yl)-2-(9-fluorenylmethoxycarbonylamino)propionic Acid 4-Diethylaminopropoxy-2-butoxyaniline Amide |
| 30 | 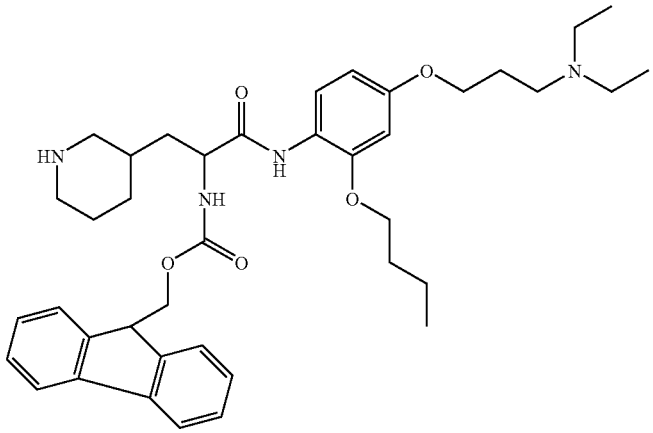 | 3-(Piperidin-3-yl)-2-(9-fluorenylmethoxycarbonylamino)propionic Acid 4-Diethylaminopropoxy-2-butoxyaniline Amide |

In another aspect, the present invention comprises a pharmaceutical composition comprising the compounds of the present invention, and one or more pharmaceutically acceptable carriers, excipients, or diluents.

In an embodiment, the pharmaceutical composition is in the form of an oral dosage or parenteral dosage unit. Preferably, a compound of the present invention is administered as a dose in a range from about 0.01 to 500 mg/kg of body weight per day. More preferably, the compound is administered as a dose in a range from about 0.1 to 200 mg/kg of body weight per day. Even more preferably, the compound is administered as a dose in a range from about 0.1 to 100 mg/kg of body weight per day.

In an embodiment, the pharmaceutical composition further comprises one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, anti psychotics, anti depressants, and anticonvulsants.

In another aspect, the present invention comprises a method for the inhibition of the interaction of RAGE with its physiological ligands, which comprises administering to a subject in need thereof, at least one compound of the present invention.

In an embodiment, the ligand(s) is(are) selected from advanced glycated end products (AGEs), S100/calgranulin/EN-RAGE, β-amyloid and amphoterin.

In yet another aspect, the present invention comprises methods for treating a disease state selected from the group consisting of acute and chronic inflammation, symptoms of diabetes, vascular permeability, nephropathy, atherosclerosis, retinopathy, Alzheimer's disease, erectile dysfunction, and tumor invasion and/or metastasis, which comprises administering to a subject in need thereof a therapeutically effective amount of at least one compound of the present invention.

In yet another aspect, the present invention comprises methods for prevention and/or treatment of RAGE mediated human diseases comprising administration to a human in need thereof a therapeutically effective amount of a compound of Formula (I) as claimed in claim 1, wherein a therapeutically effective amount comprises sufficient compound to at least partially inhibit the binding of a ligand to the RAGE receptor.

In an embodiment, the method includes administering to a subject in need thereof at least one adjuvant and/or additional therapeutic agent(s). Preferably, the therapeutic agents are selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Also preferably, the RAGE mediated human disease comprise acute and/or chronic inflammation, abnormal vascular permeability, nephropathy, atherosclerosis, retinopathy, Alzheimees disease, erectile dysfunction, tumor invasion and/or metastasis.

In the compounds of the present invention, the various functional groups represented should be understood to have a point of attachment at the functional group having the hyphen. In other words, in the case of —$C_{1-6}$ alkylaryl, it should be understood that the point of attachment is the alkyl group; an example would be benzyl. In the case of a group such as —C(O)—NH—$C_{1-6}$ alkylaryl, the point of attachment is the carbonyl carbon.

As used herein, the term "alkyl" refers to a straight or branched chain hydrocarbon having the number of specified carbon atoms. Examples of "alkyl" as used herein include, but are not limited to, methyl, n-butyl, n-pentyl, isobutyl, and isopropyl, and the like.

As used herein, the term "alkylene" refers to a straight or branched chain divalent hydrocarbon radical having the specified number of carbon atoms. Examples of "alkylene" as used herein include, but are not limited to, methylene, ethylene, and the like.

As used herein, the term "alkenylene" refers to a straight or branched chain divalent hydrocarbon radical having the specified number of carbon atoms and one or more carbon-carbon double bonds. Examples of "alkenylene" as used herein include, but are not limited to, ethene-1,2-diyl, propene-1,3-diyl, methylene-1,1-diyl, and the like.

As used herein, the term "alkynylene" refers to a straight or branched chain divalent hydrocarbon radical having the specified number of carbon atoms and one or more carbon-carbon triple bonds. Examples of "alkynylene" as used herein include, but are not limited to, ethyne-1,2-diyl, propyne-1,3-diyl, and the like.

As used herein, the term "aryl" refers to a five- to seven-membered aromatic ring, or to an optionally substituted benzene ring system, optionally containing one or more nitrogen, oxygen, or sulfur heteroatoms, where N-oxides and sulfur monoxides and sulfur dioxides are permissible substitutions. Such a ring may be fused to one or more five- to seven-membered aromatic rings optionally containing one or more nitrogen, oxygen, or sulfur heteroatoms. Preferred aryl groups include phenyl, biphenyl, 2-naphthyl, 1-naphthyl, phenanthryl, 1-anthracenyl, pyridyl, furyl, furanyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, benzindoyl, pyrazolyl, isoindolyl, purinyl, carbazolyl, isoxazolyl, thiazolyl, oxazolyl, benzothiazolyl, benzoxazolyl, and the like. In this regard, especially preferred aryl groups include phenyl, 2-naphthyl, 1-naphthyl, biphenyl, and like ring systems optionally substituted by tert-butyloxy, benzyloxy, n-butyloxy, ispropyloxy, and phenoxy.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the chemical structure terms "contain" or "containing" refer to inline substitutions at any position along the above defined substituent at one or more of any of O, S, SO, $SO_2$, N, or N-alkyl, including, for example, —$CH_2O$—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of described above) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acyamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I): for example, the lactam formed by a carboxylic group in $R_2$ and an amine in $R_4$, and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like. The term "pharmacologically effective amount" shall mean that amount of a drug or pharmaceutical agent that will elicit the biological or medical response of a tissue, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl substituents shall be recognized as being functionally equivalent to those having one or more degrees of unsaturation. Designated numbers of carbon atoms (e.g. $C_{1-6}$) shall refer independently to the number of carbon atoms in an alkyl moiety or to the alkyl portion of a larger substituent in which the term "alkyl" appears as its prefix root. Similarly, the term "$C_2$-$C_8$ alkenyl" and "$C_2$-$C_8$ alkynyl" refer to groups having from 2 to 8 carbon atoms and at least one carbon-carbon double bond or carbon-carbon triple bond, respectively.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —SO$_2$NH$_2$.

As used herein, the term "carbamoyl" shall refer to the substituent —C(O)NH$_2$.

The present invention also provides a method for the synthesis of compounds useful as intermediates in the preparation of compounds of Formula (I) along with methods for the preparation of compounds of Formula (I).

A suitably protected alpha-amino acid (1), where PG is an amine protecting group such as tert-butoxycarbonyl, is treated with an amine in the presence of a coupling reagent such as but not limited to diisopropyl carbodiimide (DIC) to form the amide (2).

The α-amino group in (2) is then deprotected, employing a strong acid such as hydrogen chloride for the case where PG is tertbutoxycarbonyl, to afford the free NH compound (3) either as the free base or as a salt (Scheme 1). Where there is no amino proptecting group, treatment of acid (4) affords the amide (5).

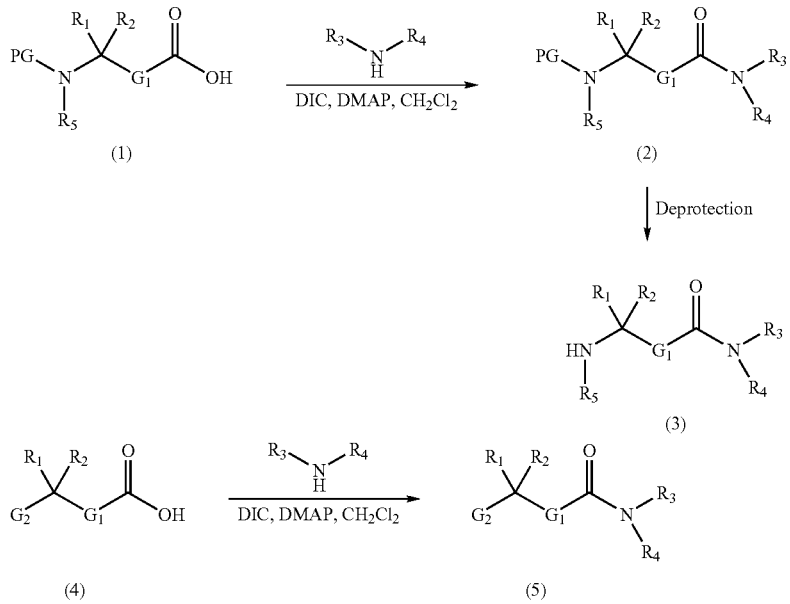

Scheme 1

To further derivatize the amino group of compound (6), a free amino compound, or the suitable salt thereof may be treated with an aldehyde or ketone $R_{40}C(O)R_{41}$ in the presence of a reducing agent such as sodium cyanoborohydride or sodium triacetoxyborohydride to afford compound (7), where $R_{40}$ and $R_{41}$ are defined such that $R_5$ in (7) conforms to the specifications for Formula (I). Alternately, the amine compound (6) may be treated with tertiary amine base such as DIEA and a molar equvalent amount (or slight excess) of an alkylating agent of general structure $R_5$-$Q_3$, where $Q_3$ is is a nucleofugal group such as bromine, to form the secondary amine compound (7) (Scheme 2). Amine (6) may be treated with a tertiary amine base such as triethylamine and 2 molar equivalents (or slight excess) of an alkylating agent of general structure R$_5$-Q$_3$, where Q$_3$ is is a nucleofugal group such as bromine, to form the amine compound (8).

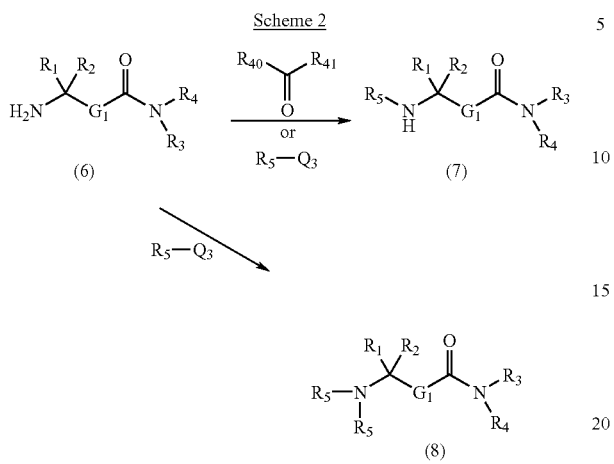

To further derivatize the amino group of compound (3), the free amino compound, or the suitable salt thereof may be treated with a sulfonyl chloride such as benzenesulfonyl chloride to form the sulfonamide (10) (Scheme 3), where R$_{43}$ is C$_{1-6}$ alkyl, C$_{1-6}$ alkylaryl, or aryl. Alternately, an amine R$_{44}$—NH$_2$ may be treated with sulfuryl chloride and the intermediate then treated with (3) to afford the sulfonylurea (8) where R$_{45}$ is —NH—C$_{1-6}$ alkyl or —NH—C$_{1-6}$ alkylaryl.

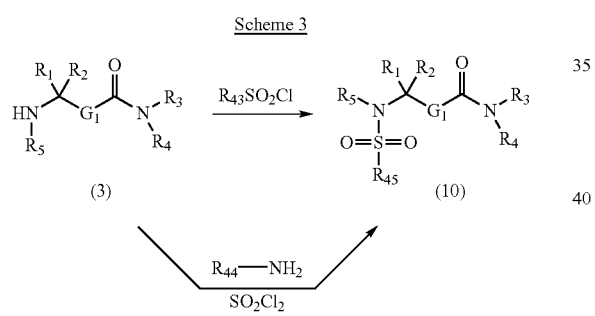

To further derivatize the amino group of compound (3), the free amino compound, or the suitable salt thereof may be treated with an isocyanate R$_{46}$NCO in the presence or absence of a tertiary amine base such as TEA to form the urea (11) (Scheme 4), where R$_{46}$ is —C$_{1-6}$ alkyl or —C$_{1-6}$ alkylaryl and A is NH. Alternately, compound (3) may be treated with R$_{46}$O—C(O)Cl and a tertiary amine base such as TEA to afford urea (11) where R$_{46}$ is —C$_{1-6}$ alkyl or —C$_{1-6}$ alkylaryl and A is O.

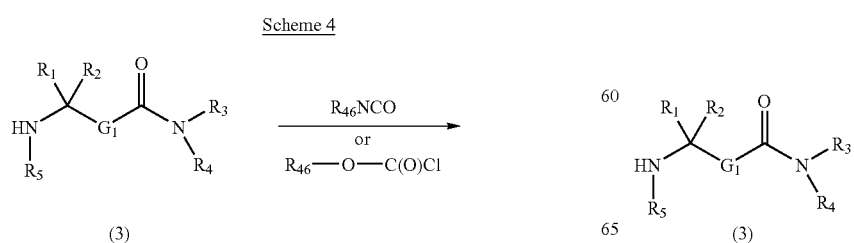

-continued

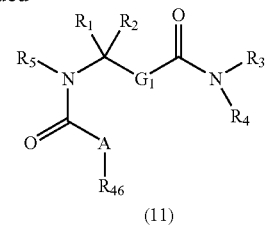

Compound (12) may be treated with triphenyl phosphine, either duisopropyl azodicarboxylate (DIAD) or diethyl azodicarboxylate (DEAD) and an alcohol R$_{47}$—OH to form the compound (13) (Scheme 5), after removal of the protecting group PG. R$_{47}$ is —C$_{1-6}$ alkyl, —C$_{1-6}$ alkylaryl, —C$_{1-6}$ alkyl-OSi(C$_{1-6}$ alkyl)$_3$, —C$_{1-6}$ alkyl-OSi(C$_{1-6}$ alkylaryl)$_3$, or —C$_{1-6}$ alkyl-NR$_{14}$R$_{15}$ (provided that neither R$_{14}$ nor R$_{15}$ are hydrogen). PG may be, for example, tert-butoxycarbonyl, benzyloxycarbonyl, and the like.

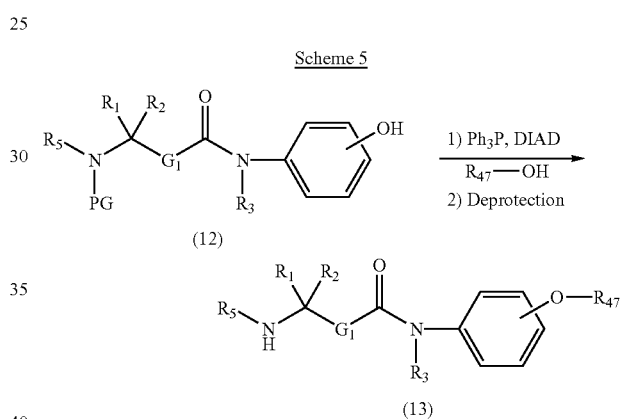

Compound (3) or a suitable salt thereof may be treated with a acid anhydride (R$_{48}$—CO)$_2$O and a base such as TEA in the presence or absence of pyridine or DMAP to afford compound (14) (Scheme 6). The substituent R$_{48}$ may be chosen such that the group R$_{48}$—C(O)— is as specified for R$_6$ in Formula (I). Alternately, compound (3) may be treated with the acid chloride R$_{48}$—COCl and an tertiary amine base such as TEA in the presence or absence of pyridine or DMAP to afford compound (14). Alternately, compound (3) may be treated with the carboxylic acid R$_{48}$—CO$_2$H and a carbodiimide reagent such as EDC, DIC, or DCC in the presence or absence of HOBt to provide compound (14).

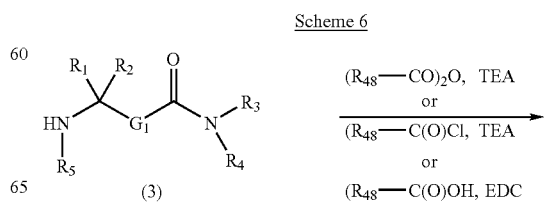

Compound (3) or a suitable salt thereof may be treated (Scheme 7) with an activated amidine reagent such as N,N'-bis-BOC-1-guanylpyrazole or 3,5-dimethylpyrazole-1-carboxamidine nitrate in the presence of a tertiary organic base such as TEA to generate the guanidine compound (15). Guanidine substituent protecting groups may be removed. For example, where N,N'-bis-BOC-1-guanylpyrazole is employed, the BOC groups of the adduct may be removed with a strong acid such as hydrogen chloride to afford the free guanidine compound (15), where $R_7$ and $R_8$ are as defined for Formula (I).

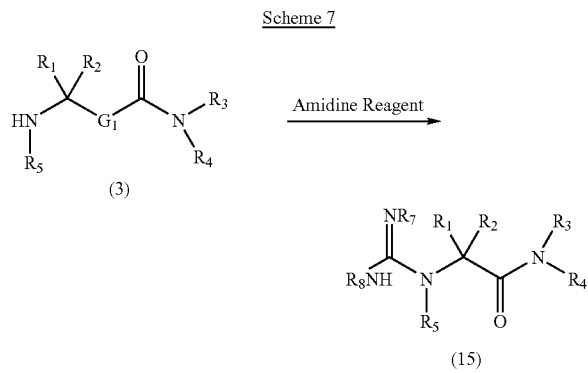

In the above schemes, "PG" represents an amino protecting group. The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups (PG as used herein) such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The MS was a Micromass ZMD instrument. All data was obtained in the positive mode unless otherwise noted. $^1$H NMR data was obtained on a Varian 300 MHz spectrometer.

Abbreviations used in the Examples are as follows:

| | |
|---|---|
| APCI = | atmospheric pressure chemical ionization |
| BOC = | tert-butoxycarbonyl |
| BOP = | (1-benzotriazolyloxy)tris(dimethylamino)phosphonium hexafluorophosphate |
| d = | day |
| DIAD = | diisopropyl azodicarboxylate |
| DCC = | dicyclohexylcarbodiimide |
| DCM = | dichloromethane |
| DIEA = | diisopropylethylamine |
| DMF = | N,N-dimethylformamide |
| DMPU = | 1,3-dimethypropylene urea |
| DMSO = | dimethylsulfoxide |
| EDC = | 1-ethyl-3-(3-dimethylaminopropyl)-carbodiimide hydrochloride |
| EDTA = | ethylenediamine tetraacetic acid |
| ELISA = | enzyme-linked immunosorbent assay |
| ESI = | electrospray ionization |
| ether = | diethyl ether |
| EtOAc = | ethyl acetate |
| FBS = | fetal bovine serum |
| g = | gram |
| h = | hour |
| HBTU = | O-benzotriazol-1-yl-N,N,N',N'-tetramethyluronium hexafluorophosphate |
| HMPA = | hexamethylphosphoric triamide |
| HOBt = | 1-hydroxybenzotriazole |
| Hz = | hertz |
| i.v. = | intravenous |
| kD = | kiloDalton |
| L = | liter |
| LAH = | lithium aluminum hydride |
| LDA = | lithium diisopropylamide |
| LPS = | lipopolysaccharide |
| M = | molar |
| m/z = | mass to charge ratio |
| mbar = | millibar |

-continued

```
    MeOH = methanol
      mg = milligram
     min = minute
      mL = milliliter
      mM = millimolar
    mmol = millimole
     mol = mole
      mp = melting point
      MS = mass spectrometry
       N = normal
     NMM = N-methylmorpholine, 4-methylmorpholine
     NMR = nuclear magnetic resonance spectroscopy
    p.o. = per oral
     PBS = phosphate buffered saline solution
     PMA = phorbol myristate acetate
     ppm = parts per million
     psi = pounds per square inch
     R_f = relative TLC mobility
      rt = room temperature
    s.c. = subcutaneous
     SPA = scintillation proximity assay
     TEA = triethylamine
     TFA = trifluoroacetic acid
     THF = tetrahydrofuran
     THP = tetrahydropyranyl
     TLC = thin layer chromatography
     T_r = retention time
```

The following compounds were synthesized according to the Schemes.

General Procedure A; Synthesis of 2,4-Dialkoxyanilines

Step 1; To a solution of 2,4-difluoronitroaromatic compound (1 eq) in THF (0.1-0.5 M), an alcohol (2.2 eq) was added and the reaction mixture is cooled to 0° C. Base (NaH, potassium tert-butoxide) (>2.2 eq) is added portionwise at 0° C. The reaction mixture is warmed up and allowed to reflux for 24 h. The reaction mixture is then cooled to room temperature, treated with solid ammonium chloride and stirred for 10 min. The solution is filtered off, concentrated in vacuo and purified by silica gel column chromatography to afford the 2,4-dialkoxynitroaromatic compound. Alternately, the reaction mixture may be cooled to rt, quenched with cold water, and extracted with EtOAc. Drying and concentration provides the crude nitroaromatic, which may be used without further purification or subjected to silica gel chromatography and then employed in the next step.

Step 2; The 2,4-dialkoxynitroaromatic compound is dissolved in ethanol (0.05-0.5 M) and treated with 4M HCl/dioxane (1-1.5 eq) followed by $SnCl_2 2H_2O$ (5-10 eq). The resulting reaction mixture is then refluxed under nitrogen overnight. After the reaction is complete, solid sodium bicarbonate is added till the pH of the reaction mixture is basic. The mixture is filtered, concentrated and dried in vacuo to provide the 2,4-dialkoxyaniline.

General Procedure B; Synthesis of 2,4-Dialkoxyanilines

Step 1; To a stirred solution of 3-fluoro-4-nitrophenol (1 eq 4 mmol) in DMF (60.1-0.5 M mL) at room temperature solid $K_2CO_3$ (2 eq 8 mmol) is added. An alkyl halide or mesylate (prepared from the corresponding alcohol and mesyl chloride) (1.1 eq 4.4 mmol) is added to the reaction mixture and heated to 80° C. until the reaction is complete as indicated by TLC or HPLC. After cooling to rt, the reaction mixture is poured into ethyl acetate (40 ml) and washed with water (2×20 ml) and brine (30 ml). The organic layer was dried over magnesium sulfate and after removal of the drying agent, the solvent was removed under vacuum to afford the desired product. The crude product may be used for further transformation without any purification or after purifying using silica gel column chromatography.

Step 2; To a stirred solution of 2-fluoro-4-alkoxynitrobenzene (1 eq 2 mmol) obtained above, an alcohol (1.2 eq) was added and the reaction mixture is cooled to 0° C. Base (NaH, potassium tert-butoxide) (>1.2 eq) is added portionwise at 0° C. The reaction mixture is warmed up and allowed to reflux overnight or until reaction is judged complete ty TLC or HPLC. The reaction mixture is then cooled to rt, treated with solid ammonium chloride and stirred for 10 min. The solution is filtered off, concentrated in vacuo and purified by silica gel column chromatography to afford the 2,4-dialkoxynitroaromatic compound. Alternately, the reaction mixture may be cooled to rt, quenched with cold water, and extracted with EtOAc. Drying and concentration provides the crude nitroaromatic, which may be used without further purification or subjected to silica gel chromatography and then employed in the next step.

Step 3; The 2,4-dialkoxynitroaromatic compound is dissolved in ethanol (0.05-0.5 M) and treated with 4M HCl/dioxane (1-1.5 eq) followed by $SnCl_2 2H_2O$ (5-10 eq). The resulting reaction mixture is then refluxed under nitrogen overnight. After the reaction is complete, solid sodium bicarbonate is added till the pH of the reaction mixture is basic. The mixture is filtered, concentrated and dried in vacuo to provide the 2,4-dialkoxyaniline.

General Procedure C; Reductive Amination of Amines or Anilines

An amine and aldehyde or ketone (1.5 eq) were mixed in 15 ml of 1,2-dichloroethane (0.2-0.5 M in amine) and treated with sodium triacetoxyborohydride (1.5 eq). The mixture was stirred overnight under nitrogen. The reaction mixture was quenched with saturated sodium bicarbonate and extracted with ether or EtOAc. The organic extract was dried over sodium sulfate and concentrated in vacuo to give the crude product, which, if desired, which was purified by flash chromatography eluting with EtOAc/hexane to afford the product.

General Procedure D; Coupling of Carboxylic Acid and Amine

To a solution of carboxylic acid (1.25 eq) in dichloromethane (0.1-0.5 M), DCC (1.25 eq) is added followed by the appropriate protected aniline (1 eq.). The reaction mixture is then stirred at rt overnight. The reaction mixture is filtered and the the filtrate is diluted with DCM and washed with saturated $Na_2CO_3$ and brine. The organic phase is then dried over $Na_2SO_4$, filtered, and the filtrate is concentrated and purified by silica gel chromatography to afford the amide derivative.

General Procedure E; Silyl Protection

An alcohol or phenol is dissolved in DMF (0.1-0.5 M) and imidazole(1.3 eq) followed by TBDMS-Cl (1.3 eq) is added. The reaction was stirred overnight, diluted with water and extracted with EtOAc. The organic layers were combined and washed with brine, dried over anhydrous sodium sulfate and the solvent removed in vacuo to afford the silyl ether.

General Procedure F; Silyl Deprotection

The silyl ether is stirred in THF (0.05-0.5 M) and 1 N tetrabutylammonium fluoride in THF (3 eq) is added to the solution. The mixture is stirred overnight and the solvent removed in vacuo to give the crude product. Alternately, the crude product may be treated with water and and extracted with EtOAc. The organic phase is dried and concentrated in vacuo to afford the free alcohol or phenol.

General Procedure G; Triphenylphosphine/Azodicarboxyate Coupling

The substrate phenol or carboxylic acid is dissolved in THF (0.05-0.5 M) and chilled to 0° C. Triphenylphosphine (1 -4 eq), alcohol (1-4 eq) and duisopropyl azodicaroxylate (DIAD) or diethyl azodicarboxylate (DEAD) (1 -4 eq) were added, in turn. The reaction was stirred overnight with gradual warming to rt. The reaction mixture is diluted with EtOAc/water and the layers were separated. The aqueous layer is further extracted with EtOAc. The organic layers were combined and washed with water and brine and dried over $Na_2SO_4$. The mixture is concentrated in vacuo to give the crude product, which was purified by flash chromatography on silica gel to afford the coupling product.

General Procedure H; Removal of the Fluorenylmethyl Carbamate Group

The protected compound is stirred in a solution of 20% diethyl amine in DCM. The reaction is stirred for 5 hours, the solvent removed, and the product triturated several times with hexane to afford the desired compound.

General Procedure I; Removal of the t-Butyl Carbamate Group

The protected compound is stirred in 4N HCl/dioxane for 1 hour. The solvent removed, and the product triturated several times with ether to afford the desired compound.

EXAMPLE 1

3-(4-Benzyloxyphenyl)propionic Acid 2,4-Di-(3-Diethylamino-1 -propoxy)aniline Amide was prepared according to the following procedure.

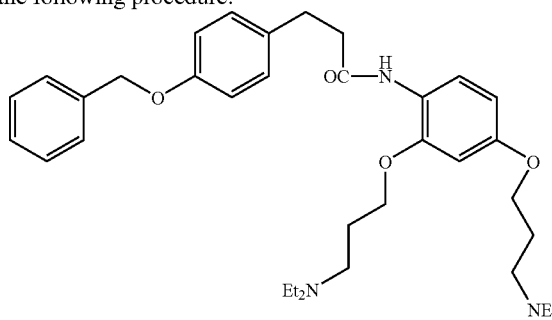

4-Hydroxyphenylpropionic acid (1.66 g) is dissolved in DMF (10 mL). Benzyl bromide (3.76 g) is added to the reaction mixture and cooled to 0° C. Solid NaH (60% dispersion in oil; 1 g) is added portion wise at 0° C. The reaction mixture is warmed up gradually to 60° C. and stirred at that temperature overnight. The reaction mixture is then cooled to room temperature and added with 1 N HCl till the pH of the reaction mixture is neutral. The reaction mixture is then extracted with ethyl acetate (2×50 mL) and the combined extracts are then washed with water (50 mL) and brine (50mL). The organic extract is dried over $Na_2SO_4$, filtered and concentrated to obtain the product ether Intermediate 1a as white solid (2.6 g)

1 g of the product Intermediate 1a obtained as above is dissolved in 1:1 methanol/water (10 mL) and added with solid NaOH (200 mg) and stirred overnight at room temperature. The reaction is then acidified with 10% HCl to bring the pH up to 2-3. The reaction mixture is then extracted with ethyl acetate (2×50 mL) and the combined extracts are then washed with water (50 mL) and brine (50 mL). The organic extract is dried over $Na_2SO_4$, filtered and concentrated to afford 4-benzyloxyphenylpropionic acid Intermediate 1b as white solid (350 mg).

300 mg of the carboxylic acid Intermediate 1b obtained above is dissolved in $CH_2Cl_2$ (5 mL) and added with thionyl chloride (250 µL). The resulting mixture is then refluxed for 1 h and cooled to room temperature. The solvent is removed in vacuo to provide a pale brownish solid Intermediate 1c upon standing (290 mg).

To a solution of 2,4-difluoronitrobenzene (800 mg) in THF (20 mL), N,N-diethylpropanol (2.2 mL) was added and the reaction mixture is cooled to 0° C. Solid NaH (60% dispersion in oil; washed with hexane; 600 mg)) is added portion wise at 0° C. The reaction mixture is warmed up gradually allowed to reflux for 24 h. The reaction mixture is then cooled to room temperature, added with solid ammonium chloride and stirred for 10 min. The solution is filtered off, concentrated in vacuo and purified by silica gel column chromatography using 2:10:90 triethylamine/methanol/chloroform as eluent to yield 1.4 g of the nitro product Intermediate 1d.

The nitro product Intermediate 1d obtained above is dissolved in ethanol (0.05-0.5 M) and treated with 4M HCl/dioxane (1-1.5 eq) followed by $SnCl2H_2O$ (5 g). The resulting reaction mixture is the refluxed under nitrogen overnight. After the reaction is complete, solid sodium bicarbonate is added till the pH of the reaction mixture is basic. The solution is filtered off, concentrated and dried in vacuo to provide 2,4-(N,N-diethylamino)propylaniline Intermediate 1e as a brownish resin (950 mg).

To a cooled (0° C.) solution of Intermediate 1c acid chloride, prepared as above (70 mg) in $CH_2Cl_2$ (5 mL) Intermediate 1e 2,4-(N,N-diethylamino)propylaniline (80 mg) is added. The reaction mixture is then warmed to room temperature gradually and stirred for 1 h. The reaction mixture is added with methanol (0.5 mL) to quench the excess acid chloride. The resulting solution was diluted with $CH_2Cl_2$ (10 mL), added with satd sodium bicarbonate (5 mL) and stirred for 5 min. The reaction mixture is taken in separatory funnel and the layers separated. The organic layer is washed with water (10 mL) and brine (10 mL). The organic extract is dried over $Na_2SO_4$, filtered, concentrated and purified by silica gel column chromatography using 5% methanol/chloroform to obtain 3-(4-Benzyloxyphenyl)propionic Acid 2,4-Di-(3-Diethylamino-1-propoxy)aniline Amideas pale yellow solid (120 mg). MS: m/z 590.4 (M+H).

EXAMPLE 2

3-(3-Tert-butoxyphenyl)-3-(9-fluorenylmethoxycarbonylamino)propionic Acid 2,4-Di-(3-diethylaminopropoxy)aniline Amide was prepared according to the following procedure.

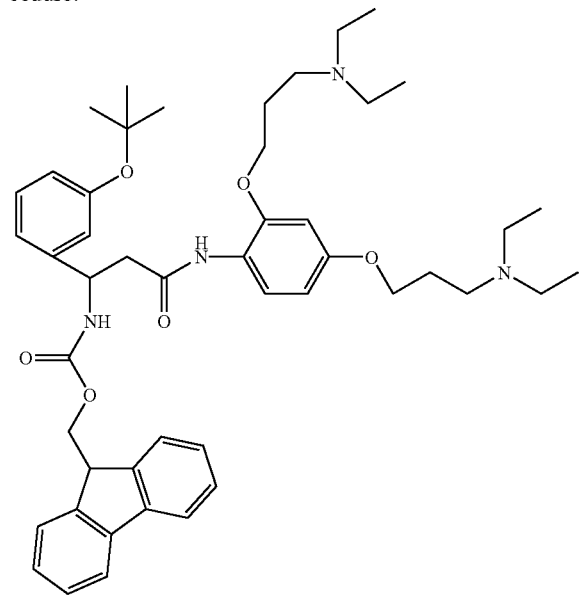

To a solution of 3-(3-tert-butoxyphenyl)-3-(9-fluorenylmethoxycarbonylamino)propionic acid (192 mg) in acetonitrile (5 mL), HBTU (200 mg) and DIEA (106 mg) are added at rt followed by 2,4-di-(3-diethylaminopropoxy)aniline (137 mg). The reaction mixture is then stirred at rt overnight. The filtrate is concentrated and purified on a silica gel column to afford 210 mg of 3-(3-Tert-butoxyphenyl)-3-(9-fluorenylmethoxycarbonylamino)propionic Acid2,4-Di-(3-diethylaminopropoxy)aniline Amide. LC: $T_r$ 2.17 min; MS: m/z 793 $(M+H)^+$.

EXAMPLE 3

3-(3-Tert-butoxyphenyl)-3-aminopropionic Acid 2,4-Di-(3-diethylaminopropoxy)aniline Amide was prepared according to the following procedure.

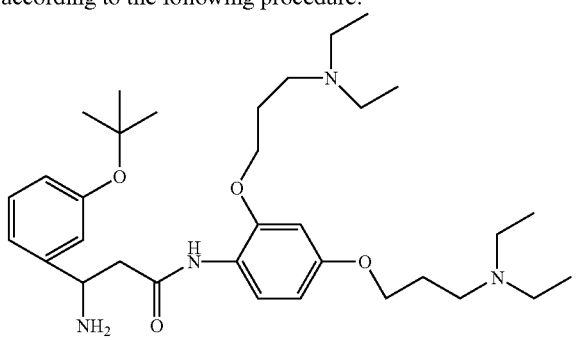

The compound of Example 2 (20 mg) is treated as described in General Procedure H. The solid product is collected and dried under vacuum to afford the amine, Example 3, as a pale brown solid (10.5 mg).

EXAMPLE 4

3-(4-Tetrahydropyranyl)-2-aminopropionic Acid 4-Diethylaminoethoxycarbonyl-2-butoxyaniline Amide Dihydrochloride was prepared according to the following procedure.

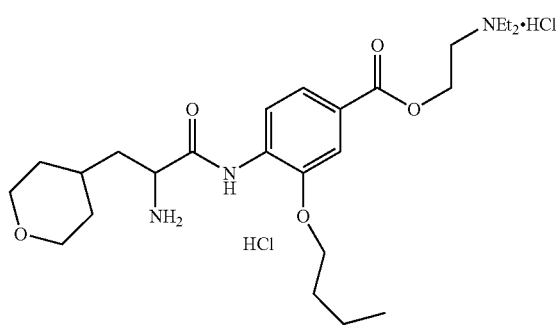

To a solution of BOC-(4-tetrahydropyranyl)alanine (97 mg) and 4-diethylaminoethoxycarbonyl-2-butoxyaniline hydrochloride (120 mg) in acetonitrile (2 mL) at rt, HBTU (160 mg) and DIEA (175 μL) were added in succession. The resulting mixture is stirred overnight. The deep reddish reaction mixture is diluted with EtOAc/water (5 mL/3 mL) and the layers were separated. The aqueous layer is further extracted with EtOAc (5 mL). The organic layers were combined and washed with water and brine and dried over Na2SO4. The solution is filtered and the solvent is removed in vacuo. The resulting crude product is purified by silica gel column chromatography using methanol/CHCl3/hexane (1:20:20) as eluent to afford 55 mg of the amide product Intermediate 4A. LC: Tr 1.90 min; MS: m/z 564 $(M+H)^+$.

The amide Intermediate 4A is treated as described in General Procedure I. The solid product is collected and dried to afford the amine salt Example 4 as a pale yellow solid (30 mg).

EXAMPLE 5

(2S, 4R)-4-Tert-Butoxypyrrolidine-2-carboxylic acid 2,4-Di(3-diethylamino-1-propoxy)aniline Amide was prepared according to the following procedure.

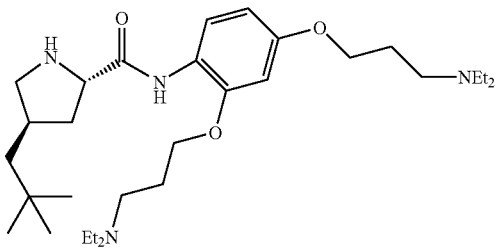

A solution of (2S, 4R)-4tert-butoxy-1-(9-fluorenylmethoxycarbonyl)pyrrolidine-2-carboxylic acid (111 mg, 0.27 mmol) in 5 mL of acetonitrile was treated with HBTU (116 mg; 0.30 mmol) and DIEA (0.10 mL, 0.6 mmol) at room temperature. After 5 min. 2,4-di(3-diethylamino-1-propoxy)aniline (90 mg, 0.26 mmol) is added and the resulting solution is stirred overnight. The reaction mixture is diluted with 10 mL of brine and extracted with ethyl acetate (3×10 mL). The organic layer is washed with water (2×10 mL), saturated Na2CO3 (1×10 mL), brine (1×10 mL). The organic layer is dried over Na2SO4, and the solvent removed in vacuo. The oily residue is triturated with hexane and purified on a silica gel column to yield the 118 mg of the amide Intermediate 5a as a solid. $T_r$ 1.88 min m/z 743 $(M+H)^+$ 20 mg of Intermediate 5a is treated as described in General Procedure H, yielding 9 mg of the amine Example 5 as a solid.

EXAMPLE 6

(3S)-1,2,3,4-Tetrahydroisoquinoline-3-carboxylic Acid 4-Diethylaminoethoxycarbonyl-2-butoxyaniline Amide Dihydrochloride was prepared according to the following procedure.

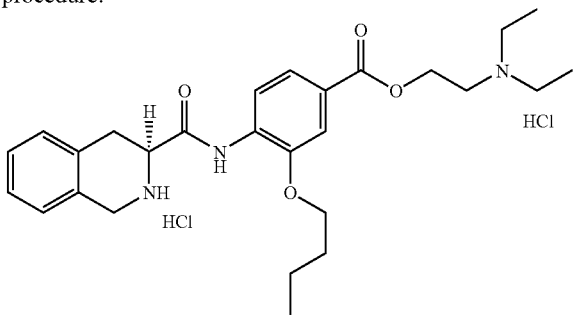

A solution of BOC-L-tetrahydroisoquinoline-3-carboxylic acid (1.1 g) in DMF at room temperature is treated with DCC (412 mg) and stirred for 1 h. The reaction mixture is then filtered and the filtrate is treated with 2-butoxy4-diethylaminoethoxycarbonylaniline hydrochloride (345 mg) and triethylamine (139 μL). The resulting solution was stirred overnight at room temperature. The reaction is then diluted with ethyl acetate and 5% sodium carbonate solution. The contents are shaken in a separatory funnel and the layers separated.

The organic layer is washed with water and brine. The extract is then dried over MgSO$_4$, filtered and the solvent is removed in vacuo. The residue obtained is purified by silica gel column chromatography to afford the desired product Intermediate 6a. LC: T$_r$ 4.72 min; MS: m/z 568.6 (M+H).

The product obtained above is treated as described in General Procedure I. The solid product was then collected and dried under vacuum to afford Example 6 as a pale yellow solid (30 mg). LC: Tr 3.83 min; MS: m/z 468.6 (M+H)

EXAMPLE 7

(R)-3-(4-Benzyloxyphenyl)-2-(1-imidazolyl)propionic Acid 4-Diethylaminoethoxycarbonyl-2-butoxyaniline Amide was prepared according the following procedure.

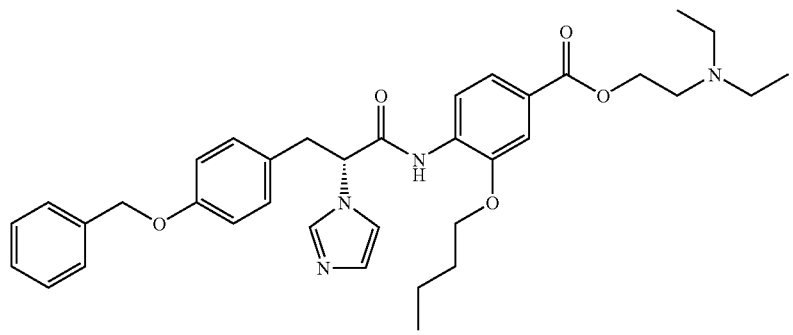

To a solution of Boc-D-Tyr(Bzl)-OH (1.11 g) in CH$_2$Cl$_2$ (15 mL), HOBT (406 mg) and DCC (681 mg) are added at room temperature under nitrogen atmosphere. After 2 h triethylamime (840 μL) and 4-diethylaminoethoxycarbonyl-2-butoxyan iline hydrochloride (1.04 g) are added followed by DMAP (36 mg). The reaction mixture is then stirred at room temperature for 3 d and filtered to remove dicyclohexylurea. The filtrate is concentrated and purified on a silica gel column chromatography to afford 1.2 g the product amide Intermediate 7a. LC: Tr 2.18 min; MS: m/z 662 (M+H).

165 mg of Intermediate 7a obtained above is treated as described in General Procedure I. The product is then dried under vacuum to afford a pale yellow solid, Intermediate 7b. (105 mg). LC: Tr 1.75 min; MS: m/z 562 (M+H).

32 mg of the hydrochloride salt Intermediate 7b obtained as above is treated with 100 μL of aq. glyoxal, 100 μL of aq. formaldehyde and 38 mg of ammonium acetate and the reaction mixture is heated to 100° C. overnight. The reaction mixture is then allowed to cool to room temperature and added with satd. sodium bicarbonate solution till the pH of the reaction mixture is between 7-8. The reaction mixture is then extracted with ethyl acetate (2×5 mL) and the combined extracts are then washed with water (5 mL) and brine (5 mL). The organic extract is dried over Na$_2$SO$_4$, filtered and concentrated and purified by flash chromatography on silica gel eluted with 5% methanol in chloroform to obtain 15 mg of the desired product Example 7 as a yellow solid. LC: Tr 1.80 min; MS: m/z 613 (M+H).

EXAMPLE 8

3-(4-Tert-butoxyphenyl)-3-(9-fluorenylmethoxycarbonylamino)propionic Acid 2,4-Di-(3-diethylaminopropoxy) aniline Amide was prepared according to the following procedure.

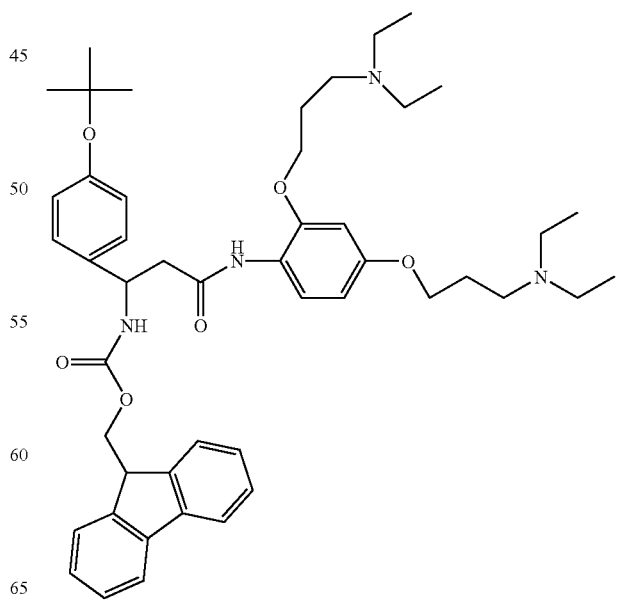

To a solution of 3-(9fluorenylmethoxycarbonylamino)-3-(4-tert-butoxy)phenylpropionic acid (384 mg) in acetonitrile (10 mL), HBTU (400 mg) end DIEA (212 mg) are added at rt followed by 2,4-di-(3-diethylaminopropoxy)aniline (274 mg). The reaction mixture is then stirred at rt overnight. The filtrate is concentrated and purified on a silica gel column to afford 325 mg of the product amide, Example 8. LC: Tr 2.19 min; MS: m/z 793 (M+H)+.

EXAMPLE 9

3-amino-3-(4-tert-butoxyphenyl)propionic Acid 2,4-Di-(3-diethylaminopropoxy)anline Amide was prepared according to the following procedure.

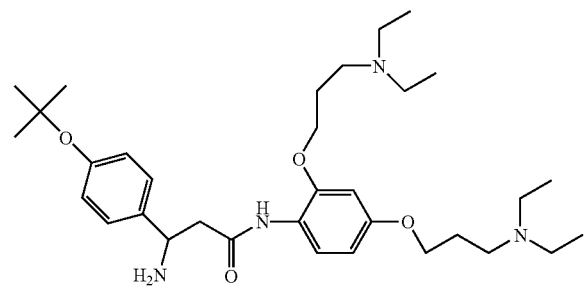

The compound of Example 8 (200 mg) treated as described in General Procedure H. The solid product is collected and dried under vacuum to afford the amine, Example 9, as a pale brown solid (105 mg). MS: m/z 571 (M+H)+

EXAMPLE 10

3-(9-fluorenylmethoxycarbonylamino)-3-(2-tert-butoxyphenyl)propionic Acid 2,4-Di-(3-diethylaminopropoxy)aniline Amide was prepared according to the following procedure.

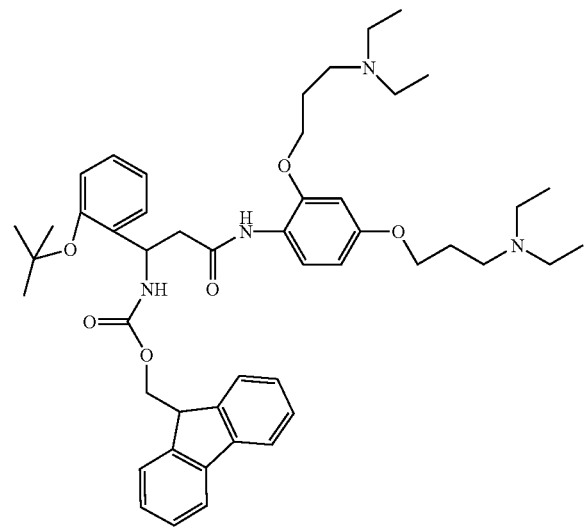

To a solution of 3-(9-fluorenylmethoxycarbonylamino)-3-(2-tert-butoxy)phenylpropionic acid (370 mg) in acetonitrile (10 mL), HBTU (390 mg) and DIEA (212 mg) are added at rt followed by 2,4-di-(3-diethylaminopropoxy)aniline (265 mg). The reaction mixture is then stirred at rt overnight. The filtrate is concentrated and purified on a silica gel column to afford 305 mg of the product amide, Example 8. LC: Tr 2.23 min; MS: m/z 793 (M+H)+.

EXAMPLE 11

3-amino-3-(2-tert-butoxyphenyl)propionic Acid 2,4-Di-(3-diethylaminopropoxy)aniline Amide was prepared according to the following procedure.

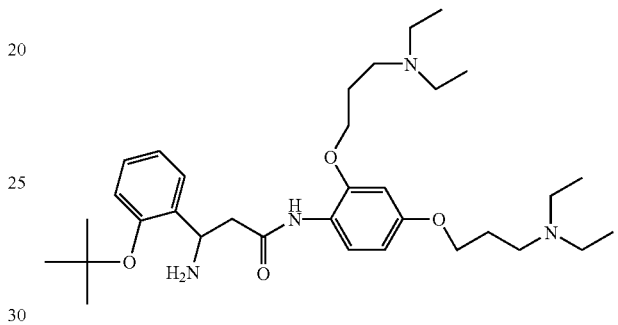

The compound of Example 10 (75 mg) is treated as described in General Procedure H. The solid product is collected and dried under vacuum to afford the amine, Example 11, as a brown solid (30 mg). MS: m/z 571 (M+H)+

EXAMPLE 12

3-Isopropylamino-3-(3-tert-butoxyphenyl)propionic Acid 2,4-Di-(3-diethylaminopropoxy)aniline Amide was prepared according to the following procedure.

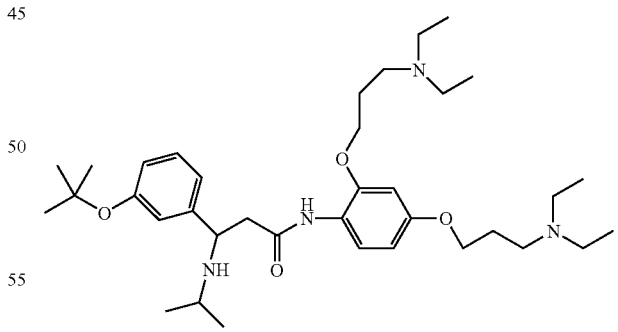

To a solution of the compound of Example 3 (650 mg) in methanol (5 mL) is added acetone (0.06 mL). After 40 min, 1.2 mL of 1 M sodium cyanoborohydride in THF is added. The reaction is stirred overnight, the solvent removed in removed in vacuo, and the crude compound purified by flash chromatography on silica gel (4:1 hexane:EtOAC, 10% TEA) to yield 637 mg of Example 12. LC: Tr 1.84 min; MS: m/z 613 (M+H)+

EXAMPLE 13

(2R)-2-tert-butoxycarbonylamino-3-[4-(benzyloxy)phenyl]propionic Acid 4-(3-diethylaminopropoxy)-N-benzylaniline Amide was prepared according to the following procedure.

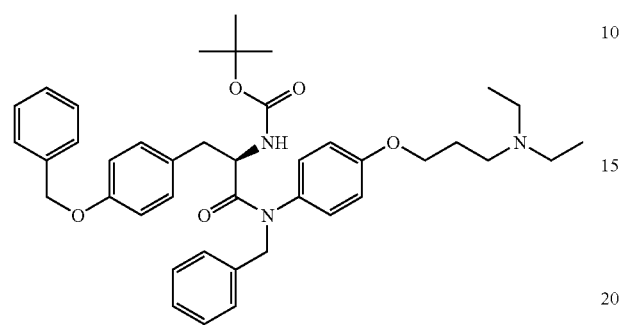

Para-aminophenol was reductively aminated with benzaldehyde according to General Procedure C. This phenol was protected with the tert-butyldimethylsilyl group according to General Procedure E. The product 4-O-tert-butyidimethylsilyl-N-benzyl aniline (274 mg) was used for the coupling with N-Boc-O-benzyl tyrosine accroding to General Procedure D. The product was desilylated according to General Procedure F to afford 109 mg of Example 13 LC: Tr 2.32 min; MS: m/z 667 (M+H)$^+$.

EXAMPLE 14

(2R)-2-tert-butoxycarbonylamino-3-[4-(benzyloxy)phenyl]propionic Acid 4-(3-diethylaminopropoxy)-N-cyclopentylmethylaniline Amide was prepared according to the following procedure.

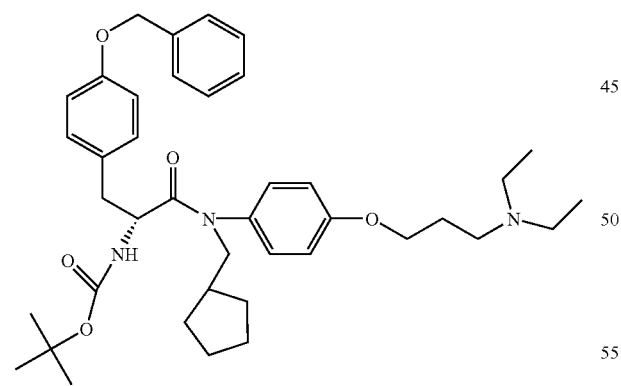

Para-aminophenol was reductively aminated with cyclopentylcarboxaldehyde according to General Procedure C. This phenol was protected with the tert-butyldimethylsilyl group according to General Procedure E. The product 4-O-tert-butyidimethylsilyl-N-benzyl aniline (274 mg) was used for the coupling with N-Boc-O-benzyl-D-tyrosine according to General Procedure D. The product was desilylated according to General Procedure F to afford 96 mg of Example 14. LC: Tr 2.21 min; MS: m/z 659 (M+H)$^+$.

EXAMPLE 15

(2R)-2-tert-butoxycarbonylamino-3-[4-(benzyloxy)phenyl]propionic Acid 4-(3-diethylaminopropoxy)-N-isopropylaniline Amide was prepared according to the following procedure.

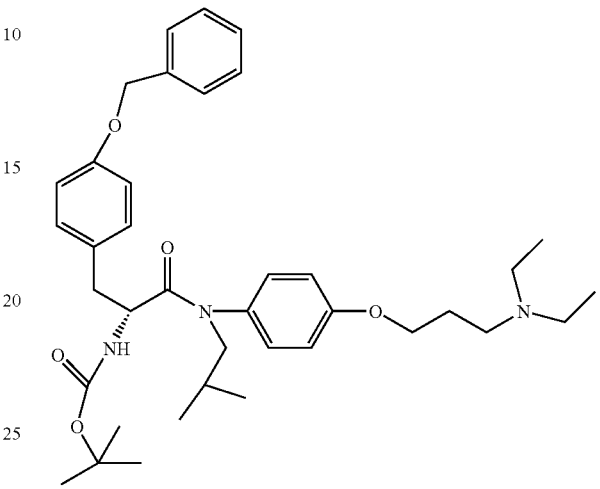

Para-aminophenol was reductively aminated with isobutyraldehyde according to General Procedure C. This phenol was protected with the tert-butyidimethylsilyl group according to General Procedure E. The product 4-O-tert-butyidimethylsilyl-N-benzyl aniline (274 mg) was used for the coupling with N-Boc-O-benzyl-D-tyrosine according to General Procedure D. The product was desilylated according to General Procedure F to afford 114 mg of Example 15. LC: T$_r$ 2.19 min; MS: m/z 619 (M+H)$^+$.

EXAMPLE 16

(2R)-2-amino-3-[4-(benzyloxy)phenyl]propionic Acid 4-(3-diethylaminopropoxy)-N-cyclohexylmethylaniline Amide was prepared according to the following procedure.

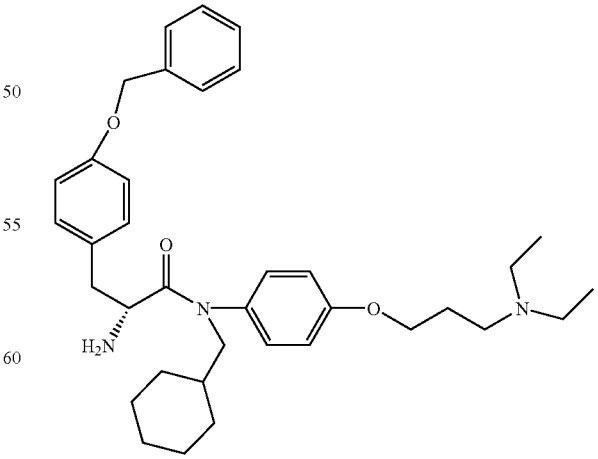

Para-aminophenol was reductively aminated with cyclohexanecarboxaldehyde according to General Procedure C.

This phenol was protected with the tert-butyldimethylsilyl group according to General Procedure E. The product 4-O-tert-butyldimethylsilyl-N-benzyl aniline (274 mg) was used for the coupling with N-Boc-O-benzyl-D-tyrosine according to General Procedure D. The product was desilylated according to General Procedure F and then the resulting product was treated as described in General Procedure I to afford 78 mg of Example 16. LC: T$_r$ 2.02 min MS: m/z 573(M+H)$^+$.

EXAMPLE 17

(2R)-2-amino-3-[4-(benzyloxy)phenyl]propionic Acid 4-(3-diethylaminopropoxy)-N-cyclopentylmethylaniline Amide was prepared according to the following procedure.

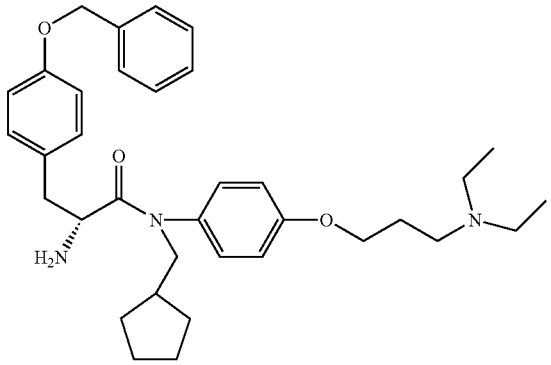

Para-aminophenol was reductively aminated with cyclopentanecarboxaldehyde according to General Procedure C. This phenol was protected with the tert-butyidimethylsilyl group according to General Procedure E. The product 4-O-tert-butyidimethylsil-N-benzyl aniline (274 mg) was used for the coupling with NBoc-O-benzyl-D-tyrosine according to General Procedure D. The product was desilylated according to General Procedure F and then the resulting product was treated as described in General Procedure I to afford 56 mg of Example 16. LC: Tr 2.26 min MS m/z 559 (M+H)$^+$.

EXAMPLE 18

(2R)-2-tert-butoxycarbonylamino-3-[4-(benzyloxy)phenyl]propionic Acid 4-(3-diethylaminopropoxy)-N-butylaniline Amide was prepared according to the following procedure.

4-aminophenol (550 mg; 5 mmol) is added to a solution of butyric acid (1.4 mL; 15 mmol) in DCM (20 mL) at room temperature and stirred vigorously. To this solution DCC (2.48 g; 12 mmol) is added followed by DMAP (24 mg) and the contents stirred overnight at room temperature. The reaction mixture is then filtered and washed with DCM. The filtrate is concentrated and redissolved in methanol, added with 10% aqueous sodium bicarbonate solution and stirred vigorously until diacylated byproduct disappeared (as detected by LC-MS) to yield 4-butyramidophenol as the only product. The product was used for further transformation without further purification.

Mesyl Chloride (6.0 mmol) was added dropwise at 0° C. to a stirred solution of N,N-diethylaminopropanol (6.0 mmol), TEA (6.0 mmol) in anhydrous DCM (6 mL), and the mixture was stirred at the same temperature for 10 min, and at room temperature for additional 1 h. After the removal of the solvent in vacuo, the solid residue was mixed with 4-butyramidophenol (5.0 mmol), and K$_2$CO$_3$ (10 mmol) in anhydrous DMF (10 mL), following general procedure B. The crude product is purified using silica gel column chromatography 5% MeOH/DCM as eluent to yield 4-(N,N-diethylaminopropoxy)butyranilide (1.4 g).

The anilide obtained above (2.5 mmol) is dissolved in THF (5 mL) and cooled to 0° C. A solution of LAH in THF (1M; 4 mL) is added to the reaction mixture and warmed to room temperature. The contents are refluxed for 6 h, cooled to rt. and methanol was added until the evolution of hydrogen ceased. The reaction mixture is then concentrated, extracted with CHCl$_3$, washed with 10% NH$_4$OH followed by water and brine and dried over Na$_2$SO$_4$. After removal of the drying agent, The crude product, 4-(3-diethylaminopropoxy)aniline (400 mg) was used for further transformation without any purification.

The aniline obtained above (0.65 mmol) in acetonitrile (2 mL) is added with Boc-Tyr(Bzl-OH (0.65 mmol) and HBTU (0.72 mmol). The reaction mixture is then stirred at rt overnight. The filtrate is concentrated and purified on a silica gel column to afford 100 mg of the desired product. LC: Tr 2.21 min MS m/z632.8 (M+H)$^+$.

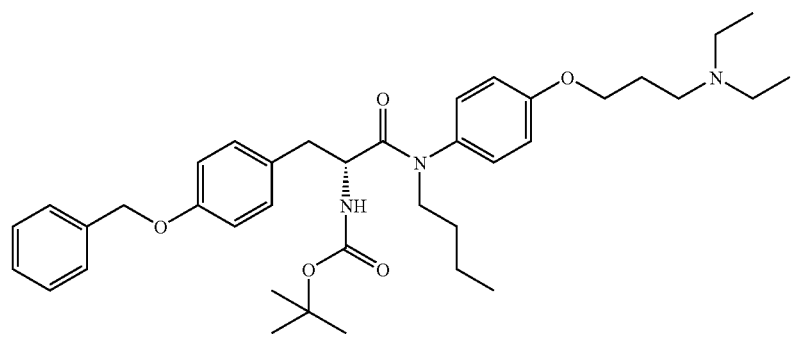

EXAMPLE 19

(2R)-2-amino-3-[4-(benzyloxy)phenyl]propionic Acid 4-(3-diethylaminopropoxy)-N-butylaniline Amide was prepared according to the following procedure.

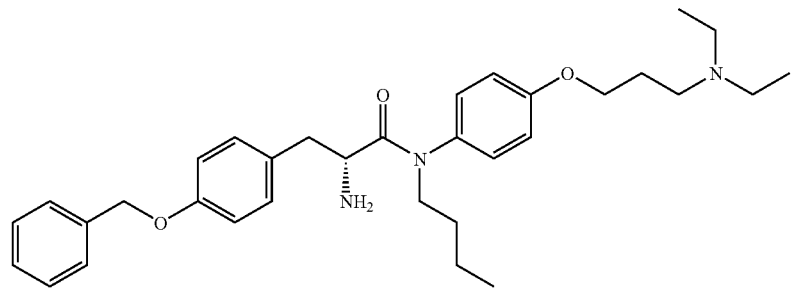

The compound of Example 18 (100 mg) was treated as described in General Procedure I. Final yield 60 mg LC: Tr 1.90 min MS m/z 532.7 (M+H)$^+$.

EXAMPLE 20

(2R)-2-tert-butoxycarbonylamino-3-[4-(benzyloxy)phenyl]propionic Acid 3-(3-diethylaminopropoxy)-N-butylaniline Amide was prepared according to the following procedure.

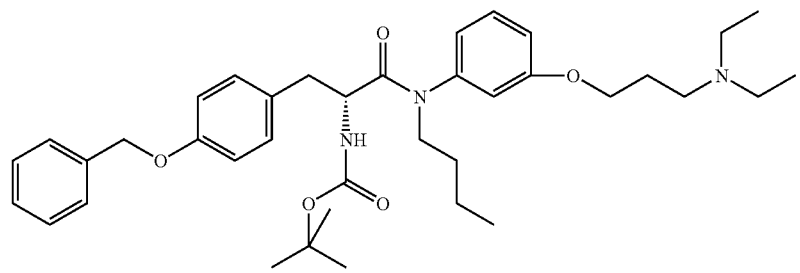

3-aminophenol (550 mg; 5 mmol) is added to a solution of butyric acid (1.4 mL; 15 mmol) in DCM (20 mL) at room temperature and stirred vigorously. To this solution DCC (2.48 g; 12 mmol) is added followed by DMAP (24 mg) and the contents stirred overnight at room temperature. The reaction mixture is then filtered and washed with DCM. The filtrate is concentrated and redissolved in methanol, added with 10% aqueous sodium bicarbonate solution and stirred vigorously until diacylated byproduct disappeared (as detected by LC-MS) to yield 3-butyramidophenol as the only product. The product was used for further transformation without further purification.

The mesylate of N,N-diethylaminopropanol (6 mmol), prepared as described in Example 18 above, was mixed with 3-butyramidophenol (5.0 mmol), and K$_2$CO$_3$ (10 mmol) in anhydrous DMF (10 mL) and the reaction is performed following general procedure B. The crude product is purified using silica gel column chromatography 5% MeOH/DCM as eluent to yield 3-(N,N-diethylaminopropoxy)butyranilide (1.3 g).

The anilide obtained above (2.5 mmol) is dissolved in THF (5 mL) and cooled to 0° C. A solution of LAH in THF (1M; 4 mL) is added to the reaction mixture and warmed to room temperature. The contents are refluxed for 6 h, cooled to rt. and methanol added until the evolution of hydrogen ceases. The reaction mixture is then concentrated, extracted with CHCl$_3$, washed with 10% NH$_4$OH followed by water and brine and dried over Na$_2$SO$_4$. After removal of the drying agent, The crude product, 3-(3-diethylaminopropoxy)aniline (500 mg) was used for further transformation without any purification.

The aniline obtained above (0.65 mmol) in acetonitrile (2 mL) is added with Boc-D-Tyr(Bzl)-OH (0.65 mmol) and HBTU (0.72 mmol). The reaction mixture is then stirred at rt overnight. The filtrate is concentrated and purified on a silica gel column to afford 100 mg of the desired product. LC: Tr 2.14 min MS m/z 632.7 (M+H)$^+$.

EXAMPLE 21

(2R)-2-amino-3-[4-(benzyloxy)phenyl]propionic Acid 3-(3-diethylaminopropoxy)-N-butylaniline Amide was prepared according to the following procedure.

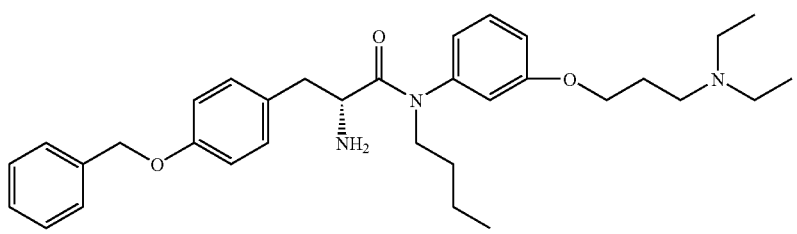

The compound of Example 20 (100 mg) was treated as described in General Procedure I. Final yield 60 mg. LC: Tr 1.78 min MS m/z 532.7 (M+H)+.

EXAMPLE 22

3-(1-Tert-butoxycarbonylpiperidin-4-yl)-2-(9-fluorenylmethoxycarbonylamino)propionic Acid 4-Diethylaminopropoxy-2-butoxyaniline Amide was prepared according to the following procedure.

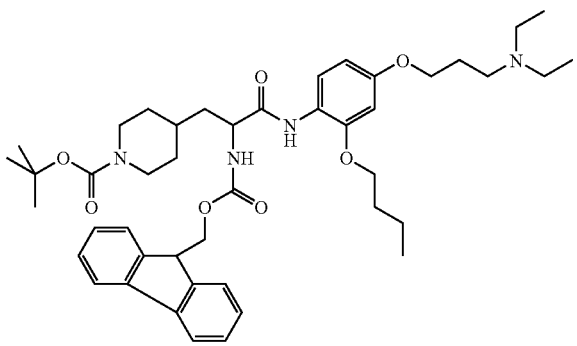

To a stirred solution of 3-fluoro-4-nitrophenol (5 mmol) in DMF, mesylate of N,N-diethylaminopropanol (6 mmol) and $K_2CO_3$ (10 mmol) are added and the reaction is performed following the general procedure for alkylation of phenols. The crude product, 2-fluoro-4-(N,N-diethylaminopropoxy)nitrobenzene is used for further transformation without any purification.

The product above is dissolved in dry THF (10 mL) and is added with n-butanol (6 mmol) and KOtBu (5.5 mmol) at 0° C. following the general procedure. The crude product, 2-butoxy4-(N,N-diethylaminopropoxy)nitrobenzene is used for further transformation without any purification.

The nitro product (5 mmol) above is hydrogenated as described in step 3 of general procedure B above. The product, 2-butoxy-4-(N,N-diethylaminopropoxy)aniline thus obtained is used for further transformation without any purification.

The aniline obtained above (0.5 mmol) in DCM (2 mL) is added with Fmoc-Ala(4-N-Boc-piperidinyl)-OH (0.65 mmol) and HBTU (0.72 mmol). The reaction mixture is then stirred at rt overnight. The filtrate is concentrated and purified on a silica gel column to afford 300 mg of the desired product. LC: Tr 2.45 min MS m/z 772.0 (M+H)+.

EXAMPLE 23

3-(Piperidin-4-yl)-2-(9-fluorenylmethoxycarbonylamino)propionic Acid 4-Diethylaminopropoxy-2-butoxyaniline Amide was prepared according to the following procedure.

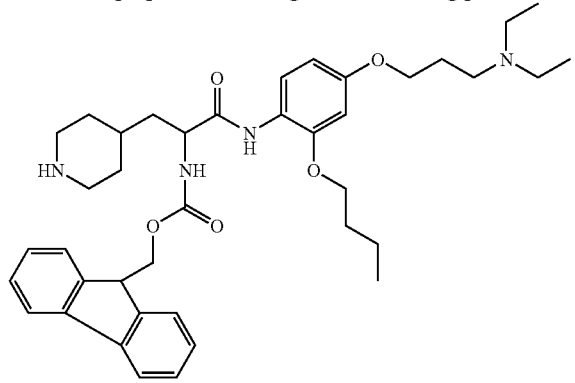

The compound of Example 22 (100 mg) was treated as described in General Procedure I. Final yield 52 mg. LC: Tr 2.02 min MS m/z 672.0 (M+H)+.

EXAMPLE 24

3-(1-Benzylpiperidin-4-yl)-2-(9-fluorenylmethoxycarbonylamino)propionic Acid 4-Diethylaminopropoxy-2-butoxyaniline Amide was prepared according to the following procedure.

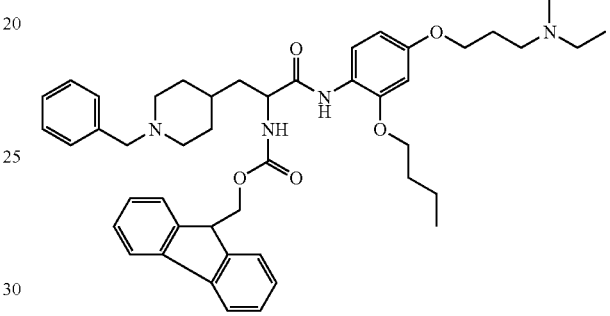

The compound of Example 23 (100 mg) was treated with benzaldehyde as described in General Procedure C. Final yield 110 mg. LC: Tr 2.20 min MS m/z 762.0 (M+H)+.

EXAMPLE 25

3-(1-Benzylpiperidin-4-yl)-2-aminopropionic Acid 4-Diethylaminopropoxy-2-butoxyaniline Amide was prepared according to the following procedure.

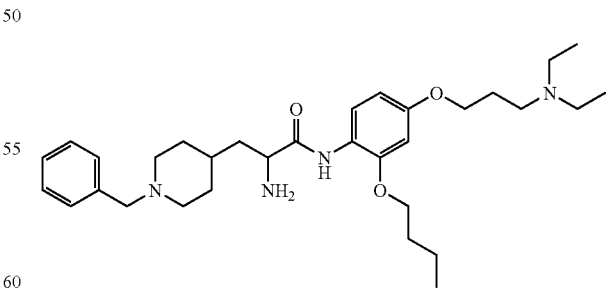

The compound of Example 24 (75 mg) was treated as described in General Procedure H. Final yield 48 mg. LC: Tr 2.20 min MS m/z 762.0 (M+H)+.

EXAMPLE 26

3-(1-Benzyloxycarbonylpiperidin-4-yl)-2-(9-fluorenyl-methoxycarbonyamino)propionic Acid 4-Diethylaminopropoxy-2-butoxyaniline Amide was prepared according to the following procedure.

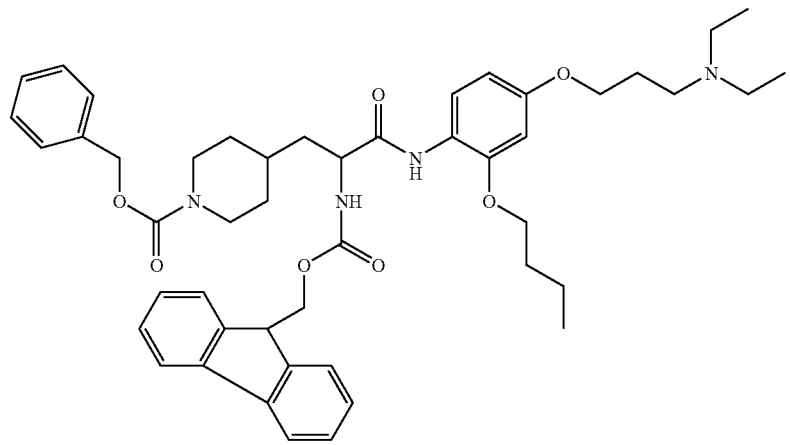

The compound of Example 23 (60 mg) was treated with N-(benzyloxycarbonyloxy)succinimide (60 mg) in a solution of dioxane (1.5 mL) and 1 M sodium carbonate in water (0.5 mL). The reaction was stirred for 4 hours, extracted with EtOAc, and the organic layer dried over $Na_2SO_4$. the solvent was removed and the product purified by column chromatography. Final yield 55 mg. LC: Tr 2.60 min MS m/z 806.0 $(M+H)^+$.

EXAMPLE 27

3-(1-Benzoylpiperidin-4-yl)-2-(9-fluorenylmethoxycarbonylamino)propionic Acid 4-Diethylaminopropoxy-2-butoxyaniline Amide was prepared according to the following procedure.

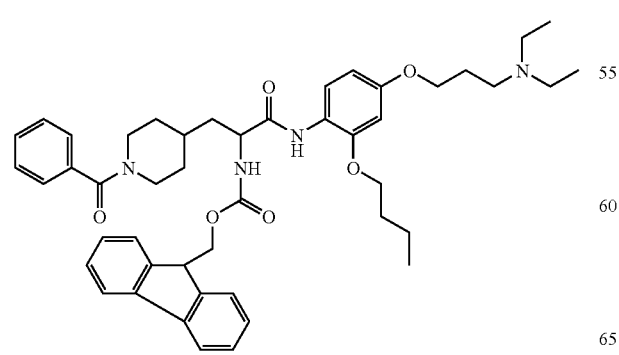

The compound of Example 23 (45 mg) was treated with benzyl chloride (55 mg) in DCM (1 mL) at 0° C. the reaction was warmed to room temperature and allowed to stir for 2 hours. The reaction was diluted with DCM, washed with saturated sodium bicarbonate, and the organic layer dried over $Na_2SO_4$. the solvent was removed and the product purified by column chromatography. Final yield 27 mg. LC: Tr 2.34 min MS m/z 776.0 $(M+H)^+$.

EXAMPLE 28

3-(1-Benzoylpiperidin-4-yl)-2-benzoylaminopropionic Acid 4-Diethylaminopropoxy-2-butoxyaniline Amide was prepared according to the following procedure.

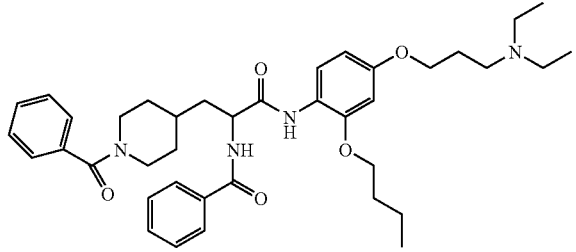

The compound of Example 27 (45 mg) was deprotected according to General Procedure H. The product was then treated with benzyl chloride (55 mg) in DCM (1 mL) at 0° C. the reaction was warmed to room temperature and allowed to stir for 2 hours. The reaction was diluted with DCM, washed with saturated sodium bicarbonate, and the organic layer dried over $Na_2SO_4$. the solvent was removed and the product purified by column chromatography. Final yield 27 mg. LC: Tr 2.34 min MS m/z 776.0 $(M+H)^+$.

EXAMPLE 29

3-(Tert-butoxycarbonylpiperidin-3-yl)-2-(9-fluorenyl-methoxycarbonylamino)propionic Acid 4-Diethylaminopropoxy-2-butoxyaniline Amide was prepared according to the following procedure.

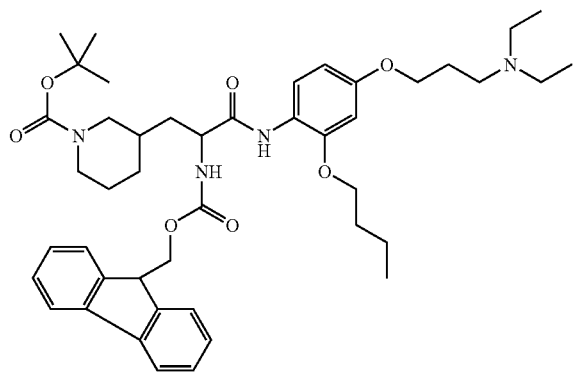

To a stirred solution of 3-fluoro-4-nitrophenol (5 mmol) in DMF, mesylate of N,N-diethylaminopropanol (6 mmol) and $K_2CO_3$ (10 mmol) are added and the reaction is performed following the general procedure for alkylation of phenols. The crude product, 2-fluoro-4-(N,N-diethylaminopropoxy) nitrobenzene is used for further transformation without any purification.

The product above is dissolved in dry THF (10 mL) and is added with n-butanol (6 mmol) and KO$^t$Bu (5.5 mmol) at 0° C. following the General Procedure A. The crude product, 2-butoxy-4-(N,N-diethylaminopropoxy)nitrobenzene is used for further transformation without any purification.

The nitro product (5 mmol) above is hydrogenated as described in step 3 of general procedure B above. The product, 2-butoxy-4-(N,N-diethylaminopropoxy)aniline thus obtained is used for further transformation without any purification.

The aniline obtained above (0.5 mmol) in DCM (2 mL) is added with Fmoc-Ala(3-N-Boc-piperidinyl-OH (0.65 mmol) and HBTU (0.72 mmol). The reaction mixture is then stirred at rt overnight. The filtrate is concentrated and purified on a silica gel column to afford 300 mg of the desired product. LC: Tr 2.56 min MS m/z 772.0 (M+H)$^+$.

EXAMPLE 30

3-(Piperidin-3-yl)-2-(9-fluorenylmethoxycarbonylamino) propionic Acid 4-Diethylaminopropoxy-2-butoxyaniline Amide was prepared according to the following procedure.

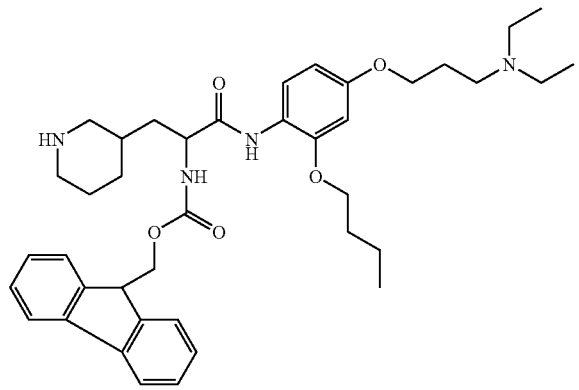

The compound of Example 29 (100 mg) was treated as described in General Procedure I. Final yield 52 mg. LC: Tr 1.96 min MS m/z 672.0 (M+H)$^+$.

Biological Assay

The following assay method is utilized to identify compounds of Formula (I) which are effective in binding with RAGE, and hence useful as modulators, preferably antagonists of RAGE. This method is also described and claimed in co-pending U.S. Ser. No. 09/799,152 filed Mar. 5, 2001.

General Assay Procedure

S100b, β-amyloid and CML (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 1 mM $CaCl_2/MgCl_2$) containing 1% bovine serum albumin (BSA) (300 μL/well) for two h at 37° C. The wells are aspirated and washed 3 times (400 uL/well) with 155 mM NaCl pH 7.2 buffer saline and soaked 10 seconds between each wash.

Test compounds are dissolved in nanopure water (concentration: 10-100 μM). DMSO may be used as co-solvent. 25 μL of test compound solution in 2% DMSO is added, along with 75 μL sRAGE (4.0×10$^{-4}$ mg/mL FAC) to each well and samples are incubated for 1 h at 37° C. The wells are washed 3 times with 155 mM NaCl pH 7.2 buffer saline and are soaked 10 seconds between each wash.

Non-Radioactive Binding is Performed by Adding:

10 μL Biotinylated goat F(ab')2 Anti-mouse IgG. (8.0×10$^{-4}$ mg/mL, FAC)

10 μL Alk-phos-Sterptavidin (3×10$^{-3}$ mg/mL FAC)

10 μL Polyclonal antibody for sRAGE (FAC 6.0×10$^{-3}$ mg/mL)

to 5 mL 50 mM imidazole buffer saline (pH 7.2) containing 0.2% bovine serum albumin and 1 mM $Ca_2Cl_2$. The mixture is incubated for 30 minutes at 37° C. 100 μL complex is added to each well and incubation is allowed to proceed at rt for 1 h. Wells are washed 3 times with wash buffer and soaked 10 s between each wash. 100 μL 1 mg/mL (pNPP) in 1 M diethanolamine (pH adjusted to 9.8 with HCl) is added. Color is allowed to develop in the dark for 1 to 2 h at rt. The reaction is quenched with 10 μL of stop solution (0.5 N NaOH in 50% ethanol) and the absorbance is measured spectrophotometrically with a microplate reader at 405 nm.

IC$_{50}$ (μM) of ELISA assay represents the concentration of compound at which 50% signal has been inhibited.

| | ELISA Assay IC$_{50}$ (μM) | | |
|---|---|---|---|
| Example No. | S-100b | Amyloid-β | Carboxymethyl Lysine (CML) |
| 1 | +++ | NA | NA |
| 2 | +++++ | +++ | ++++ |
| 3 | +++ | +++ | +++ |
| 4 | + | NA | NA |
| 5 | +++ | NA | NA |
| 6 | + | + | ++ |
| 7 | ++++ | +++ | +++ |
| 8 | ++++ | ++++ | ++++ |
| 9 | +++ | +++ | +++ |
| 10 | ++++ | +++ | +++ |
| 11 | +++ | +++ | +++ |
| 12 | +++ | +++ | −++++ |
| 13 | ++ | ++ | ++ |
| 14 | +++ | +++ | +++ |
| 15 | +++ | +++ | ++ |
| 16 | +++ | +++ | +++ |
| 17 | ++ | + | + |
| 18 | +++ | +++ | +++ |
| 19 | +++ | +++ | +++ |
| 20 | +++ | +++ | +++ |
| 21 | +++ | +++ | +++ |
| 22 | +++ | ++++ | ++++ |
| 23 | ++++ | ++++ | +++ |
| 24 | ++++ | ++++ | +++++ |
| 25 | ++ | + | + |
| 26 | +++ | +++ | ++++ |
| 27 | +++ | +++ | +++ |
| 28 | ++ | ++ | +++ |
| 29 | +++ | +++ | +++ |
| 30 | ++++ | ++++ | ++++ |

NA = ELISA assay data not available
Key
+++++ <0.5 μM
++++ Between 0.5 μM and 1 μM
+++ Between 1 μM and 5 μM
++ Between 5 μM and 10 μM
+ Between 10 μM and 20 μM The invention further provides pharmaceutical compositions comprising the RAGE modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in a mixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines. Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, Nmethylglucamine, Oxalate, Pamoate (Embonate), Palmitate, Pantothenate, Phosphateldiphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxiate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug therof, and one or more pharmaceutically acceptable carriers, excipients, or diluents.

The compounds of the present invention selectively act as modulators of RAGE binding to a single endogenous ligand, i.e., selective modulators of β-amyloid-RAGE interaction, and therefore are especially advantageous in treatment of Alzheimer's disease and related dementias.

Further, the compounds of the present invention act as modulators of RAGE interaction with two or more endogenous ligands in preference to others. Such compounds are advantageous in treatment of related or unrelated pathologies mediated by RAGE, i.e., Alzheimer's disease and cancer.

Further, the compounds of the present invention act as modulators of RAGE binding to each and every one of its ligands, thereby preventing the generation of oxidative stress and activation of NF-κB regulated genes, such as the cytokines IL-1, and TNF-α. Thus, antagonizing the binding of physiological ligands to RAGE prevent targeted pathophysiological consequences and useful for management or treatment of diseases, i.e., AGE-RAGE interaction leading to diabetic complications, S100/EN-RAGE/calgranulin-RAGE interaction leading to inflammatory diseases, β-amyloid-RAGE interaction leading to Alzheimer's Disease, and amphoterin-RAGE interaction leading to cancer.

I. RAGE and the Complications of Diabetes

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., *J. Clin. Invest.*, 91:2463-2469 (1993); Reddy, S., et al., *Biochem.*, 34:10872-10878 (1995); Dyer, D., et al., *J. Biol. Chem.*, 266:11654-11660 (1991); Degenhardt, T., et al., *Cell Mol. Biol.*, 44:1139-1145 (1998)). Accumulation of AGEs in the vasculature can occur focally, as in the joint amyloid composed of AGE-$β_2$-microglobulin found in patients with dialysis-related amyloidosis (Miyata, T., et al., *J. Clin. Invest.*, 92:1243-1252 (1993); Miyata, T., et al., *J. Clin. Invest.*, 98:1088-1094 (1996)), or generally, as exemplified by the vasculature and tissues of patients with diabetes (Schmidt, A-M., et al., *Nature Med.*, 1:1002-1004 (1995)). The progressive accumulation of AGEs overtime in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., *J. Biol. Chem.*, 272:16498-16506 (1997); Li, J., et al., *J. Biol. Chem.*, 273:30870-30878 (1998); Tanaka, N., et al., *J. Biol. Chem.*, 275:25781-25790 (2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in the Amyloidoses

Also as noted above, the compounds of the present invention are useful in treating amyloidoses and Alzheimer's disease. RAGE appears to be a cell surface receptor which binds β-sheet fibrillar material regardless of the composition of the subunits (amyloid-β peptide, Aβ, amylin, serum amyloid A, prion-derived peptide) (Yan, S. -D., et al., *Nature*, 382:685-691 (1996); Yan, S-D., et al., *Nat. Med.*, 6:643-651 (2000)). Deposition of amyloid has been shown to result in enhanced expression of RAGE. For example, in the brains of patients with Alzheimer's disease (AD), RAGE expression increases in neurons and glia (Yan, S. -D., et al., *Nature* 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., *Neurosci. Program*, p141-#275.19 (2000)). Inhibition of RAGE-amyloid interaction has been shown to decrease expression of cellular RAGE and cell stress markers (as well as NF-κB activation), and diminish amyloid deposition (Yan, S-D., et al., *Nat. Med.*, 6:643-651 (2000)) suggesting a role for RAGE-amyloid interaction in both perturbation of cellular properties in an environment enriched for amyloid (even at early stages) as well as in amyloid accumulation.

III. RAGE and Propagation of the Immune/Inflammatory Response

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., *TIBS*, 21:134-140 (1996); Zimmer, D., et al., *Brain Res. Bull.*, 37:417-429 (1995); Rammes, A., et al., *J. Biol. Chem.*, 272:9496-9502 (1997); Lugering, N., et al., *Eur. J. Clin. Invest.*, 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade.

IV. RAGE and Amphoterin

As noted above, the compounds of the present invention are useful in treating tumor and tumor metastasis. For example, amphoterin is a high mobility group I nonhistone chromosomal DNA binding protein (Rauvala, H., et al., *J. Biol. Chem.*, 262:16625-16635 (1987); Parkikinen, J., et at., *J. Biol. Chem.* 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., *Nature* 405:354-360 (2000)), and spontaneously arising papillomas in mice expressing the v-Ha-ras transgene (Leder, A., et al., *Proc. Natl. Acad. Sci.*, 87:9178-9182 (1990)).

Amphoterin is a high mobility group I nonhistone chromosomal DNA binding protein (Rauvala, H. and R. Pihlaskari. 1987. Isolation and some characteristics of an adhesive factor of brain that enhances neurite outgrowth in central neurons. *J. Biol. Chem.* 262:16625-16635. (Parkikinen, J., E. Raulo, J. Merenmies, R. Nolo, E. Kajander, M. Baumann, and H. Rauvala. 1993. Amphoterin, the 30 kDa protein in a family of HIMG1-type polypeptides. *J. Biol. Chem.* 268:19 726-19738).

V. RAGE and Erectile Dysfunction

Relaxation of the smooth muscle cells in the cavernosal arterioles and sinuses results in increased blood flow into the penis, raising corpus cavernosum pressure to culminate in penile erection. Nitric oxide is considered the principle stimulator of cavernosal smooth muscle relaxation (See Wingard C J, Clinton W, Branam H, Stopper V S, Lewis R W, Mills T M, Chitaley K. Antagonism of Rho-kinase stimulates rat penile erection via a nitric oxide-independent pathway. Nature Medicine 2001 January; 7(1):119-122). RAGE activation produces oxidants (See Yan, S-D., Schmidt A-M., Anderson, G., Zhang, J., Brett, J., Zou, Y-S., Pinsky, D., and Stem, D. Enhanced cellular oxidant stress by the interaction of advanced glycation endproducts with their receptors/binding proteins. J. Biol. Chem. 269:9889-9887, 1994.) via an NADH oxidase-like enzyme, therefore suppressing the circulation of nitric oxide. Potentially by inhibiting the activation of RAGE signaling pathways by decreasing the intracellular production of AGEs, generation of oxidants will be attenuated. RAGE blockers may promote and facilitate penile erection by blocking the access of ligands to RAGE.

The calcium-sensitizing Rho-kinase pathway may play a synergistic role in cavernosal vasoconstriction to maintain penile flaccidity. The antagonism of Rho-kinase results in increased corpus cavernosum pressure, initiating the erectile response independently of nitric oxide (Wingard et al.). One of the signaling mechanisms activated by RAGE involves the Rho-kinase family such as cdc42 and rac (See Huttunen H J, Fages C, Rauvala H. Receptor for advanced glycation end products (RAGE)-mediated neurite outgrowth and activation of NF-kappaB require the cytoplasmic domain of the receptor but different downstream signaling pathways. J Biol Chem 1999 Jul. 9; 274(28):19919-24). Thus, inhibiting activation of Rho-kinases via suppression of RAGE signaling pathways will enhance and stimulate penile erection independently of nitric oxide.

Thus, in a further aspect, the present invention provides a method for the inhibition of the interaction of RAGE with physiological ligands. In a preferred embodiment of this aspect, the present invention provides a method for treating a disease state selected from the group consisting of acute and chronic inflammation, symptoms of diabetes, vascular permeability, nephropathy, atherosclerosis, retinopathy, Alzheimer's disease, erectile dysfunction, and tumor invasion and/or metastasis, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of RAGE mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (I).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

In a further aspect of the present invention, the RAGE modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the RAGE modulators of the present invention:

Pharmacologic Classifications of Anticancer Agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Pharmacologic Classifications of Treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic Classifications of Treatment for Diabetes Mellitus
1. Sulfonylureas: Tolbutamide, Tolazamide, Glyburide, Glipizide
2. Biguanides: Mefformin
3. Miscellaneous oral agents: Acarbose, Troglitazone
4. Insulin Pharmacologic Classifications of Treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further preferred embodiment, the present invention provides a method of treating RAGE mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

While the invention has been described and illustrated with reference to certain preferred embodiments therof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound of Formula (I):

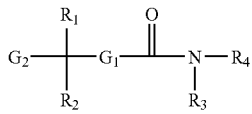

wherein
$G_1$ is $(CH_2)_k$, where k is 1 to 3;
$G_2$ is
  a) hydrogen
  b) —$C_{1-6}$ alkyl;
  c) -aryl;
  d) —$C_{1-6}$ alkylaryl;
  e)

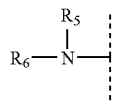

where $R_5$ and $R_6$ are independently selected from the group consisting of
  i) —H;
  ii) —$C_{1-6}$ alkyl;
  iii) -aryl;
  iv) —$C_{1-6}$ alkylaryl;
  v) —C(O)—O—$C_{1-6}$ alkyl;
  vi) —C(O)—O—$C_{1-6}$ alkylaryl;
  vii) —C(O)—O—$C_{1-6}$ alkylcycloalkylaryl;
  viii) —C(O)—NH—$C_{1-6}$ alkyl;
  ix) —C(O)—NH—$C_{1-6}$ alkylaryl;
  x) —$SO_2$—$C_{1-6}$ alkyl;
  xi) —$SO_2$—$C_{1-6}$ alkylaryl;
  xii) —$SO_2$-aryl;
  xiii) —$SO_2$—NH—$C_{1-6}$ alkyl;
  xiv) —$SO_2$—NH—$C_{1-6}$ alkylaryl;

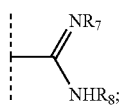

xvi) —C(O)—$C_{1-6}$ alkyl; and
  xvii) —C(O)—$C_{1-6}$ alkylaryl; or
f) a group of the formula

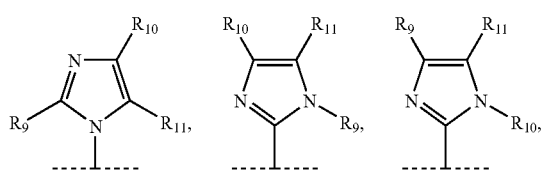

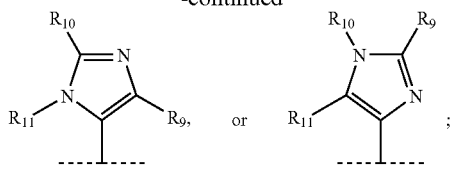

wherein
$R_9$, $R_{10}$, and $R_{11}$ are independently selected from the group consisting of
  i) -hydrogen
  ii) —$C_{1-6}$ alkyl;
  iii) -aryl;
  iv) —$C_{1-6}$ alkylaryl;
  v) —C(O)—O—$C_{1-6}$ alkyl;
  vi) —C(O)—O—$C_{1-6}$ alkylaryl;
  vii) —C(O)—NH—$C_{1-6}$ alkyl;
  viii) —C(O)—NH—$C_{1-6}$ alkylaryl;
  ix) —$SO_2$—$C_{1-6}$ alkyl;
  x) —$SO_2$—$C_{1-6}$ alkylaryl;
  xi) —$SO_2$-aryl;
  xii) —$SO_2$—NH—$C_{1-6}$ alkyl;
  xiii) —$SO_2$—NH—$C_{1-6}$ alkylaryl;
  xiv) —C(O)—$C_{1-6}$ alkyl; and
  xv) —C(O)—$C_{1-6}$ alkylaryl; or
$R_{10}$ and $R_{11}$ are taken together to constitute a fused cycloalkyl, fused heterocyclyl, or fused aryl ring containing the atoms to which $R_{10}$ and $R_{11}$ are bonded;
$R_1$ is
  a) hydrogen;
  b) —$C_{1-6}$ alkyl;
  c) -aryl; or
  d) —$C_{1-6}$ alkylaryl;
$R_2$ is
  a) —$C_{1-6}$ alkyl;
  b) -aryl;
  c) —$C_{1-6}$ alkylaryl; or
  d) a group of the formula

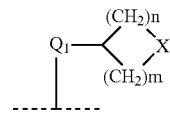

wherein m and n are independently selected from 1, 2, 3, or 4; X comprises a direct bond, $CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

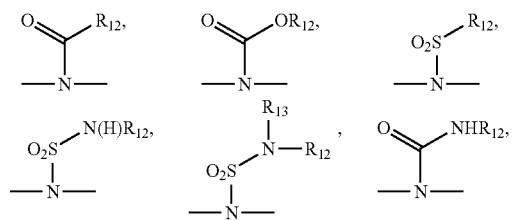

-continued

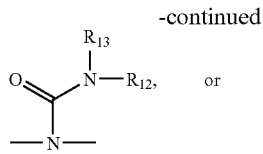

—Q$_1$— is C$_{1-6}$ alkylene, C$_{2-6}$ alkenylene, or C$_{2-6}$ alkynylene;

R$_3$ is
a) hydrogen;
b) —C$_{1-6}$ alkyl;
c) —C$_{1-6}$ alkylaryl; or
d) —C$_{1-6}$ alkoxyaryl;

R$_4$ is

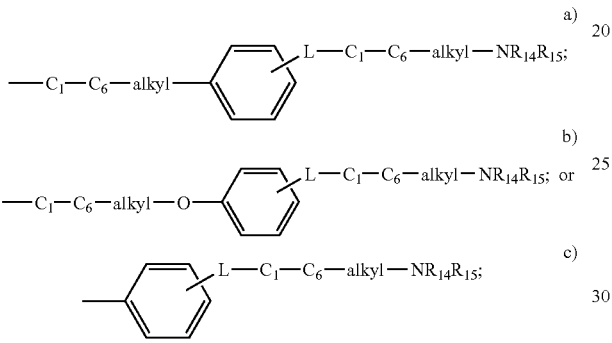

wherein L is —CH$_2$—, —O—, —N(H)—, —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

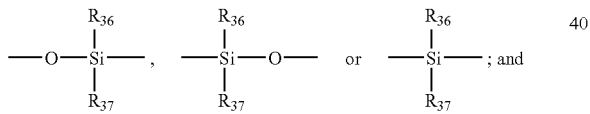

R$_{36}$ and R$_{37}$ are independently from the group consisting of hydrogen, aryl, C$_1$-C$_6$ alkyl, C$_1$-C$_6$ alkylaryl, C$_1$-C$_6$ alkoxy, and C$_1$-C$_6$ alkoxyaryl R$_{12}$ and R$_{13}$ are independently selected from the group consisting of hydrogen, C$_1$-C$_6$ alkyl, C$_1$-C$_6$ alkylaryl, and aryl;

R$_7$ and R$_8$ are independently from the group consisting of hydrogen, C$_1$-C$_6$ alkyl, C$_1$-C$_6$ alkylaryl, and aryl; or R$_7$ and R$_8$ are taken together to form a ring having the formula —(CH$_2$)$_{o'}$-Z'-(CH$_2$)$_{p'}$— bonded to the atoms to which R$_7$ and R$_8$ are attached, wherein o' and p' are, independently, 1, 2, 3, or 4; Z' is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

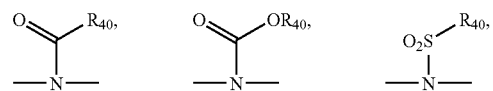

-continued

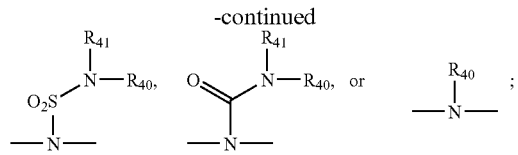

R$_{40}$ and R$_{41}$ are independently from the group consisting of hydrogen, aryl, C$_1$-C$_6$ alkyl, and C$_1$-C$_6$ alkylaryl; and wherein the aryl and/or alkyl group(s) in R$_1$, R$_2$, R$_3$, R$_4$, R$_5$, R$_6$, R$_7$, R$_8$, R$_9$, R$_{10}$, R$_{11}$, R$_{12}$, and R$_{13}$ may be optionally substituted 1-4 times with a substituent group, wherein said substituent group(s) or the term substituted refers to groups:
a) —H;
b) —Y—C$_{1-6}$ alkyl;
  —Y-aryl;
  —Y—C$_{1-6}$ alkylaryl;
  —Y—C$_{1-6}$-alkyl-NR$_{14}$R$_{15}$;
  —Y—C$_{1-6}$-alkyl-W-R$_{16}$;
  wherein Y and W are independently selected from the group consisting of —CH$_2$—, —O—, —N(H)—, —S—, SO$_2$—, —CON(H)—, —NHC(O)—, —NHCON(H)—, —NHSO$_2$—, —SO$_2$N(H)—, —C(O)—O—, —NHSO$_2$NH—, —O—CO—,

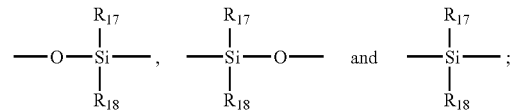

R$_{16}$, R$_{17}$ and R$_{18}$ are independently selected from the group consisting of hydrogen, aryl, C$_1$-C$_6$ alkyl, C$_1$-C$_6$ alkylaryl, C$_1$-C$_6$ alkoxy, or C$_{1-6}$ alkoxyaryl; and c) halogen, hydroxyl, cyano, carbamoyl, or carboxyl; and R$_{14}$ and R$_{15}$ are independently selected from the group consisting of hydrogen, aryl, C$_1$-C$_6$ alkyl, and C$_1$-C$_6$ alkylaryl; or R$_{14}$ and R$_{15}$ are taken together to form a ring having the formula —(CH$_2$)$_o$-Z-(CH$_2$)$_p$— bonded to the nitrogen atom to which R$_{14}$ and R$_{15}$ are attached, wherein o and p are, independently, 1, 2, 3, or 4; Z is a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

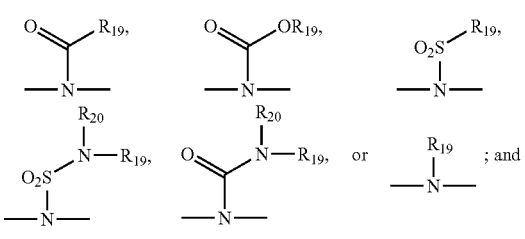

$R_{19}$ and $R_{20}$ are independently selected from the consisting of hydrogen, aryl, $C_1$-$C$ alkyl, and $C_1$-$C_6$ alkyl.

or a pharmaceutically acceptable salt thereof.

2. The compound of claim 1, represented by Formula (Ic):

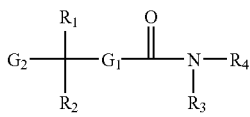

wherein $R_1$ is hydrogen, or $C_{1-3}$ alkylaryl wherein the aryl is substituted with —Y—C-$_{1-6}$ alkylaryl;

$R_2$ is $C_{1-3}$ alkylaryl wherein the aryl is substituted with —Y—C-$_{1-6}$ alkylaryl, wherein Y is —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

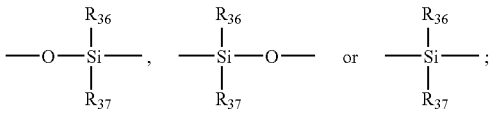

$R_{17}$, and $R_{18}$ independently is hydrogen, aryl, $C_1$-$C_6$ alkyl, $C_1$-$C_6$ alkylaryl, $C_1$-$C_6$ alkoxy, or $C_1$-$C_6$ alkoxyaryl, or a pharmaceutically acceptable salt thereof.

3. The compound of claim 1, represented by Formula (Id):

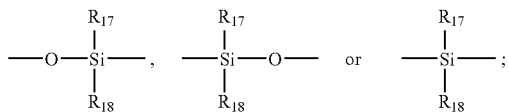

wherein, $R_1$ is hydrogen, or $C_{1-3}$ alkylaryl wherein the aryl is substituted with —Y—C-$_{1-6}$ alkylaryl;

$R_2$ is $C_{1-3}$ alkylaryl wherein the aryl is substituted with —Y—C-$_{1-6}$ alkylaryl;

wherein Y is —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—, $R_{17}$, and $R_{18}$ independently is hydrogen, aryl, $C_1$-$C_6$ alkyl, $C_1$-$C_6$ alkylaryl, $C_1$-$C_6$ alkoxy, or $C_1$-$C_6$ alkoxyaryl;

$R_3$ is hydrogen or -L-$C_{1-6}$-alkyl-N(alkyl)$_2$;

$R_{14}$ and $R_{15}$ are alkyl; and wherein L is —$CH_2$—, —O—, —N(H)—, —S—, $SO_2$—, —CON(H)—, —NHC(O)—, —NHCON (H)—, —$NHSO_2$—, —$SO_2N(H)$—, —C(O)—O—, —$NHSO_2NH$—, —O—CO—, $R_{35}$, $R_{36}$, and $R_{37}$ independently are hydrogen, aryl, $C_1$-$C_6$ alkyl, $C_1$-$C_6$ alkylaryl, $C_1$-$C_6$ alkoxy, or $C_1$-$C_6$ alkoxyaryl, or a pharmaceutically acceptable salt thereof.

4. The compound of claim 1, wherein the compound is 3-(4-Benzyloxyphenyl)propionic Acid 2,4Di-(3-Diethylamino-1-propoxy)aniline Amide or a pharmaceutically acceptable salt thereof.

5. A pharmaceutical composition comprising the compound of Formula (I) as claimed in claim 1 or a pharmaceutically acceptable salt thereof, and one or more pharmaceutical acceptable carriers, excipients, or diluents.

6. The pharmaceutical composition of claim 5, in the form of an oral dosage or parenteral dosage unit.

7. The pharmaceutical composition of claim 5, wherein the pharmaceutical compositions is suitable for administration of said compound as a dose in a range from about 0.01 to 500 mg/kg of body weight per day.

8. The pharmaceutical composition of claim 5, wherein the pharmaceutical compositions is suitable for administration of said compound as a dose in a range from about 0.1 to 200 mg/kg of body weight per day.

9. The pharmaceutical composition of claim 5, wherein the pharmaceutical compositions is suitable for administration of said compound as a dose in a range from about 0.1 to 100 mg/kg of body weight per day.

10. The pharmaceutical composition of claim 5, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

11. A method for the inhibition of the interaction of RAGE with its physiological ligands, which comprises administering to a subject in need thereof, at least one compound of Formula (I) as claimed in claim 1 or a pharmaceutically acceptable salt thereof.

12. The method of claim 11, wherein the ligand(s) is(are) selected from advanced glycated end products (AGEs), S100/calgranulin/ENRAGE, β-amyloid and amphoterin.

13. A method for inhibiting RAGE in a subject having a disease state selected from the group consisting of acute and chronic inflammation, symptoms of diabetes, vascular permeability, nephropathy, atherosclerosis, retinopathy, Alzheimer's disease, erectile dysfunction, and tumor invasion and/or metastasis, which comprises administering to a subject in need thereof a therapeutically effective amount of at least one compound of Formula (I) as claimed in claim 1 or a pharmaceutically acceptable salt thereof.

14. A method of inhibiting RAGE in a human having a RAGE mediated human disease comprising administration to a human in need thereof a therapeutically effective amount of a compound of Formula (I) as claimed in claim 1, wherein a therapeutically effective amount comprises sufficient compound to at least partially inhibit the binding of a ligand to the RAGE receptor or a pharmaceutically acceptable salt thereof.

15. The method of claim 14, further comprising administering to a subject in need thereof at least one adjuvant and/or additional therapeutic agent(s).

16. A method of claim 14, wherein therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

17. The method claim 14, wherein the RAGE mediated human disease comprises acute and/or chronic inflammation.

18. The method claim 14, wherein the RAGE mediated human disease comprising vascular permeability.

19. The method claim 14, wherein the RAGE mediated human disease comprising nephropathy.

20. The method claim 14, wherein the RAGE mediated human disease comprising atherosclerosis.

21. The method claim 14, wherein the RAGE mediated human disease comprising retinopathy.

22. The method claim 14, wherein the RAGE mediated human disease comprising Alzheimer's disease.

23. The method claim 14, wherein the RAGE mediated human disease comprises erectile dysfunction.

24. The method claim 14, wherein the RAGE mediated human disease comprises tumor invasion and/or metastasis.

25. The compound of formula (I) in claim 1 or a pharmaceutically acceptable salt thereof, wherein $G_1$ is —$CH_2$—

$G_2$ is

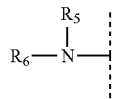

wherein
$R_5$ and $R_6$ are independently selected from the group consisting of
i) —H;
ii) —$C_{1-6}$ alkyl;
iii) -aryl;
iv) —$C_{1-6}$ alkylaryl;
v) —C(O)—O—$C_{1-6}$ alkyl;
vi) —C(O)—O—$C_{1-6}$ alkylaryl;
vii) —C(O)—O—$C_{1-6}$ alkylcycloalkylaryl;
viii) —C(O)—NH—$C_{1-6}$ alkyl;
ix) —C(O)—NH—$C_{1-6}$ alkylaryl;
x) —$SO_2$—$C_{1-6}$ alkyl;
xi) —$SO_2$—$C_{1-6}$ alkylaryl;
xii) —$SO_2$-aryl;
xiii) —$SO_2$—NH—$C_{1-6}$ alkyl;
xiv) —$SO_2$—NH—$C_{1-6}$ alkylaryl;

xv)

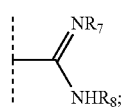

xvi) —C(O)—$C_{1-6}$ alkyl; or
xvii) —C(O)—$C_{1-6}$ alkylaryl;

$R_1$ is
a) hydrogen;
b) —$C_{1-6}$ alkyl;
c) -aryl; or
d) —$C_{1-6}$ alkylaryl;

$R_2$ is
a) —$C_{1-6}$ alkyl;
b) -aryl;
c) —$C_{1-6}$ alkylaryl; or
d) a group of the formula

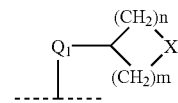

wherein m and n are independently selected from 1, 2, 3, or 4; X comprises a direct bond, $CH_2$—, —O—, —S—, —S($O_2$)—, —C(O)—, —CON(H)—, —NHC(O)—, NHCON(H)—, —$NHSO_2$—, —$SO_2N(H)$—, —C(O)—O—, —O—C(O)—, —$NHSO_2NH$—,

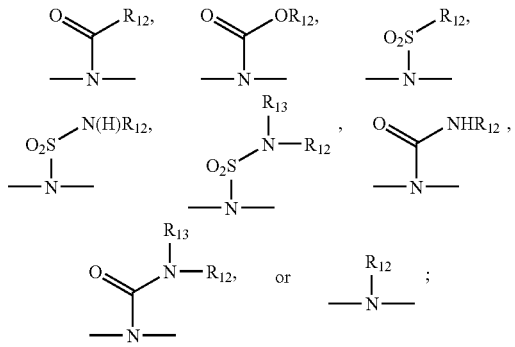

—$Q_1$— comprises $C_{1-6}$ alkylene, $C_{2-6}$ alkenylene, or $C_{2-6}$ alkynylene;

$R_3$ is
a) hydrogen;
b) —$C_{1-6}$ alkyl;
c) -aryl; or
d) —$C_{1-6}$ alkylaryl; and $R_4$ is a)
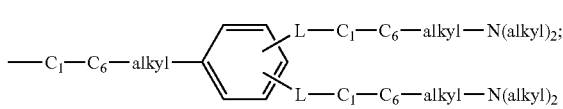

b)
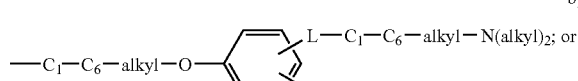
or c)
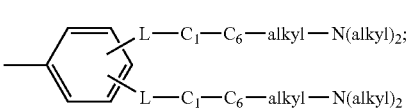

wherein L is —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

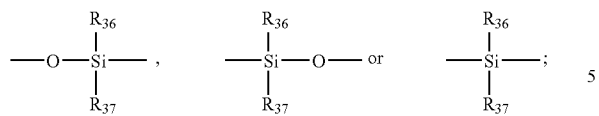

$R_{36}$ and $R_{37}$ are independently selected from the group consisting of hydrogen, aryl, $C_1$-$C_6$ alkyl, $C_1$-$C_6$ alkylaryl, $C_1$-$C_6$ alkoxy, and $C_1$-$C_6$ alkoxyaryl;

$R_{12}$ and $R_{13}$ are independently selected from the group consisting of hydrogen, $C_1$-$C_6$ alkyl, $C_1$-$C_6$ alkylaryl, and aryl;

$R_7$ and $R_8$ are independently selected from the group consisting of hydrogen, $C_1$-$C_6$ alkyl, $C_1$-$C_6$ alkylaryl, and aryl; or $R_7$ and $R_8$ are taken together to form a ring having the formula —$(CH_2)_{o'}$-$Z'$-$(CH_2)_{p'}$— bonded to the atoms to which $R_7$ and $R_8$ are attached, wherein o' and p' are, independently, 1, 2, 3, or 4; $Z'$ is a direct bond, —$CH_2$—, —O—, —S—, —$S(O_2)$—, —$C(O)$—, —$CON(H)$—, —$NHC(O)$—, —$NHCON(H)$—, —$NHSO_2$—, —$SO_2N(H)$—, —$C(O)$—O—, —O—$C(O)$—, —$NHSO_2NH$—,

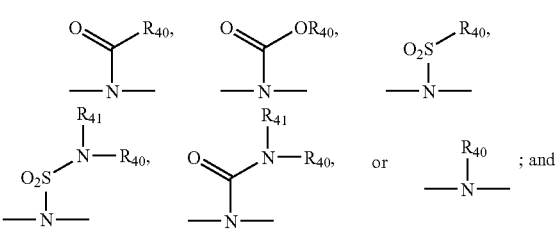

$R_{40}$ and $R_{41}$ are independently selected from the group consisting of hydrogen, aryl, $C_1$-$C_6$ alkyl, and $C_1$-$C_6$ alkylaryl; and wherein the aryl and/or alkyl group(s) in $R_1$, $R_2$, $R_3$, $R_4$, $R_5$, $R_6$, $R_7$, $R_8$, $R_{12}$ and $R_{13}$ may be optionally substituted 1-4 times with a substituent group, wherein said substituent group(s) or the term substituted refers to groups:

a) —H;
b) —Y—$C_{1-6}$ alkyl;
   —Y-aryl;
   —Y—$C_{1-6}$ alkylaryl;
   —Y—$C_{1-6}$-alkyl-$NR_{14}R_{15}$;
   —Y—$C_{1-6}$-alkyl-W-$R_{16}$;
   wherein Y and W are independently selected from the group consisting of —$CH_2$—, —O—, —N(H), —S—, $SO_2$—, —$CON(H)$—, —NHC(O)—, —NHCON(H)—, —NHSO$_2$—, —SO$_2$N(H)—, —C(O)—O—, —NHSO$_2$NH—, —O—CO—,

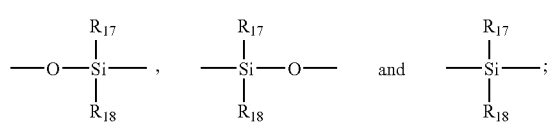

$R_{16}$, $R_{17}$ and $R_{18}$ are independently selected from the group consisting of hydrogen, aryl, $C_1$-$C_6$ alkyl, $C_1$-$C_6$ alkylaryl, $C_1$-$C_6$ alkoxy, and $C_{1-6}$ alkoxyaryl; and c) halogen, hydroxyl, cyano, carbamoyl, or carboxyl; and $R_{14}$ and $R_{15}$ are independently selected from the group consisting of hydrogen, aryl, $C_1$-$C_6$ alkyl, and $C_1$-$C_6$ alkylaryl; or $R_{14}$ and $R_{15}$ are taken together to form a ring having the formula —$(CH_2)_o$-Z-$(CH_2)_p$— bonded to the nitrogen atom to which $R_{14}$ and $R_{15}$ are attached, wherein o and p are, independently, 1, 2, 3, or 4; Z is a direct bond, —$CH_2$—, —O—, —S—, —$S(O_2)$—, —$C(O)$—, —$CON(H)$—, —$NHC(O)$—, —$NHCON(H)$—, —$NHSO_2$—, —$SO_2N(H)$—, —$C(O)$—O—, —O—$C(O)$—, —$NHSO_2NH$—,

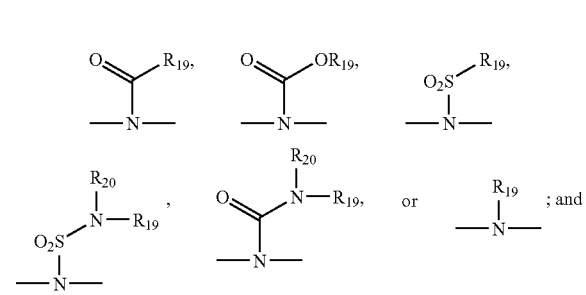

$R_{19}$ and $R_{20}$ are independently selected from the consisting of hydrogen, aryl, $C_1$-$C_6$ alkyl, and $C_1$-$C_6$ alkylaryl.

26. The compound of formula (I) in claim 25 or a pharmaceutically acceptable salt thereof, wherein $G_1$ is —$CH_2$—

$G_2$ is

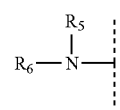

wherein $R_5$ is —H; and $R_6$ is i) —H;

ii) —$C_{1-6}$ alkyl; or iii) —$C(O)$—O—$C_{1-6}$ alkylcycloalkylaryl;

$R_1$ is —H;

$R_2$ is

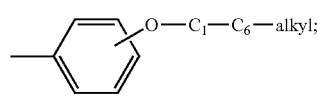

$R_3$ is —H; and
$R_4$ is

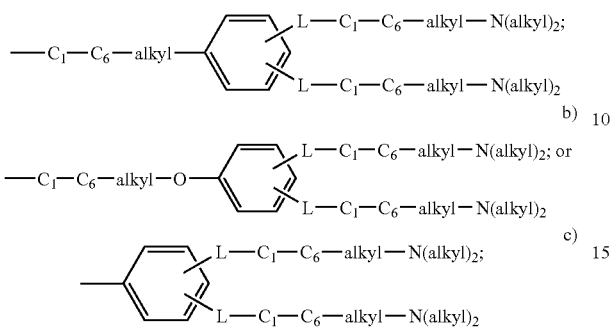

wherein L is —$CH_2$—, —O—, —N(H)—, —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

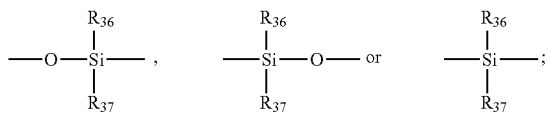

$R_{36}$ and $R_{37}$ are independently selected from the group consisting of hydrogen, aryl, $C_1$-$C_6$ alkyl, $C_1$-$C_6$ alkylaryl, $C_1$-$C_6$ alkoxy, and $C_1$-$C_6$ alkoxyaryl;
and wherein
the aryl and/or alkyl group(s) in $R_1$, $R_2$, $R_3$, $R_4$, $R_5$, $R_6$, $R_7$, $R_{8,\ 12}$, and $R_{13}$ may be optionally substituted 1-4 times with a substituent group, wherein said substituent group(s) or the term substituted refers to groups:
a) —H;
b) —Y—$C_{1-6}$ alkyl;
—Y-aryl;
—Y—$C_{1-6}$ alkylaryl;
—Y—$C_{1-6}$-alkyl-$NR_{14}R_{15}$;
—Y—$C_{1-6}$-alkyl-W-$R_{16}$;
wherein Y and W are independently selected from the group consisting of —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

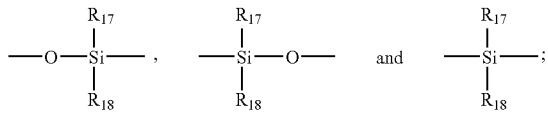

$R_{16}$, $R_{17}$ and $R_{18}$ are independently selected from the group consisting of hydrogen, aryl, $C_1$-$C_6$ alkyl, $C_1$-$C_6$ alkylaryl, $C_1$-$C_6$ alkoxy, and $C_1$-$C_6$ alkoxyaryl; and
c) halogen, hydroxyl, cyano, carbamoyl, or carboxyl; and $R_{14}$ and $R_{15}$ are independently selected from the group consisting of hydrogen, aryl, $C_1$-$C_6$ alkyl, and $C_1$-$C_6$ alkylaryl; or $R_{14}$ and $R_{15}$ are taken together to form a ring having the formula —$(CH_2)_o$-Z-$(CH_2)_p$— bonded to the nitrogen atom to which $R_{14}$ and $R_{15}$ are attached, wherein o and p are, independently, 1, 2, 3, or 4; Z is a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

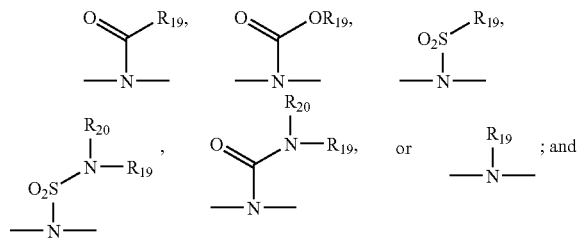

$R_{19}$ and $R_{20}$ are independently selected from the consisting of hydrogen, aryl, $C_1$-$C_6$ alkyl, and $C_1$-$C_6$ alkylaryl.

27. A pharmaceutical composition comprising the compound of Formula (I) as claimed in claim 2 or a pharmaceutically acceptable salt thereof, and one or more pharmaceutically acceptable carriers, excipients, or diluents.

28. A pharmaceutical composition comprising the compound of Formula (I) as claimed in claim 3 or a pharmaceutically acceptable salt thereof, and one or more pharmaceutically acceptable carriers, excipients, or diluents.

29. A pharmaceutical composition comprising the compound of Formula (I) as claimed in claim 4 or a pharmaceutically acceptable salt thereof, and one or more pharmaceutically acceptable carriers, excipients, or diluents.

30. The compound of claim 25, wherein the compound is 3-(3-Tert-butoxyphenyl)-3-(9-fluorenylmethoxycarbonylamino)propionic Acid 2,4-Di-(3-diethylaminopropoxy)aniline Amide or a pharmaceutically acceptable salt thereof.

31. The compound of claim 26, wherein the compound is 3-(3-Tert-butoxyphenyl)-3-aminopropionic Acid 2,4-Di-(3-diethylaminopropoxy)aniline Amide or a pharmaceutically acceptable salt thereof.

32. The compound of claim 25, wherein the compound is 3-(4-Tert-butoxyphenyl)-3-(9-fluorenylmethoxycarbonylamino)propionic Acid 2,4-Di-(3-diethylaminopropoxy)aniline Amide or a pharmaceutically acceptable salt thereof.

33. The compound of claim 26, wherein the compound is 3-amino-3-(4-tert-butoxyphenyl)propionic Acid 2,4-Di-(3-diethylaminopropoxy)aniline Amide or a pharmaceutically acceptable salt thereof.

34. The compound of claim 25, wherein the compound is 3-(9-fluorenylmethoxycarbonylamino)-3-(2-tert-butoxyphenyl)propionic Acid 2,4-Di-(3-diethylaminopropoxy)aniline Amide or a pharmaceutically acceptable salt thereof.

35. The compound of claim 26, wherein the compound is 3-amino-3-(2-tert-butoxyphenyl)propionic Acid 2,4-Di-(3-diethylaminopropoxy)aniline Amide or a pharmaceutically acceptable salt thereof.

36. The compound of claim 26, wherein the compound is 3-Isopropylamino-3-(3-tert-butoxyphenyl)propionic Acid 2,4-Di-(3-diethylaminopropoxy)aniline Amide or a pharmaceutically acceptable salt thereof.

37. A pharmaceutical composition comprising the compound of Formula (I) as claimed in claim 30 or a pharmaceutically acceptable salt thereof, and one or more pharmaceutically acceptable carriers, excipients, or diluents.

38. A pharmaceutical composition comprising the compound of Formula (I) as claimed in claim 31 or a pharmaceutically acceptable salt thereof, and one or more pharmaceutically acceptable carriers, excipients, or diluents.

39. A pharmaceutical composition comprising the compound of Formula (I) as claimed in claim 32 or a pharmaceutically acceptable salt thereof, and one or more pharmaceutically acceptable carriers, excipients, or diluents.

40. A pharmaceutical composition comprising the compound of Formula (I) as claimed in claim 33 or a pharmaceutically acceptable salt thereof, and one or more pharmaceutically acceptable carriers, excipients, or diluents.

41. A pharmaceutical composition comprising the compound of Formula (I) as claimed in claim 34 or a pharmaceutically acceptable salt thereof, and one or more pharmaceutically acceptable carriers, excipients, or diluents.

42. A pharmaceutical composition comprising the compound of Formula (I) as claimed in claim 35 or a pharmaceutically acceptable salt thereof, and one or more pharmaceutically acceptable carriers, excipients, or diluents.

43. A pharmaceutical composition comprising the compound of Formula (I) as claimed in claim 36 or a pharmaceutically acceptable salt thereof, and one or more pharmaceutically acceptable carriers, excipients, or diluents.

* * * * *

UNITED STATES PATENT AND TRADEMARK OFFICE
CERTIFICATE OF CORRECTION

PATENT NO.         : 7,423,177 B2
APPLICATION NO.    : 10/091759
DATED              : September 9, 2008
INVENTOR(S)        : Adnan M. M. Mjalli et al.

It is certified that error appears in the above-identified patent and that said Letters Patent is hereby corrected as shown below:

Title page, under Foreign Patent Documents, please delete "WO 9739125," please insert -- WO 97/39125 --.

Page 2, Column 1, line 27, under Other Publications, please delete "Avanced", please insert -- Advanced --.

Page 2, Column 2, line 22, under Other Publications, please delete "Therpy", please insert -- Therapy --.

Page 2, Column 2, line 29, under Other Publications, please delete "Factor$_K$B", please insert -- Factor-$_K$B --.

Column 1, line 55, please delete "immunoglobulintype", please insert -- immunoglobulin-type --.

Column 1, line 66, please delete "(Schleicheret al.,", please insert -- (Schleicher et al., --.

Column 2, line 8, please delete "Invest", please insert -- Invest. --.

Column 2, line 22, please delete "Hofmann", please insert -- (Hofmann --.

Column 2, lines 27-28, please delete "ENRAGE,", please insert -- EN-RAGE, --.

Column 3, line 25 (approx.), After "hydrogen", please insert -- ; --.

Column 3, line 30 (approx.), After "alkylaryl", please insert -- ; --.

Column 3, line 44 (approx.), please delete "-$C_{1-6}$,", please insert -- -$C_{1-6}$ --.

Column 4, line 58 (approx.), please delete "$CH_2$-,", please insert -- -$CH_2$-, --.

Column 5, line 40, please delete "-NHCON(H),", please insert -- -NHCON(H)-, --.

Column 6, line 44, please delete "$NHSO_2$-,", please insert -- -$NHSO_2$-, --.

UNITED STATES PATENT AND TRADEMARK OFFICE
CERTIFICATE OF CORRECTION

PATENT NO.       : 7,423,177 B2
APPLICATION NO.  : 10/091759
DATED            : September 9, 2008
INVENTOR(S)      : Adnan M. M. Mjalli et al.

It is certified that error appears in the above-identified patent and that said Letters Patent is hereby corrected as shown below:

Column 9, line 1, please delete "$R_{17}$", please insert -- $R_{17}$, --.

Column 9, line 34, please delete "$R_6$may", please insert -- $R_6$ may --.

Column 10, line 32, After "-H", please insert -- ; --.

Column 10, line 52, After "-H", please insert -- ; --.

Column 11, line 24, please delete "$R_{36}$", please insert -- $R_{36}$, --.

Column 13, line 49, please delete "X)", please insert -- x) --.

Column 14, line 18 (approx.), please delete "-NHCON(H),", please insert -- -NHCON(H)-, --.

Column 14, line 30, please delete "$C_{1-6}$", please insert -- $C_1$-$C_6$ --.

Column 15, line 21 (approx.), please delete "$CH_2$-,", please insert -- -$CH_2$-, --.

Column 16, line 7, please delete "$NHSO_2$-,", please insert -- -$NHSO_2$-, --.

Column 16, lines 11-15 (approx.), please delete " [structure] ;", please insert -- [structure] ; --.

Column 20, line 2 (Example 5) (Table 1), please delete "2,4-Di(3-diethylamino-1-", please insert -- 2,4-Di-(3-diethylamino-1- --.

Column 27, line 2 (Structure) (Example 20) (Table 1), please delete "$NH_2$", please insert -- NH- --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 32, line 3 (Example 26) (Table 1), please delete "fluorenylmethoxycarbonyamino)", please insert -- fluorenylmethoxycarbonylamino) --.

Column 34, lines 66-67, please delete "anti psychotics,", please insert -- antipsychotics, --.

Column 34, line 67, please delete "anti depressants,", please insert -- antidepressants, --.

Column 35, line 39 (approx.), please delete "Alzheimees", please insert -- Alzheimer's --.

Column 36, line 22, please delete "ispropyloxy", please insert -- isopropyloxy --.

Column 36, line 32 (approx.), please delete "inline", please insert -- in-line --.

Column 36, line 56 (approx.), please delete "acyamino", please insert -- acylamino --.

Column 38, line 20 (approx.), please delete "tertbutoxycarbonyl,", please insert -- tert-butoxycarbonyl, --.

Column 38, line 22, please delete "proptecting", please insert -- protecting --.

Column 38, line 62 (approx.), please delete "equvalent", please insert -- equivalent --.

Column 38, line 63, After "is" please delete "is".

Column 39, line 1, After "is" please delete "is".

Column 40, line 15 (approx.), please delete "duisopropyl", please insert -- diisopropyl --.

Column 40, line 44 (approx.), before "acid", please delete "a", please insert -- an --.

Column 40, line 50, before "tertiary", please delete "an", please insert -- a --.

Column 40, line 63 (approx.)(Scheme 6), please delete "(R$_{48}$", please insert -- R$_{48}$ --.

Column 40, line 65 (approx.)(Scheme 6), please delete "(R$_{48}$", please insert -- R$_{48}$ --.

Column 42, line 46 (approx.), please delete "dimethypropylene", please insert -- dimethylpropylene --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 44, line 10, please delete "complete ty", please insert -- completely by --.

Column 44, line 50 (approx.), after "and the", please delete "the".

Column 45, line 3, after "water and", please delete "and".

Column 45, line 6, please delete "Azodicarboxyate", please insert -- Azodicarboxylate --.

Column 45, line 10, please delete "duisopropyl", please insert -- diisopropyl --.

Column 45, line 10, please delete "azodicaroxylate", please insert -- azodicarboxylate --.

Column 45, line 52, please delete "with 1 N HCl", please insert -- 1 N HCl --.

Column 45, line 58 (approx.), after "(2.6 g)", please insert -- . --.

Column 46, line 19, please delete "SnCl2H$_2$O", please insert -- SnCl$_2$H$_2$O --.

Column 46, line 38, please delete "Amideas", please insert -- Amide as --.

Column 47, line 8 (approx.), please delete "Acid2,4-", please insert -- Acid 2,4- --.

Column 47, line 63, please delete "Na2SO$_4$.", please insert -- Na$_2$SO$_4$ --.

Column 47, line 67, please delete "Tr", please insert -- T$_r$ --.

Column 48, lines 15-22 (approx.), please delete " 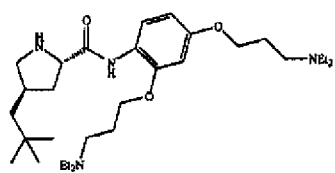 ", please insert -- 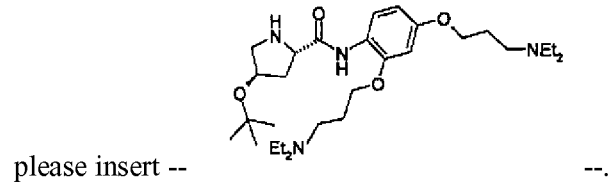 --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 48, line 23, please delete "4R)-4tert-butoxy-1 –(9-", please insert -- 4R)-4-tert-butoxy-1-(9- --.

Column 48, line 36, after "(M+H)$^+$", please insert -- . --.

Column 48, line 62, please delete "2-butoxy4-", please insert -- 2-butoxy-4- --.

Column 49, line 9, please delete "Tr", please insert -- $T_r$ --.

Column 49, line 9, after "(M+H)", please insert -- . --.

Column 49, line 15 (approx.), after "according", please insert -- to --.

Column 49, lines 37-38 (approx.), please delete "triethylamime", please insert -- triethylamine --.

Column 49, line 39, please delete "butoxyan iline", please insert -- butoxyaniline --.

Column 49, line 45, please delete "Tr", please insert -- $T_r$ --.

Column 49, line 51, please delete "Tr", please insert -- $T_r$ --.

Column 51, line 1, please delete "3-(9fluorenylmethoxycarbonylamino)", please insert -- 3-(9-fluorenylmethoxycarbonylamino) --.

Column 51, line 3, please delete "end", please insert -- and --.

Column 51, line 7, please delete "Tr", please insert -- $T_r$ --.

Column 51, line 14 (approx.), please delete "anline", please insert -- aniline --.

Column 51, line 35 (approx.), after "(M+H)$^+$", please insert -- . --.

Column 52, line 7, please delete "Tr", please insert -- $T_r$ --.

Column 52, line 35 (approx.), after "(M+H)$^+$", please insert -- . --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 52, line 64, before "vacuo", please delete "removed in".

Column 52, line 66, please delete "Tr", please insert -- $T_r$ --.

Column 52, line 67, after "(M+H)$^+$" please insert -- . --.

Column 53, lines 27-28, please delete "butyidimethylsilyl", please insert -- butyldimethylsilyl --.

Column 53, line 29, please delete "accroding", please insert -- according --.

Column 53, line 31, please delete "Tr", please insert -- $T_r$ --.

Column 53, line 63, please delete "butyidimethylsilyl", please insert -- butyldimethylsilyl --.

Column 53, line 67, please delete "Tr", please insert -- $T_r$ --.

Column 54, line 31 (approx.), please delete "butyidimethylsilyl", please insert -- butyldimethylsilyl --.

Column 54, lines 33-34, please delete "butyidimethylsilyl", please insert -- butyldimethylsilyl --.

Column 55, line 34, please delete "butyidimethylsilyl", please insert -- butyldimethylsilyl --.

Column 55, line 36, please delete "butyidimethylsil", please insert -- butyldimethylsilyl --.

Column 55, line 37, please delete "NBoc-", please insert -- N-Boc- --.

Column 55, line 41, please delete "Tr", please insert -- $T_r$ --.

Column 56, line 44 (approx.), please delete "Boc-Tyr(Bzl-OH", please insert -- Boc-Tyr(Bzl)-OH --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 56, line 47 (approx.), please delete "Tr", please insert -- $T_r$ --.

Column 57, line 19 (approx.), please delete "Tr", please insert -- $T_r$ --.

Column 58, line 42 (approx.), after "agent," please delete "The", please insert -- the --.

Column 58, line 49 (approx.), please delete "Tr", please insert -- $T_r$ --.

Column 59, line 2, please delete "Tr", please insert -- $T_r$ --.

Column 59, line 3, please delete "(M+H)$^{+\cdot}$", please insert -- (M+H)$^+$. --.

Column 59, lines 34-35 (approx.), please delete "2-butoxy4-", please insert
-- 2-butoxy-4- --.

Column 59, line 47 (approx.), please delete "Tr", please insert -- $T_r$ --.

Column 60, line 2, please delete "Tr", please insert -- $T_r$ --.

Column 60, line 49 (approx.), please delete "Tr", please insert -- $T_r$ --.

Column 60, line 66 (approx.), please delete "Tr", please insert -- $T_r$ --.

Column 61, lines 1-2, please delete "(9-fluorenylmethoxycarbonyamino)", please insert
-- (9-fluorenylmethoxycarbonylamino) --.

Column 61, line 33 (approx.), after "Na$_2$SO$_4$." please delete "the", please insert
-- The --.

Column 61, line 35 (approx.), please delete "Tr", please insert -- $T_r$ --.

Column 62, line 35 (approx.), please delete "Tr", please insert -- $T_r$ --.

Column 62, line 67 (approx.), please delete "Tr", please insert -- $T_r$ --.

Column 63, line 42 (approx.), please delete "(3-N-Boc-piperidinyl-OH", please insert
-- (3-N-Boc-piperidinyl)-OH --.

UNITED STATES PATENT AND TRADEMARK OFFICE
CERTIFICATE OF CORRECTION

| | | |
|---|---|---|
| PATENT NO. | : 7,423,177 B2 | |
| APPLICATION NO. | : 10/091759 | |
| DATED | : September 9, 2008 | |
| INVENTOR(S) | : Adnan M. M. Mjalli et al. | |

It is certified that error appears in the above-identified patent and that said Letters Patent is hereby corrected as shown below:

Column 63, line 45, please delete "Tr", please insert -- $T_r$ --.

Column 64, line 2, please delete "Tr", please insert -- $T_r$ --.

Column 64, line 29 (approx.), please delete "(400 uL/well)", please insert -- (400 µL/well) --.

Column 64, line 36 (approx.), please delete "SRAGE", please insert -- sRAGE --.

Column 64, line 47, please delete "Sterptavidin", please insert -- Streptavidin --.

Column 64, line 53, please delete "$Ca_2Cl_2$.", please insert -- $CaCl_2$. --.

Column 66, line 40, please delete "alchol.", please insert -- alcohol. --.

Column 67, line 1, please delete "injectible", please insert -- injectable --.

Column 67, line 6, please delete "nontoxic", please insert -- non-toxic --.

Column 67, line 11, after "medium", please insert -- . --.

Column 67, line 51, please delete "Nmethylglucamine,", please insert -- N-methylglucamine, --.

Column 67, line 52, please delete "Phosphateldiphosphate,", please insert -- Phosphate/diphosphate, --.

Column 67, line 62, please delete "oxiate,", please insert -- oxalate, --.

Column 68, line 11, please delete "therof,", please insert -- thereof, --.

Column 68, line 56, please delete "overtime", please insert -- over time --.

Column 70, line 3, please delete "et at.,", please insert -- et al., --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 70, line 37, please delete "Stem,", please insert -- Stern, --.

Column 71, line 67, please delete "Mefformin", please insert -- Metformin --.

Column 72, line 53, please delete "therof,", please insert -- thereof, --.

Column 73, line 15, In Claim 1, after "hydrogen", please insert -- ; --.

Column 74, line 14, In Claim 1, after "-hydrogen", please insert -- ; --.

Column 74, line 15, In Claim 1, please delete "ii", please insert -- ii) --.

Column 74, line 53 (approx.), In Claim 1, please delete "comprises", please insert -- is --.

Column 74, line 53 (approx.), In Claim 1, please delete "$CH_2$-,", please insert -- -$CH_2$-, --.

Column 75, line 46, In Claim 1, after "independently", please insert -- selected --.

Column 75, line 52, In Claim 1, after "independently", please insert -- selected --.

Column 76, line 9 (approx.), In Claim 1, after "independently", please insert -- selected --.

Column 76, line 39, In Claim 1, please delete "$R_{17}$", please insert -- $R_{17}$, --.

Column 76, line 41, In Claim 1, please delete "or $C_{1-6}$", please insert -- $C_1$-$C_6$ --.

Column 76, line 41, In Claim 1, please delete "or", please insert -- and --.

Column 77, line 1, In Claim 1, after "the", please insert -- group --.

Column 77, line 2, In Claim 1, please delete "$C_1$-C alkyl,", please insert -- and $C_1$-$C_6$ alkyl, --.

UNITED STATES PATENT AND TRADEMARK OFFICE
CERTIFICATE OF CORRECTION

| | |
|---|---|
| PATENT NO. | : 7,423,177 B2 |
| APPLICATION NO. | : 10/091759 |
| DATED | : September 9, 2008 |
| INVENTOR(S) | : Adnan M. M. Mjalli et al. |

It is certified that error appears in the above-identified patent and that said Letters Patent is hereby corrected as shown below:

Column 77, line 2, In Claim 1, please delete "alkyl.", please insert -- alkylaryl, --.

Column 77, line 13 (approx.), In Claim 2, after "wherein", please insert -- , --.

Column 78, line 16, In Claim 4, please delete "2,4Di-", please insert -- 2,4-Di- --.

Column 78, lines 21-22 (approx.), In Claim 5, please delete "pharmaceutical", please insert -- pharmaceutically --.

Column 78, line 26, In Claim 7, please delete "compositions", please insert -- composition --.

Column 78, line 30, In Claim 8, please delete "compositions", please insert -- composition --.

Column 78, line 34, In Claim 9, please delete "compositions", please insert -- composition --.

Column 78, line 51, In Claim 12, please delete "ENRAGE,", please insert -- EN-RAGE, --.

Column 79, line 4, In Claim 16, please delete "claim 14, wherein therapeutic agents selected", please insert -- claim 15, wherein the therapeutic agents are selected --.

Column 79, line 11, In Claim 17, after "method", please insert -- of --.

Column 79, line 13, In Claim 18, after "method", please insert -- of --.

Column 79, line 14, In Claim 18, please delete "comprising", please insert -- comprises --.

Column 79, line 15, In Claim 19, after "method", please insert -- of --.

Column 79, line 16, In Claim 19, please delete "comprising", please insert -- comprises --.

Column 79, line 17, In Claim 20, after "method", please insert -- of --.

UNITED STATES PATENT AND TRADEMARK OFFICE
CERTIFICATE OF CORRECTION

PATENT NO.        : 7,423,177 B2
APPLICATION NO.   : 10/091759
DATED             : September 9, 2008
INVENTOR(S)       : Adnan M. M. Mjalli et al.

It is certified that error appears in the above-identified patent and that said Letters Patent is hereby corrected as shown below:

Column 79, line 18, In Claim 20, please delete "comprising", please insert -- comprises --.

Column 79, line 19, In Claim 21, after "method", please insert -- of --.

Column 79, line 20, In Claim 21, please delete "comprising", please insert -- comprises --.

Column 79, line 21, In Claim 22, after "method", please insert -- of --.

Column 79, line 22, In Claim 22, please delete "comprising", please insert -- comprises --.

Column 79, line 23, In Claim 23, after "method", please insert -- of --.

Column 79, line 25, In Claim 24, after "method", please insert -- of --,

Column 79, line 27, In Claim 25, please delete "formula", please insert -- Formula --.

Column 80, line 17, In Claim 25, please delete "comprises", please insert -- is --.

Column 80, line 17, In Claim 25, please delete "CH$_2$-,", please insert -- -CH$_2$- --.

Column 80, line 19 (approx.), In Claim 25, please delete "NHCON(H)-,", please insert -- -NHCON(H)-, --.

Column 80, line 38, In Claim 25, please delete "comprises", please insert -- is --.

Column 80, line 43, In Claim 25, please delete "-aryl; or", please insert -- -C$_{1-6}$alkylaryl; or --.

Column 80, line 44, In Claim 25, please delete "-C$_{1-6}$alkylaryl; and", please insert -- -C$_{1-6}$alkoxyaryl; and --.

Column 82, line 1, In Claim 25, please delete "R$_{17}$", please insert -- R$_{17}$, --.

UNITED STATES PATENT AND TRADEMARK OFFICE
CERTIFICATE OF CORRECTION

PATENT NO. : 7,423,177 B2
APPLICATION NO. : 10/091759
DATED : September 9, 2008
INVENTOR(S) : Adnan M. M. Mjalli et al.

It is certified that error appears in the above-identified patent and that said Letters Patent is hereby corrected as shown below:

Column 82, line 3, In Claim 25, please delete "$C_{1-6}$", please insert -- $C_1$-$C_6$ --.

Column 82, line 5, In Claim 25, please delete "or", please insert -- and --.

Column 82, line 34, In Claim 25, after "the", please insert -- group --.

Column 82, line 36, In Claim 26, please delete "formula", please insert -- Formula --.

Column 83, line 38, In Claim 26, please delete "$_{12}$,", please insert -- $R_{12}$, --.

Column 83, line 62 (approx.), In Claim 26, please delete "$R_{17}$", please insert -- $R_{17}$, --.

Column 84, line 25, In Claim 26, after "the", please insert -- group --.

Signed and Sealed this

Twelfth Day of May, 2009

JOHN DOLL
*Acting Director of the United States Patent and Trademark Office*